United States Patent
Egawa et al.

(10) Patent No.: US 8,704,215 B2
(45) Date of Patent: *Apr. 22, 2014

(54) STILBENE DERIVATIVES, LIGHT-EMITTING ELEMENT, DISPLAY DEVICE, AND ELECTRONIC DEVICE

(75) Inventors: Masakazu Egawa, Tochigi (JP); Harue Osaka, Kanagawa (JP); Sachiko Kawakami, Kanagawa (JP); Nobuharu Ohsawa, Kanagawa (JP); Satoshi Seo, Kanagawa (JP); Ryoji Nomura, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 49 days.

This patent is subject to a terminal disclaimer.

(21) Appl. No.: 13/417,219

(22) Filed: Mar. 10, 2012

(65) Prior Publication Data

US 2012/0168741 A1    Jul. 5, 2012

Related U.S. Application Data

(63) Continuation of application No. 12/794,893, filed on Jun. 7, 2010, now Pat. No. 8,134,148, which is a continuation of application No. 11/860,712, filed on Sep. 25, 2007, now Pat. No. 7,732,619.

(30) Foreign Application Priority Data

Sep. 29, 2006 (JP) .................................. 2006-270118

(51) Int. Cl.
   *H01L 51/54* (2006.01)
   *C07D 211/54* (2006.01)
   *C07D 209/86* (2006.01)
   *C07D 403/12* (2006.01)

(52) U.S. Cl.
   USPC ...... 257/40; 257/E51.025; 548/440; 548/442; 564/434

(58) Field of Classification Search
   USPC ..................... 257/40, E51.025; 548/440, 442; 564/434
   See application file for complete search history.

(56) References Cited

U.S. PATENT DOCUMENTS

| | | | |
|---|---|---|---|
| 5,085,946 | A | 2/1992 | Saito et al. |
| 6,468,675 | B1 | 10/2002 | Ishikawa et al. |
| 6,743,948 | B1 | 6/2004 | Hosokawa et al. |
| 6,951,693 | B2 | 10/2005 | Hosokawa et al. |

(Continued)

FOREIGN PATENT DOCUMENTS

| | | |
|---|---|---|
| EP | 1 314 715 A1 | 5/2003 |
| JP | 6-33047 | 2/1994 |

(Continued)

OTHER PUBLICATIONS

Cha, S.W. et al, "Electroluminescence of LEDs Consisting Two Layers of Alq₃ and High $T_g$, Blue-Light Emitting Branched Compounds," Synthetic Metals, vol. 143, No. 1, 2004, pp. 97-101.

*Primary Examiner* — Yong Chu
(74) *Attorney, Agent, or Firm* — Husch Blackwell LLP

(57) ABSTRACT

A novel stilbene derivative is provided with motivation of providing a blue emissive material showing excellent color purity. The use of the stilbene derivative of the present invention allows the fabrication of a blue-emissive light-emitting element with excellent color purity. The invention also includes an electronic device equipped with a display portion in which the stilbene derivative is employed. The stilbene derivative of the present invention is represented by formula (1), in which $Ar^1$ and $Ar^2$ may form a 5-membered ring by being directly bonded to each other. In formula (1), $A^{11}$ represents any one of substituents represented by general formulas (1-1) to (1-3). The variables shown in formula (1) and (1-1) to (1-3) are as defined in the specification.

8 Claims, 25 Drawing Sheets (1)

$$Ar^2\diagdown_{Ar^1}\!\!N\!-\!\!\!\bigcirc\!\!\!-CH=CH-\!\!\!\bigcirc\!\!\!-A^{11}$$

(1-1)

(1-2)

(1-3)

(56) References Cited

U.S. PATENT DOCUMENTS

| | | |
|---|---|---|
| 7,122,256 B2 | 10/2006 | Funahashi et al. |
| 7,476,745 B2 * | 1/2009 | Egawa et al. ................ 548/440 |
| 2003/0072966 A1 | 4/2003 | Hosokawa et al. |
| 2005/0238912 A1 | 10/2005 | Funahashi et al. |
| 2006/0189828 A1 | 8/2006 | Hosokawa et al. |
| 2007/0080630 A1 | 4/2007 | Egawa et al. |
| 2007/0142671 A1 | 6/2007 | Hosokawa et al. |
| 2007/0215889 A1 | 9/2007 | Kawakami et al. |

FOREIGN PATENT DOCUMENTS

| | | |
|---|---|---|
| JP | 2004-75580 | 3/2004 |
| JP | 2004-196716 | 7/2004 |
| WO | WO 00/39247 A1 | 7/2000 |
| WO | WO 02/20459 A1 | 3/2002 |

* cited by examiner

STILBENE DERIVATIVES, LIGHT-EMITTING ELEMENT, DISPLAY DEVICE, AND ELECTRONIC DEVICE

This application is a continuation of copending application Ser. No. 12/794,893 filed on Sep. 25, 2007 which is a continuation of application Ser. No. 11/860,712 filed on Sep. 25, 2007 (now U.S. Pat. No. 7,732,619 issued Jun. 8, 2010). This application, via its grandparent application Ser. No. 11/860,712, claims priority under 35 USC §119 to Japanese Patent Application serial no. JP 2006-270118 filed on Sep. 29, 2006 in Japan.

BACKGROUND OF THE INVENTION

1. Field of the Invention

The present invention relates to stilbene derivatives, light-emitting elements which use stilbene derivatives, display devices having the light-emitting elements, and electronic devices having the display devices. In more detail, the present invention relates to novel stilbene derivatives which can provide excellent color purity of blue; and light-emitting elements, display devices, and electronic devices which use the stilbene derivatives.

2. Description of the Related Art

Light-emitting elements have features such as low-voltage drive, high efficiency, and high luminance and are expected to be applied to flat panel displays of the next generation. It is considered that a light-emitting device in which light-emitting elements are used for a pixel portion is superior to a conventional liquid crystal display device in viewing angle and visibility.

A light-emitting element is formed by interposing a layer including a luminescent substance between a pair of electrodes (an anode and a cathode). An emission mechanism thereof is regarded as follows: when voltage is applied between the pair of electrodes, holes injected from the anode and electrons injected from the cathode recombine in a light-emitting layer including a luminescent substance, whereby a molecular exciton is formed, and energy is released when the molecular exciton relaxes to a ground state. Thus, light is emitted. A luminescent substance can exist in singlet excited state and a triplet excited state. Light emission from a singlet excited state is referred to as fluorescence and light emission from a triplet excited state is referred to as phosphorescence.

An emission wavelength of a light-emitting element is determined by an energy difference between a ground state and an excited state, that is, a band gap, of a light-emitting molecule included in the light-emitting element. Therefore, various emission colors can be obtained by devising a structure of the light-emitting molecule. By using the light-emitting elements capable of emitting red light, blue light, or green light, which are the three primary colors of light, a full-color light-emitting device can be manufactured. Accordingly, highly reliable light-emitting elements which are excellent in color purity and emit red light, blue light, or green light are being investigated.

As a result of recent development of materials, red emissive and green emissive light-emitting element with high reliability and excellent color purity have been realized. However, a blue emissive light emitting element having sufficient reliability and color purity has not yet been developed in spite of intensive research thereon (for example, see Reference 1: Japanese Published Patent Application No. 2004-75580).

SUMMARY OF THE INVENTION

In view of the foregoing issues, an object of the present invention is to provide a novel, blue emissive substance which provides excellent color purity; and a light-emitting element, a display device, and an electronic device which use the novel substance.

The present invention provides novel stilbene derivatives. One feature of a stilbene derivative of the present invention includes a structure shown in the following general formula (1).

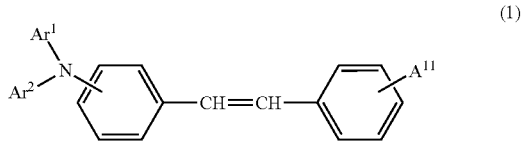

(1)

In the general formula (1), $Ar^1$ and $Ar^2$ each represent an aryl group having 6 to 25 carbon atoms, and the aryl group may include an alkyl group having 1 to 4 carbon atoms. Further, $Ar^1$ and $Ar^2$ may form a 5-membered ring by being directly bonded to each other. $A^{11}$ represents any one of substituents represented by the general formulas (1-1) to (1-3) below. Further, the bonding positions of nitrogen which includes $Ar^1$ and $Ar^2$ and $A^{11}$ may be any of an ortho position (ortho-substituted), a meta position (meta-substituted), and a para position (para-substituted) with respect to a double bond of stilbene. In other words, the diarylamino group ($NAr^1Ar^2$) and $A^{11}$ can be independently para-substituted, meta-substituted, or ortho-substituted on the benzene rings with respect to the double bond (CH=CH).

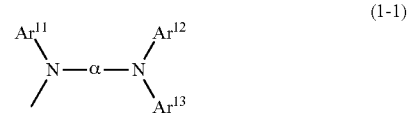

(1-1)

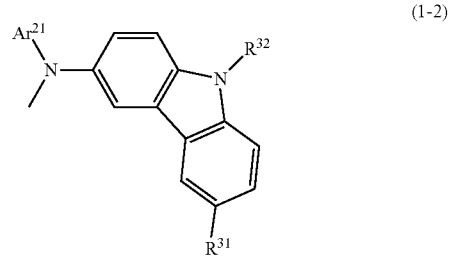

(1-2)

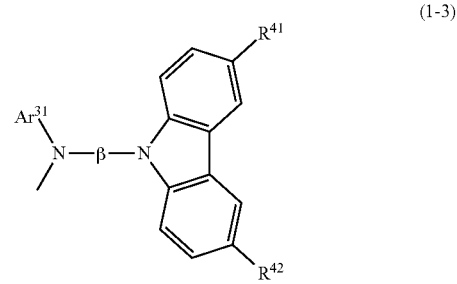

(1-3)

In the general formulas (1-1) to (1-3), $Ar^{11}$ to $Ar^{13}$ each represent an aryl group having 6 to 25 carbon atoms; α represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents any one of an alkyl group having 1 to 4 carbon atoms and an aryl group having 6 to 25 carbon atoms;

$Ar^{31}$ represents an aryl group having 6 to 25 carbon atoms; β represents an arylene group having 6 to 25 carbon atoms; and $R^{41}$ and $R^{42}$ each represent any one of a hydrogen atom, an alkyl group having 1 to 4 carbon atoms, and an aryl group having 6 to 25 carbon atoms.

Another feature of a stilbene derivative of the present invention includes a structure shown in the following general formula (2).

(2)

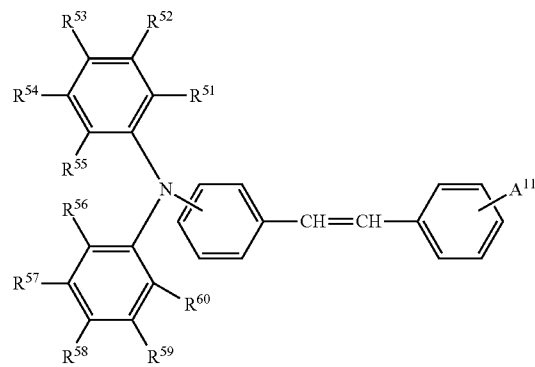

In the general formula (2), $R^{51}$ to $R^{60}$ each represent any one of a hydrogen atom, an alkyl group having 1 to 4 carbon atoms, and an aryl group having 6 to 15 carbon atoms. $A^{11}$ represents any one of substituents represented by the general formulas (1-1) to (1-3) below. The bonding position of a diphenylamino group and $A^{11}$ may be any of an ortho position, a meta position, and a para position with respect to a double bond of stilbene.

It is to be noted that a stilbene derivative represented by the general formula (2) is a substance limiting the general formula (1), and corresponds to a case where $Ar^1$ and $Ar^2$ in general formula (1) each represent an aryl group (for example, a phenyl group) having 6 carbon atoms.

(1-1)

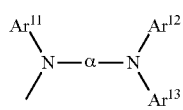

(1-2)

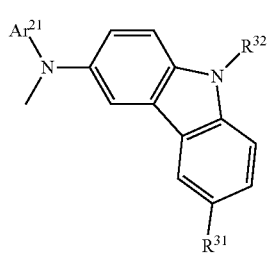

(1-3)

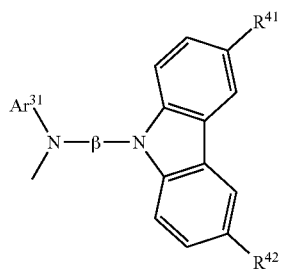

In the general formulas (1-1) to (1-3), $Ar^{11}$ to $Ar^{13}$ each represent an aryl group having 6 to 25 carbon atoms; a represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents any one of an alkyl group having 1 to 4 carbon atoms and an aryl group having 6 to 25 carbon atoms; $Ar^{31}$ represents an aryl group having 6 to 25 carbon atoms; β represents an arylene group having 6 to 25 carbon atoms; and $R^{41}$ and $R^{42}$ each represent any one of a hydrogen atom, an alkyl group having 1 to 4 carbon atoms, and an aryl group having 6 to 25 carbon atoms.

Another feature of a stilbene derivative of the present invention includes a structure shown in the following general formula (3).

(3)

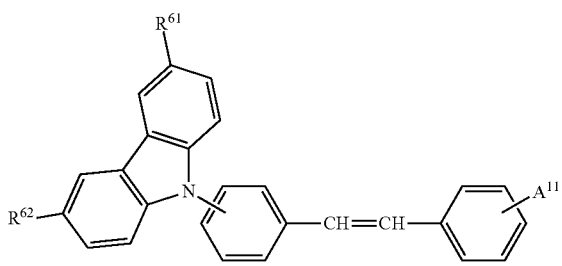

In the general formula (3), $R^{61}$ and $R^{62}$ each represent any one of a hydrogen atom, an alkyl group having 1 to 4 carbon atoms, and an aryl group having 6 to 25 carbon atoms. $A^{11}$ represents any one of substituents represented by the general formulas (1-1) to (1-3) below. The bonding positions of an N-carbazolyl group and $A^{11}$ may be any of an ortho position, a meta position, and a para position with respect to a double bond of stilbene.

It is to be noted that a stilbene derivative represented by the general formula (3) is a substance limiting a general formula (1), and corresponds to a case where $Ar^1$ and $Ar^2$ in the general formula (1) each represent an aryl group (for example, a phenyl group) having 6 carbon atoms and $Ar^1$ and $Ar^2$ form a 5-membered ring by being directly bonded to each other (for example, a carbazole group). In other words, the general formula (3) corresponds to a case where the diarylamino group (i.e., $NAr^1Ar^2$ unit) in general formula (1) is a carbazole (carbazolyl) group.

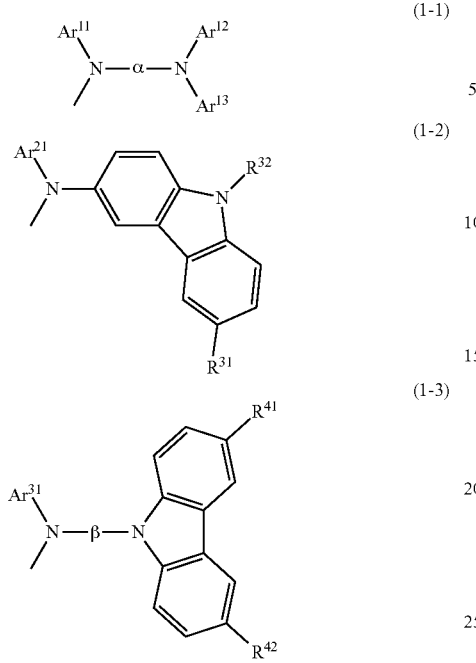

(1-1)

(1-2)

(1-3)

In the general formulas (1-1) to (1-3), $Ar^{11}$ to $Ar^{13}$ each represent an aryl group having 6 to 25 carbon atoms; α represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents any one of an alkyl group having 1 to 4 carbon atoms and an aryl group having 6 to 25 carbon atoms; $Ar^{31}$ represents an aryl group having 6 to 25 carbon atoms; β represents an arylene group having 6 to 25 carbon atoms; and $R^{41}$ and $R^{42}$ each represent any one of a hydrogen atom, an alkyl group having 1 to 4 carbon atoms, and an aryl group having 6 to 25 carbon atoms.

Another feature of a stilbene derivative of the present invention includes a structure shown in the following general formula (4).

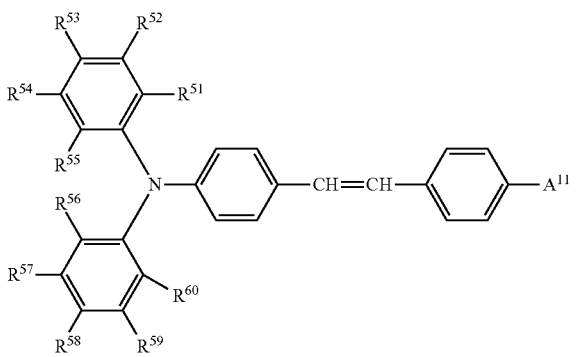

(4)

In the general formula (4), $R^{51}$ to $R^{60}$ each represent any one of a hydrogen atom, an alkyl group having 1 to 4 carbon atoms, and an aryl group having 6 to 15 carbon atoms. $A^{11}$ represents any one of substituents represented by the general formulas (1-1) to (1-3) below.

The general formula (4) is a formula further limiting the general formula (2) which limits the general formula (1), and the bonding position of $A^{11}$ and nitrogen in the general formula (2) is limited in the general formula (4).

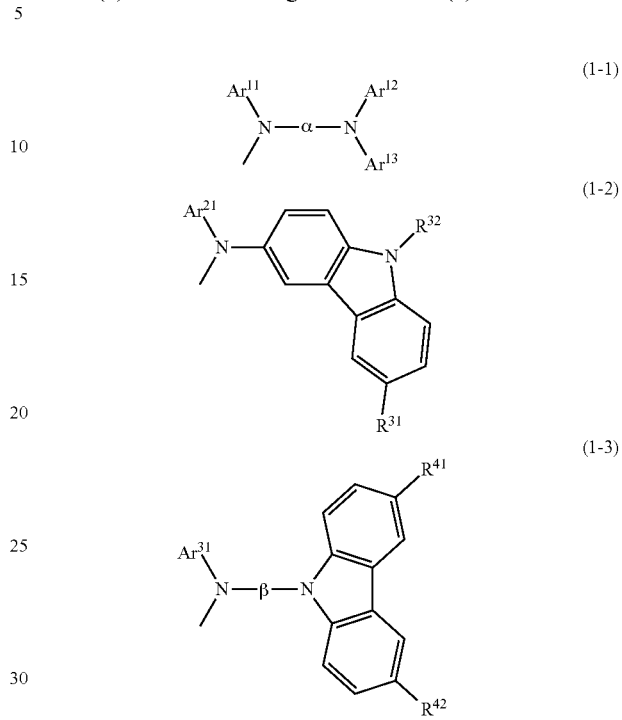

(1-1)

(1-2)

(1-3)

In the general formulas (1-1) to (1-3), $Ar^{11}$ to $Ar^{13}$ each represent an aryl group having 6 to 25 carbon atoms; α represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents any one of an alkyl group having 1 to 4 carbon atoms and an aryl group having 6 to 25 carbon atoms; $Ar^{31}$ represents an aryl group having 6 to 25 carbon atoms; β represents an arylene group having 6 to 25 carbon atoms; and $R^{41}$ and $R^{42}$ each represent any one of a hydrogen atom, an alkyl group having 1 to 4 carbon atoms, and an aryl group having 6 to 25 carbon atoms.

Another feature of a stilbene derivative of the present invention includes a structure shown in the following general formula (5).

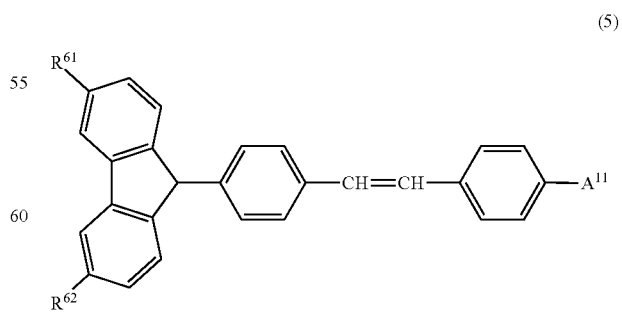

(5)

In the general formula (5), $R^{61}$ and $R^{62}$ each represent any one of a hydrogen atom, an alkyl group having 1 to 4 carbon atoms, and an aryl group having 6 to 25 carbon atoms. $A^{11}$ represents any one of substituents represented by the general formulas (1-1) to (1-3) below.

The general formula (5) is a formula further limiting the general formula (3) which limits the general formula (1), and the bonding position of $A^{11}$ and nitrogen in the general formula (3) is limited in the general formula (5).

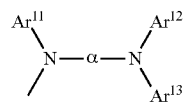
(1-1)

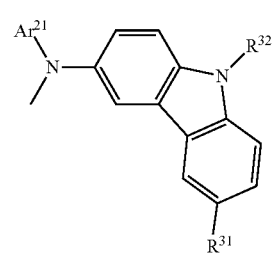
(1-2)

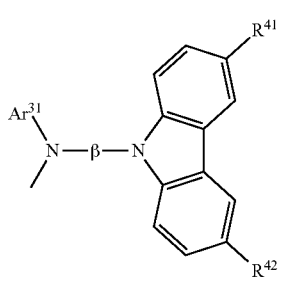
(1-3)

In the general formulas (1-1) to (1-3), $Ar^{11}$ to $Ar^{13}$ each represent an aryl group having 6 to 25 carbon atoms; α represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents any one of an alkyl group having 1 to 4 carbon atoms and an aryl group having 6 to 25 carbon atoms; $Ar^{31}$ represents an aryl group having 6 to 25 carbon atoms; β represents an arylene group having 6 to 25 carbon atoms; and $R^{41}$ and $R^{42}$ each represent any one of a hydrogen atom, an alkyl group having 1 to 4 carbon atoms, and an aryl group having 6 to 25 carbon atoms.

Another feature of a stilbene derivative of the present invention includes a structure shown in the following general formula (6).

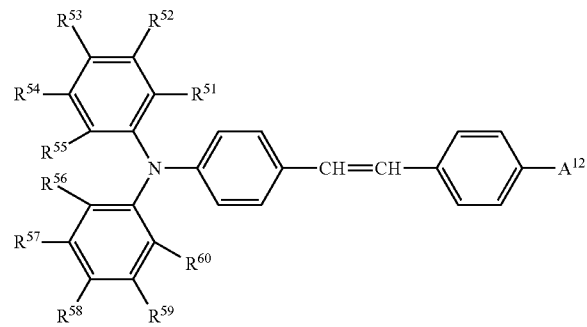
(6)

In the general formula (6), $R^{51}$ to $R^{60}$ each represent any one of a hydrogen atom, an alkyl group having 1 to 4 carbon atoms, and an aryl group having 6 to 15 carbon atoms. $A^{12}$ represents any one of substituents represented by the general formulas (2-1) to (2-3) below.

The general formula (6) is a formula limiting the general formula (1), similarly to the general formula (4). $A^{11}$ in the general formula (4) is replaced with $A^{12}$ in the general formula (6).

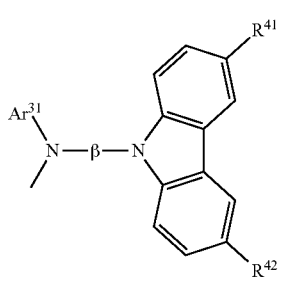
(2-1)

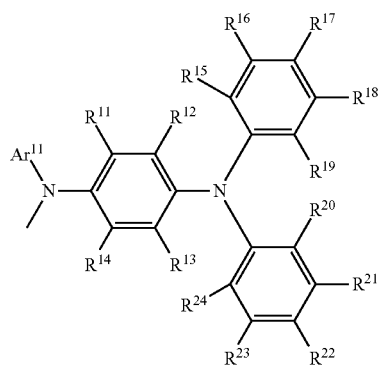
(2-2)

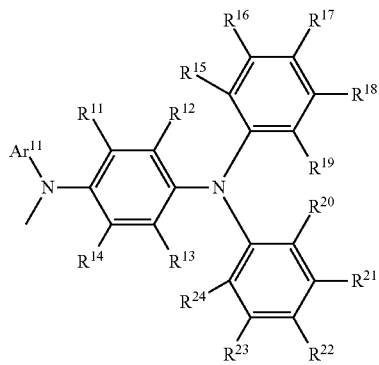

(2-1)

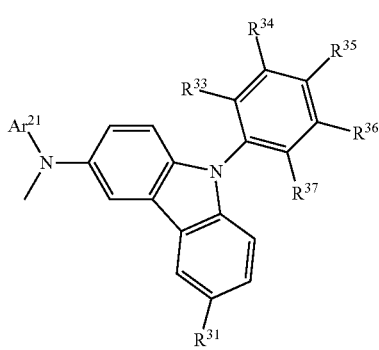

(2-2)

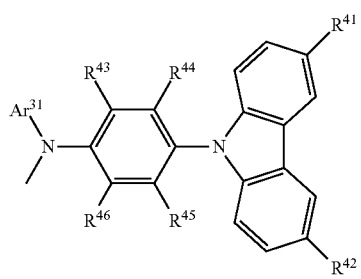

(2-3)

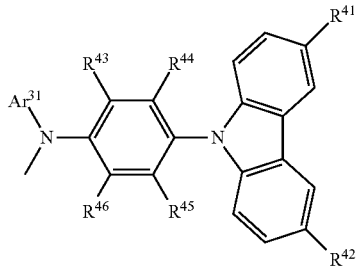

(2-3)

In the general formulas (2-1) to (2-3), $Ar^{11}$ represents an aryl group having 6 to 25 carbon atoms; $R^{11}$ to $R^{24}$ each represent any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{33}$ to $R^{37}$ each represent any one of a hydrogen atom, an alkyl group having 1 to 4 carbon atoms, and an aryl group having 6 to 15 carbon atoms; $Ar^{31}$ represents an aryl group having 6 to 25 carbon atoms; $R^{41}$ and $R^{42}$ each represent any one of a hydrogen atom, an alkyl group having 1 to 4 carbon atoms, and an aryl group having 6 to 25 carbon atoms; and $R^{43}$ to $R^{46}$ each represent any one of a hydrogen atom, an alkyl group having 1 to 4 carbon atoms, and an aryl group having 6 to 15 carbon atoms.

Another feature of a stilbene derivative of the present invention includes a structure shown in the following general formula (7).

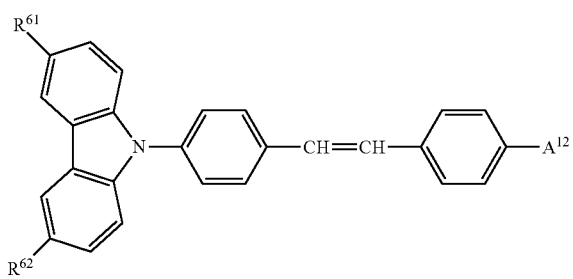

(7)

In the general formula (7), $R^{61}$ and $R^{62}$ each represent any one of a hydrogen atom, an alkyl group having 1 to 4 carbon atoms, and an aryl group having 6 to 25 carbon atoms. $A^{12}$ represents any one of substituents represented by the general formulas (2-1) to (2-3) below.

The general formula (7) is a formula limiting the general formula (1), similarly to the general formula (5). $A^{11}$ in the general formula (5) is replaced with $A^{12}$ in the general formula (7).

In the general formulas (2-1) to (2-3), $Ar^{11}$ represents an aryl group having 6 to 25 carbon atoms; $R^{11}$ to $R^{24}$ each represent any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{33}$ to $R^{37}$ each represent any one of a hydrogen atom, an alkyl group having 1 to 4 carbon atoms, and an aryl group having 6 to 15 carbon atoms; $Ar^{31}$ represents an aryl group having 6 to 25 carbon atoms; $R^{41}$ and $R^{42}$ each represent any one of a hydrogen atom, an alkyl group having 1 to 4 carbon atoms, and an aryl group having 6 to 25 carbon atoms; and $R^{43}$ to $R^{46}$ each represent any one of a hydrogen atom, an alkyl group having 1 to 4 carbon atoms, and an aryl group having 6 to 15 carbon atoms.

Another feature of a stilbene derivative of the present invention includes a structure shown in the following general formula (8).

(8)

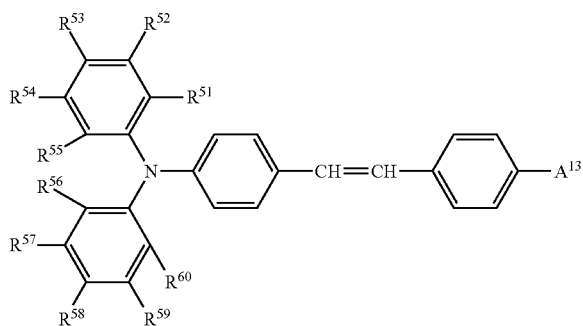

In the general formula (8), $R^{51}$ and $R^{60}$ each represent any one of a hydrogen atom, an alkyl group having 1 to 4 carbon atoms, and an aryl group having 6 to 15 carbon atoms. $A^{13}$ represents any one of substituents represented by the following general formulas (3-1) to (3-3).

(3-1)

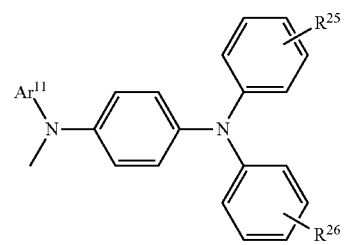

(3-2)

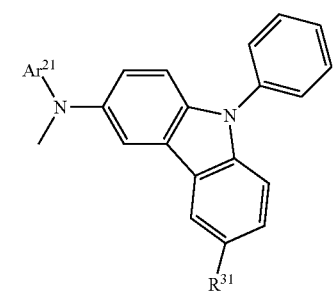

(3-3)

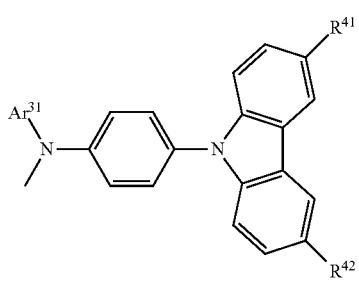

In the general formulas (3-1) to (3-3), $Ar^{11}$ represents an aryl group having 6 to 25 carbon atoms; $R^{25}$ and $R^{26}$ each represent any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $Ar^{31}$ represents an aryl group having 6 to 25 carbon atoms; and $R^{41}$ and $R^{42}$ each represent any one of a hydrogen atom, an alkyl group having 1 to 4 carbon atoms, and an aryl group having 6 to 25 carbon atoms.

Another feature of a stilbene derivative of the present invention includes a structure shown in the following general formula (9).

(9)

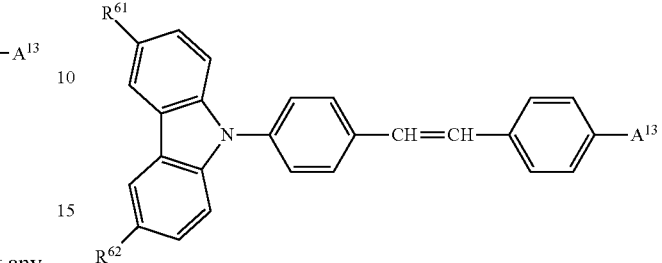

In the general formula (9), $R^{61}$ and $R^{62}$ each represent any one of a hydrogen atom, an alkyl group having 1 to 4 carbon atoms, and an aryl group having 6 to 25 carbon atoms. $A^{13}$ represents any one of substituents represented by the following general formulas (3-1) to (3-3).

(3-1)

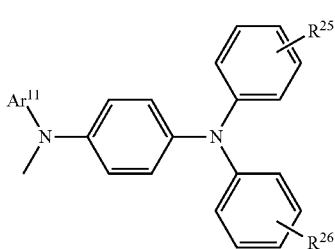

(3-2)

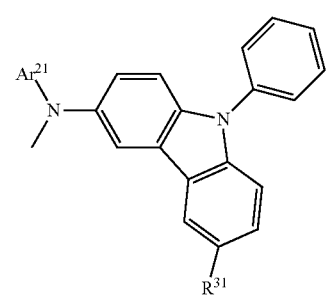

(3-3)

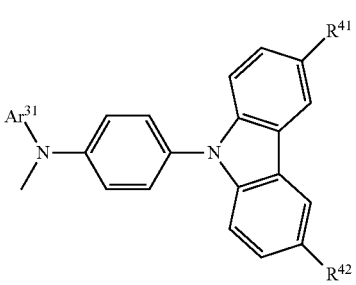

In the general formulas (3-1) to (3-3), $Ar^{11}$ represents an aryl group having 6 to 25 carbon atoms; $R^{25}$ and $R^{26}$ each represent any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $Ar^{31}$ represents an aryl group having 6 to 25 carbon atoms; and $R^{41}$ and $R^{42}$ each represent any one of a hydrogen atom, an alkyl group having 1 to 4 carbon atoms, and an aryl group having 6 to 25 carbon atoms.

One feature of a light-emitting element of the present invention is to have the stilbene derivative according to any one of the general formulas (1) to (9) for a light-emitting layer between a pair of electrodes.

Another feature of a light-emitting element of the present invention is to have the stilbene derivative according to any one of the general formulas (1) to (9) for a part of a light-emitting layer between a pair of electrodes.

One feature of a display device of the present invention is to have the above-mentioned light-emitting element in a pixel portion.

One feature of an electronic device of the present invention is that the display device mentioned above is used for a display portion.

By using a novel stilbene derivative of the present invention, blue-emissive light-emitting element with excellent color purity can be provided. Further, by using the light-emitting element of the present invention for the display portion, a display device and an electronic device which are excellent in color reproducibility can be provided.

DETAILED DESCRIPTION OF THE INVENTION

Figure 1:
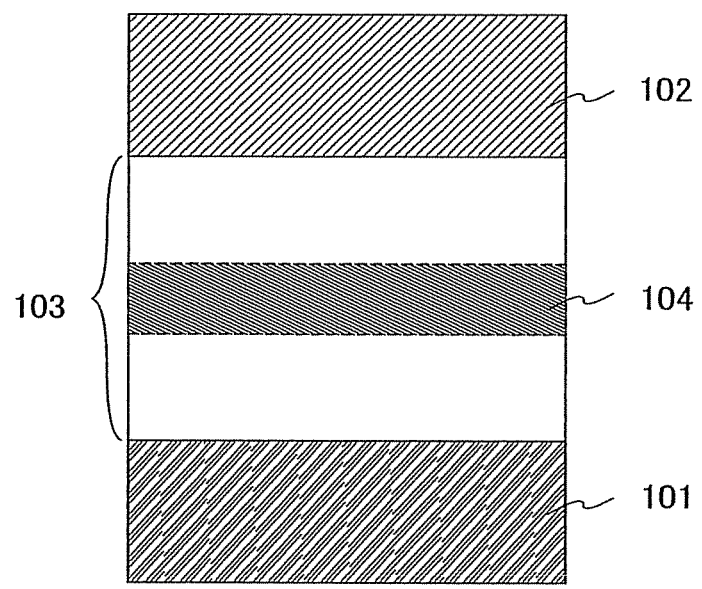
FIG. 1 shows a light-emitting element of the present invention.

Embodiment Modes of the present invention will be described below with reference to the accompanying drawings. However, the present invention is not limited to the description given below, and it will be readily apparent to those skilled in the art that various changes and modifications in modes and details thereof can be made without departing from the purpose and scope of the present invention. Therefore, the present invention should not be interpreted as being limited to the description of the embodiment modes given below. It is to be noted that in embodiments of the present invention which are described below, like reference numerals are used for like portions throughout the drawings and chemical formulas.

Embodiment Mode 1

One feature of a stilbene derivative of the present invention includes a structure represented by the following general formula (1).

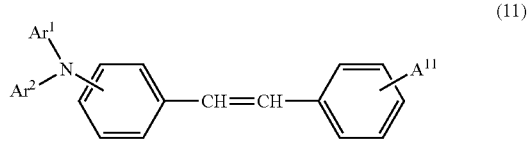

(11)

In the general formula (1), $Ar^1$ and $Ar^2$ each represent an aryl group having 6 to 25 carbon atoms, and the aryl group may include an alkyl group having 1 to 4 carbon atoms. $Ar^1$ and $Ar^2$ may form a 5-membered ring by being directly bonded to each other. That is, the general formula (2) below shows one mode of a case where $Ar^1$ and $Ar^2$ are not directly bonded to each other, and the general formula (3) below shows one mode of a case where $Ar^1$ and $Ar^2$ form a 5-membered ring (for example, a carbazole group) by being directly bonded to each other.

It is to be noted that "carbon atoms" in "an aryl group having 6 to 25 carbon atoms" relating to "$Ar^1$ and $Ar^2$" and the like in the general formula (1) are carbon atoms which form an aromatic ring, and carbon atoms of a substituent bonded to the aromatic ring are not included therein. That is, "an aryl group having 6 to 25 carbon atoms" which corresponds to "$Ar^1$ and $Ar^2$" and the like is exemplified in the formulas (21-1) to (21-9) below, and, for example, the formula (21-1) represents an aryl group having 6 carbon atoms, and the formula (21-5) represents an aryl group having 10 carbon atoms. The formula (21-7) having two methyl groups and a methylene group bonded to the two methyl groups as substituents represents an aryl group having 12 carbon atoms, and carbons of the two methyl groups and the methylene group bonded to the two methyl groups are not included in carbons of the aryl group.

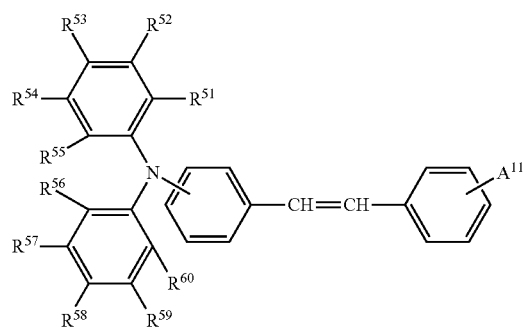

(2)

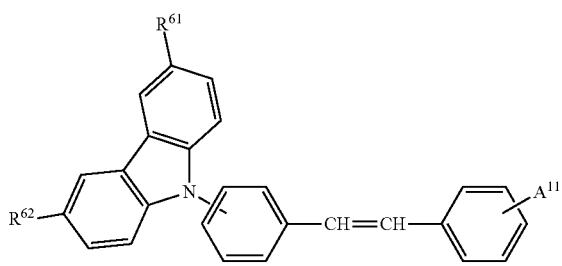

(3)

In the general formula (2), $R^{51}$ to $R^{60}$ each represent any one of a hydrogen atom, an alkyl group having 1 to 4 carbon atoms, and an aryl group having 6 to 15 carbon atoms. In the general formula (3), $R^{61}$ and $R^{62}$ each represent any one of a hydrogen atom, an alkyl group having 1 to 4 carbon atoms, and an aryl group having 6 to 25 carbon atoms.

In each of the general formulas (1) to (3), $A^{11}$ represents any one of substituents represented by the following general formulas (1-1) to (1-3).

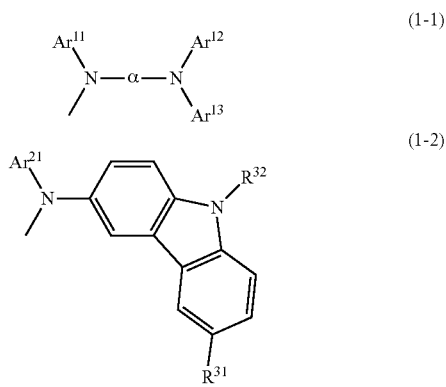

(1-1)

(1-2)

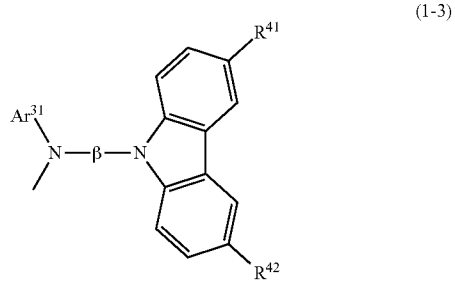

(1-3)

In the general formulas (1-1) to (1-3), $Ar^{11}$ to $Ar^{13}$ each represent an aryl group having 6 to 25 carbon atoms; a represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents any one of an alkyl group having 1 to 4 carbon atoms and an aryl group having 6 to 25 carbon atoms; $Ar^{31}$ represents an aryl group having 6 to 25 carbon atoms; β represents an arylene group having 6 to 25 carbon atoms; and $R^{41}$ and $R^{42}$ each represent any one of a hydrogen atom, an alkyl group having 1 to 4 carbon atoms, and an aryl group having 6 to 25 carbon atoms.

It is to be noted that, as explained above, carbon atoms of the arylene group are the same as in the case of the aryl group.

The bonding position of $A^{11}$ may be any of an ortho position, a meta position, and a para position with respect to the double bond of stilbene. For example, a case where a bonding position of $A^{11}$ is a para position with respect to the double bond of stilbene in general formulas (2) and (3) is represented by general formulas (4) and (5) below. A light-emitting element in which a stilbene derivative having $A^{11}$ at a para position with respect to the double bond of stilbene, as shown in general formulas (4) and (5), is used for a light-emitting layer or a part of a light-emitting layer has high quantum efficiency. Therefore, a light-emitting element which uses a stilbene derivative having $A^{11}$ at a para position is preferable since the light-emitting element can be driven at lower current density compared with a case where $A^{11}$ is bonded at an ortho position or a meta position.

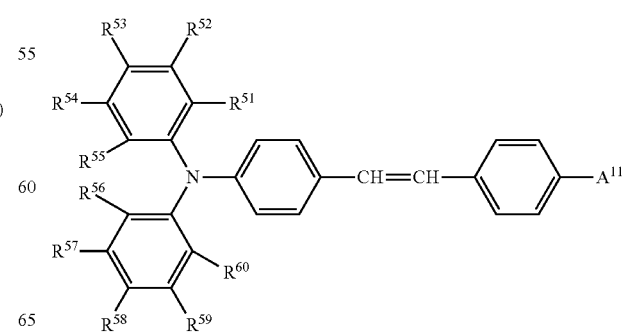

(4)

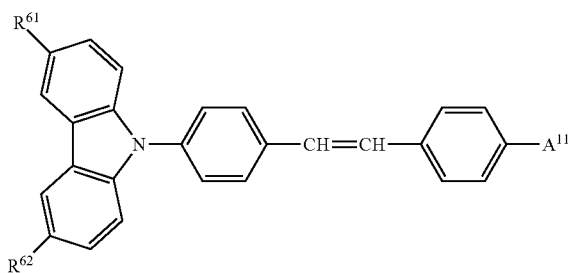

(5)

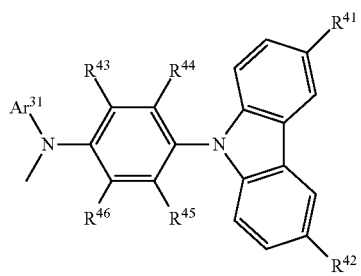

(2-3)

As modes of general formulas (1-1) to (1-3), the general formulas (2-1) to (2-3) are respectively given. In the general formulas (2-1) to (2-3), $Ar^{11}$ represents an aryl group having 6 to 25 carbon atoms; $R^{11}$ to $R^{24}$ each represent any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{33}$ to $R^{37}$ each represent any one of a hydrogen atom, an alkyl group having 1 to 4 carbon atoms, and an aryl group having 6 to 15 carbon atoms; $Ar^{31}$ represents an aryl group having 6 to 25 carbon atoms; $R^{41}$ and $R^{42}$ each represent any one of a hydrogen atom, an alkyl group having 1 to 4 carbon atoms, and an aryl group having 6 to 25 carbon atoms; and $R^{43}$ to $R^{46}$ each represent any one of a hydrogen atom, an alkyl group having 1 to 4 carbon atoms, and an aryl group having 6 to 15 carbon atoms.

The general formulas (3-1) to (3-3) below can be given as modes limiting general formulas (1-1) to (1-3), respectively. In the general formulas (3-1) to (3-3), $Ar^{11}$ represents an aryl group having 6 to 25 carbon atoms; $R^{25}$ and $R^{26}$ each represent any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $Ar^{31}$ represents an aryl group having 6 to 25 carbon atoms; and $R^{41}$ and $R^{42}$ each represent any one of a hydrogen atom, an alkyl group having 1 to 4 carbon atoms, and an aryl group having 6 to 25 carbon atoms.

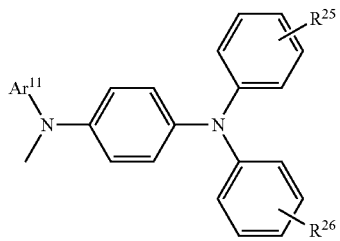

(3-1)

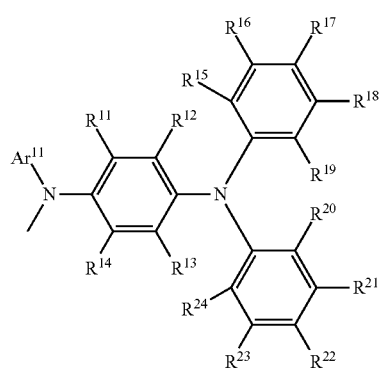

(2-1)

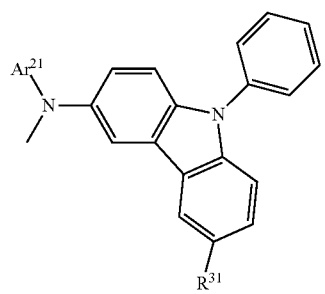

(3-2)

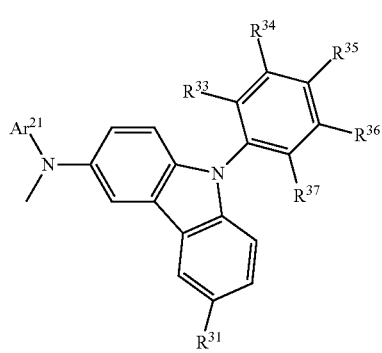

(2-2)

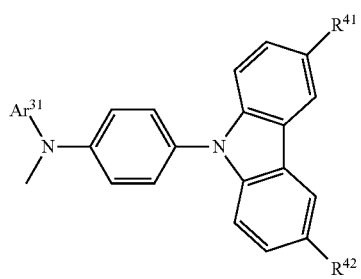

(3-3)

As specific modes of $Ar^{11}$ to $Ar^{13}$ in the general formula (1-1), the following formulas (21-1) to (21-9) can be given.

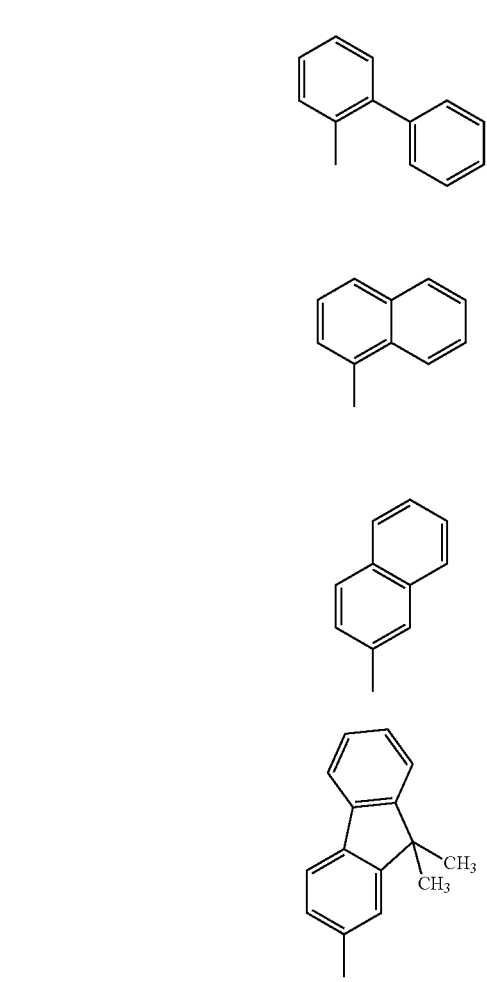
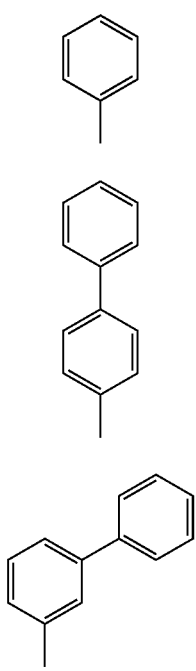
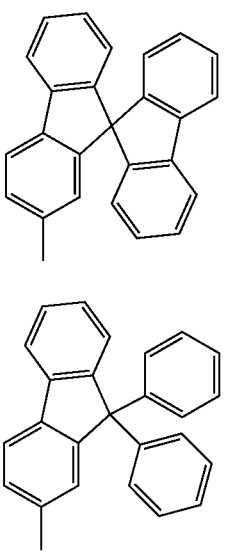
As specific modes of α in the general formula (1-1), the following formulas (22-1) to (22-9) can be given.
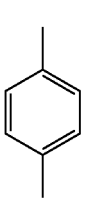

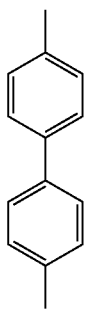 (22-6)
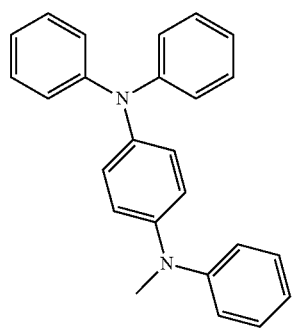 (31-1)
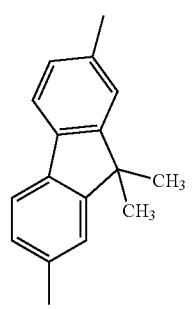 (22-7)
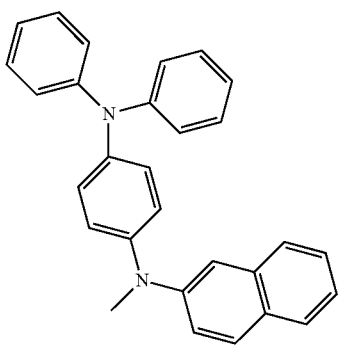 (31-2)
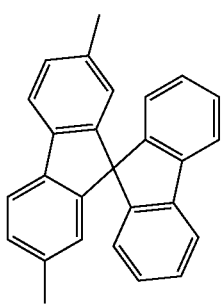 (22-8)
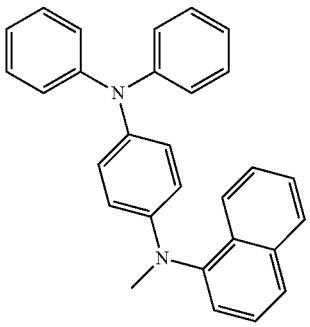 (31-3)
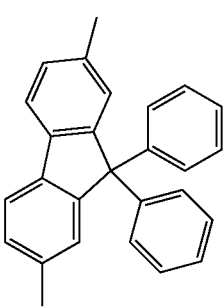 (22-9)
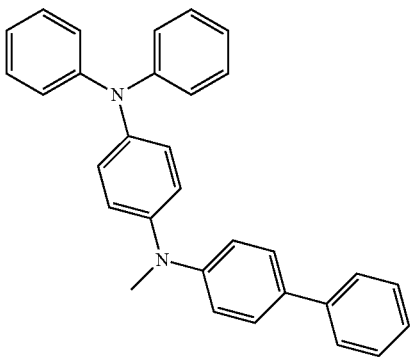 (31-4)
As specific examples of the general formula (1-1), the following formulas (31-1) to (31-23) can be given.

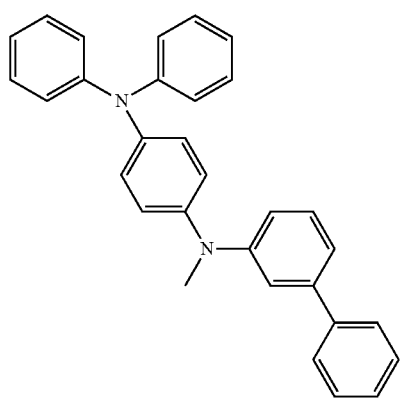
(31-5)
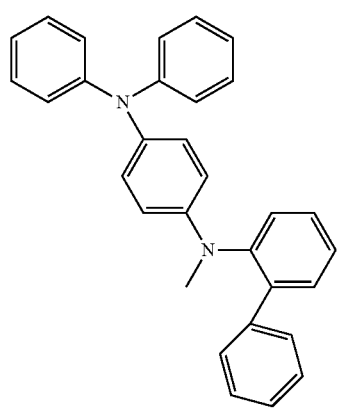
(31-6)
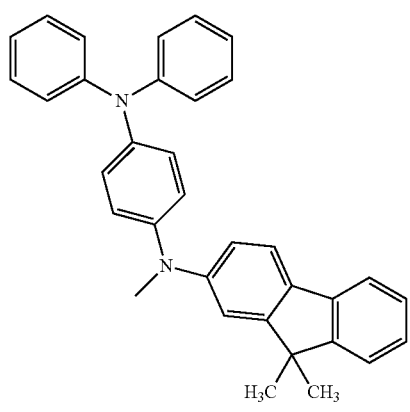
(31-7)
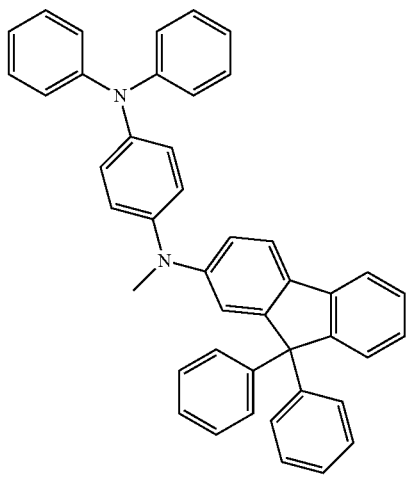
(31-8)
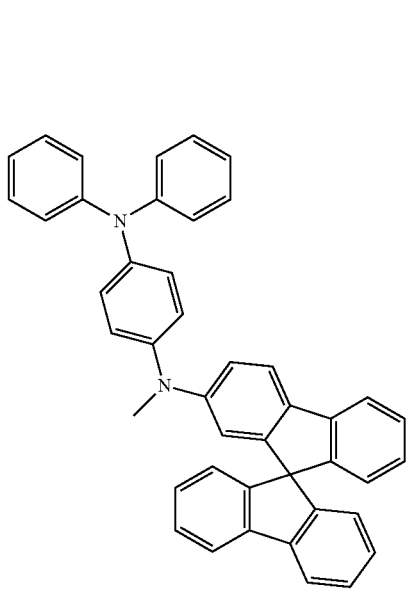
(31-9)
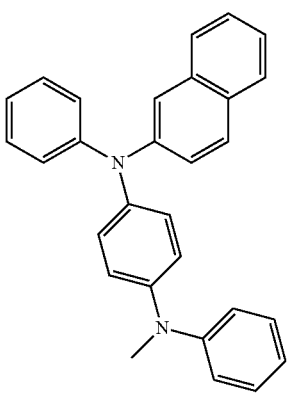
(31-10)

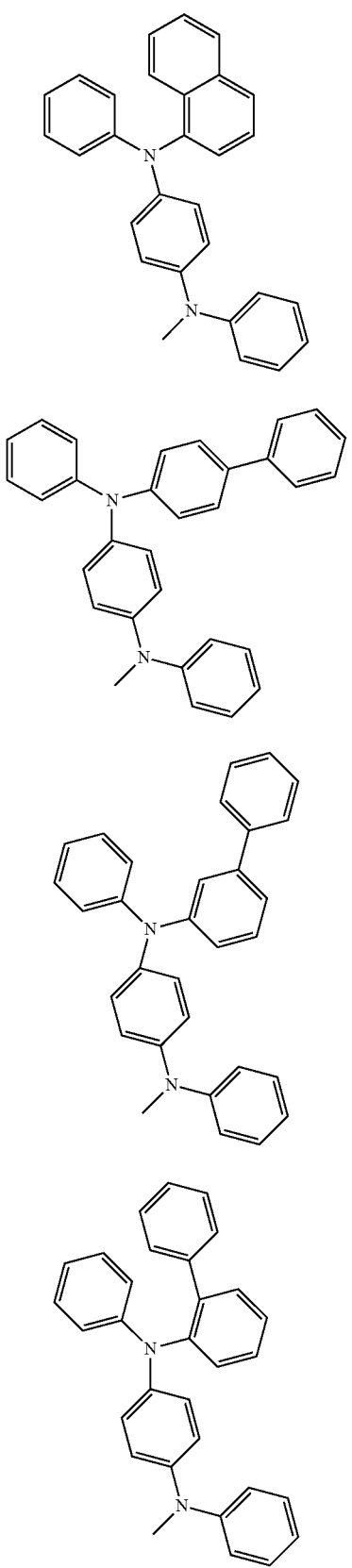
(31-11)
(31-12)
(31-13)
(31-14)
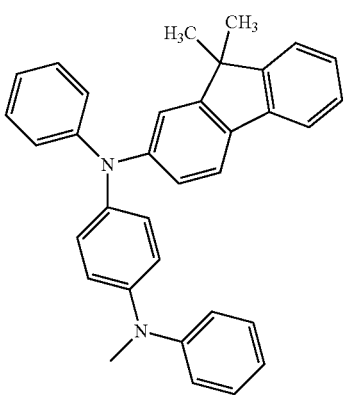
(31-15)
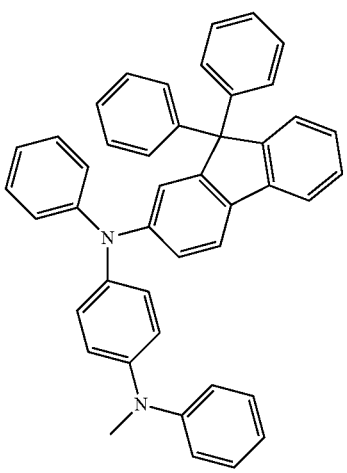
(31-16)
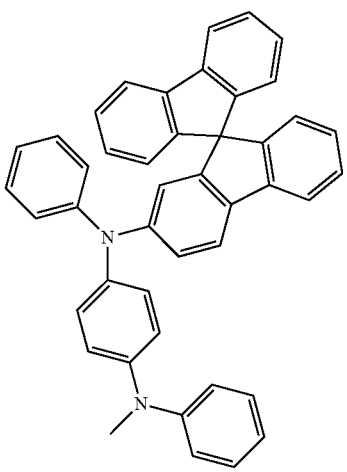
(31-17)

(31-18)
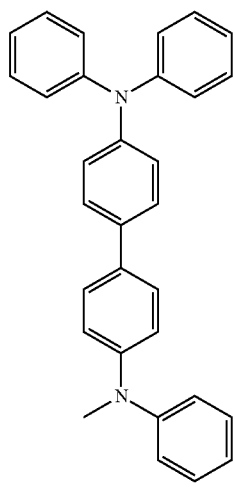
(31-19)
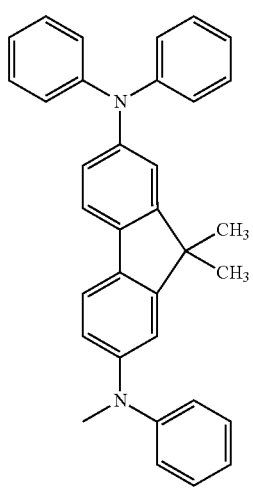
(31-20)
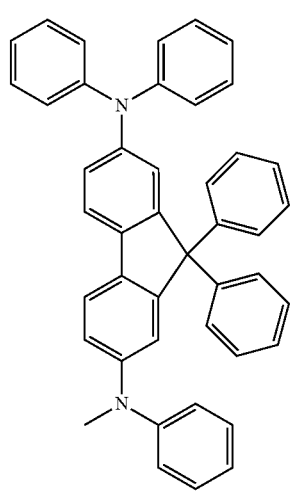
(31-21)
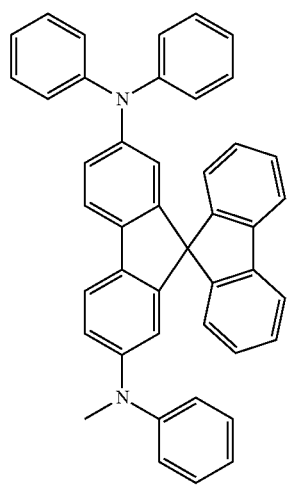
(31-22)
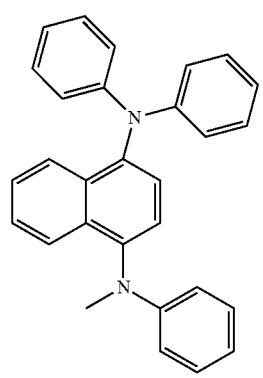
(31-23)
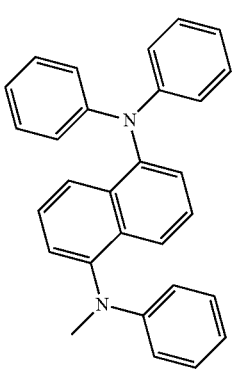
As specific modes of $Ar^{21}$ in the general formula (1-2), the following formulas (23-1) to (23-9) can be given.
(23-1)
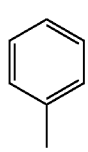

(23-2) 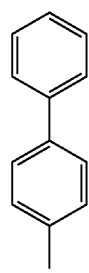
(23-3) 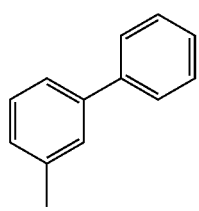
(23-4) 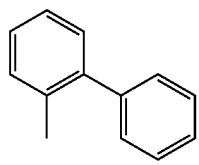
(23-5) 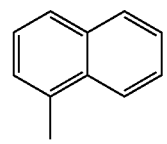
(23-6) 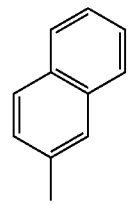
(23-7) 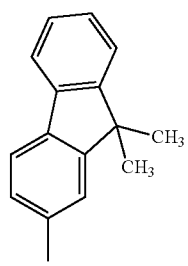
(23-8) 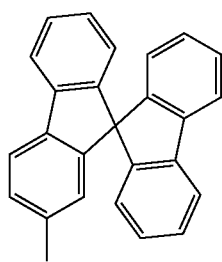
(23-9) 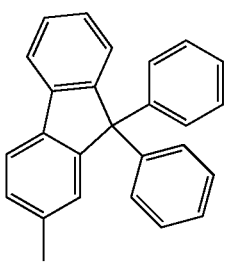
As specific modes of $R^{31}$ in the general formula (1-2), the following formulas (24-1) to (24-18) can be given.
(24-1) 
(24-2) 
(24-3) 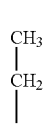
(24-4) 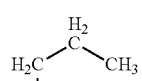
(24-5) 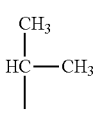
(24-6) 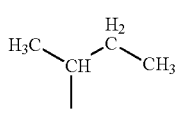
(24-7) 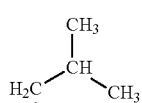
(24-8) 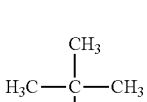
(24-9) 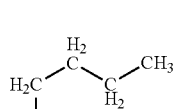
(24-10) 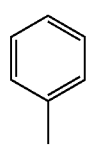

(24-11) 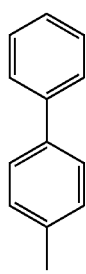
(24-12) 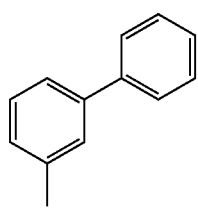
(24-13) 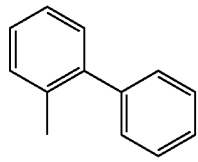
(24-14) 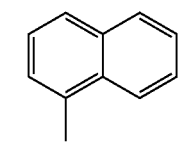
(24-15) 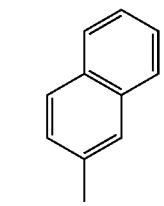
(24-16) 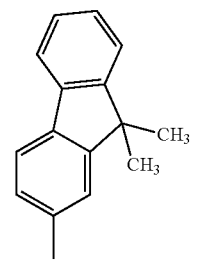
(24-17) 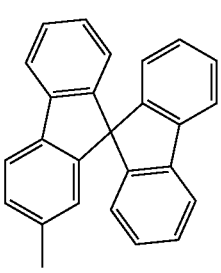
(24-18) 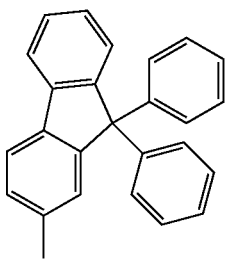
As specific modes of $R^{32}$ in the general formula (1-2), the following formulas (25-1) to (25-17) can be given.
(25-1) 
(25-2) 
(25-3) 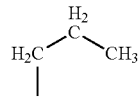
(25-4) 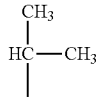
(25-5) 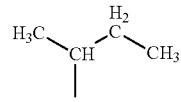
(25-6) 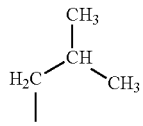
(25-7) 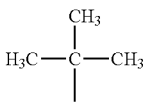
(25-8) 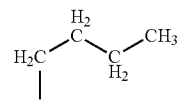
(25-9) 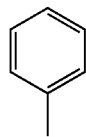

(25-10) 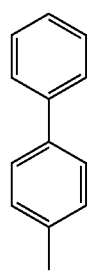
(25-11) 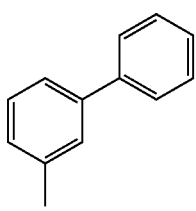
(25-12) 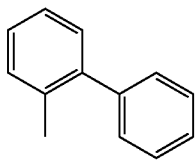
(25-13) 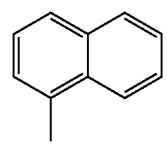
(25-14) 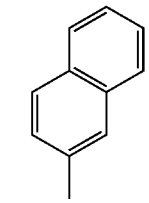
(25-15) 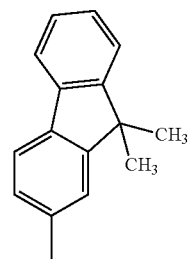
(25-16) 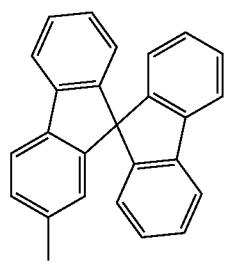
(25-17) 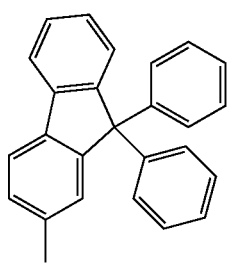
As specific examples of the general formula (1-2), the following formulas (32-1) to (32-42) can be given.
(32-1) 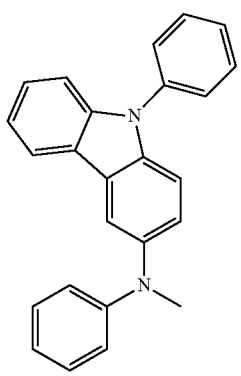
(32-2) 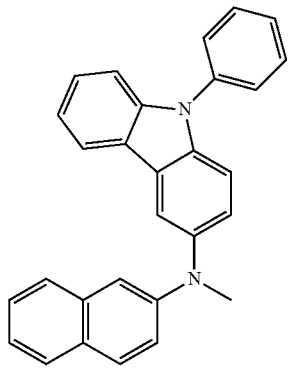
(32-3) 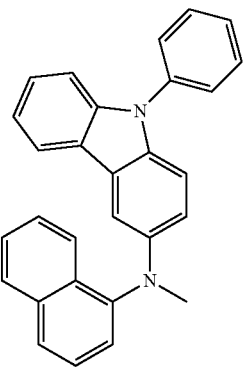

(32-4)
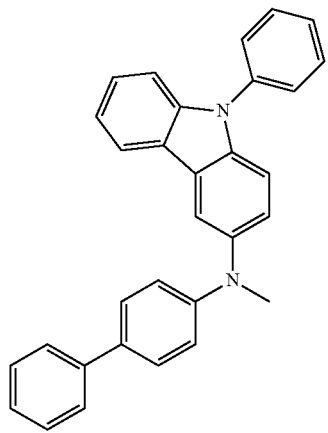
(32-5)
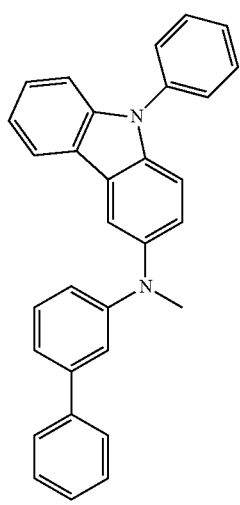
(32-6)
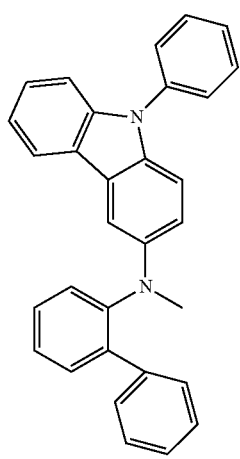
(32-7)
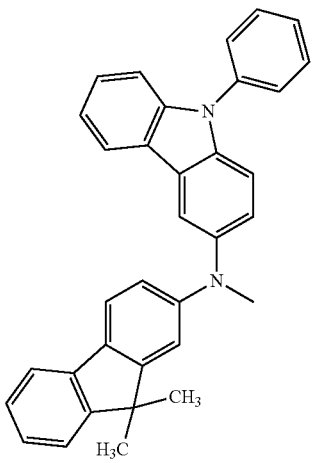
(32-8)
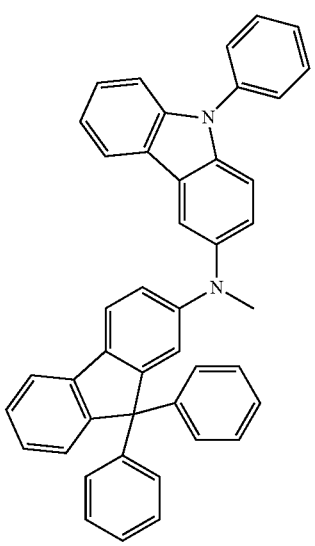
(32-9)
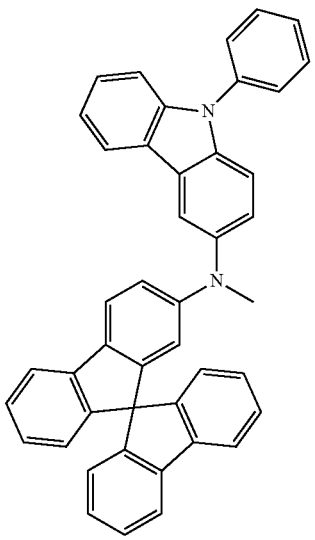

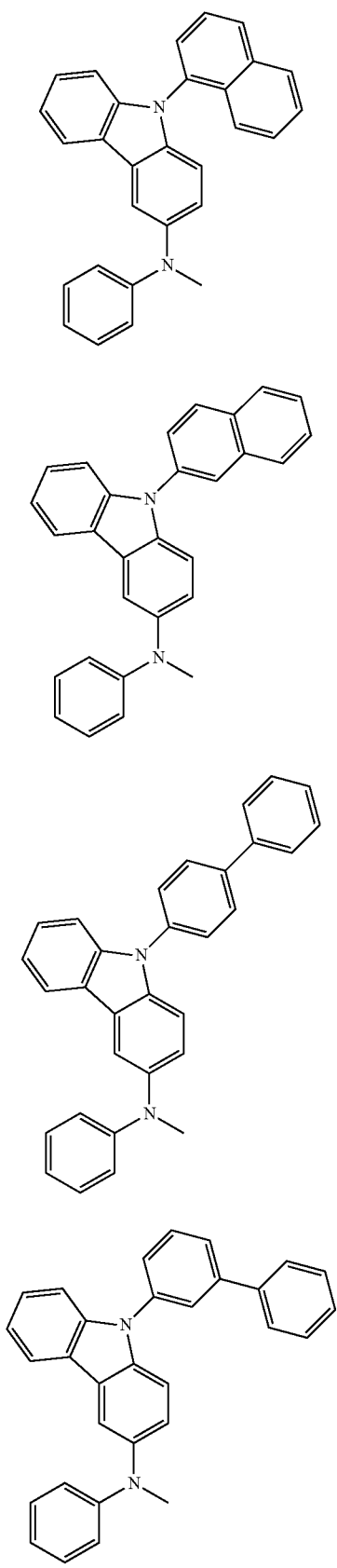
(32-10)
(32-11)
(32-12)
(32-13)
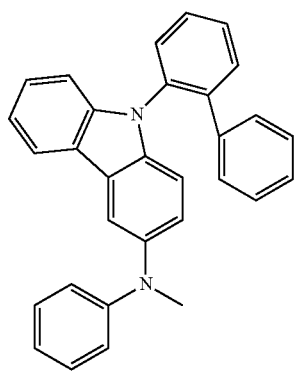
(32-14)
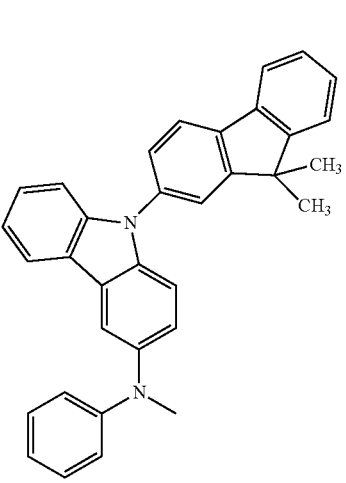
(32-15)
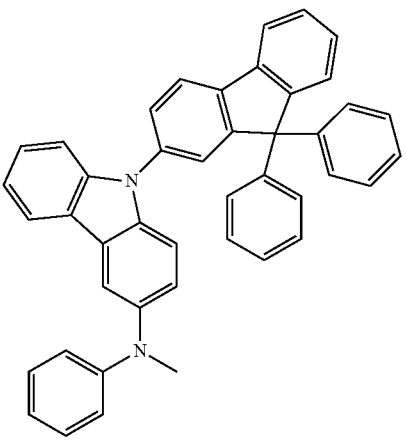
(32-16)

-continued
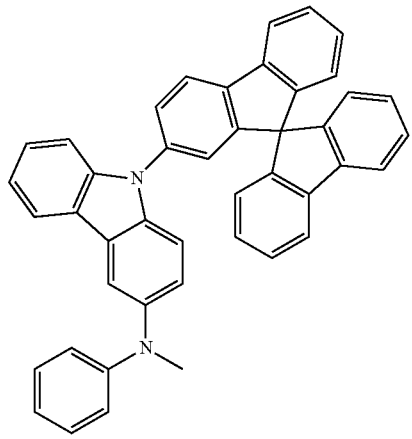 (32-17)
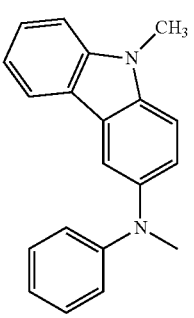 (32-18)
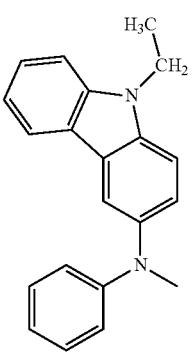 (32-19)
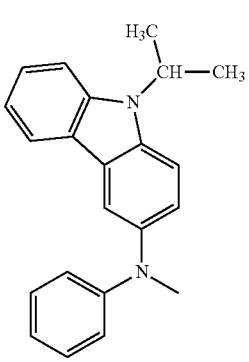 (32-20)
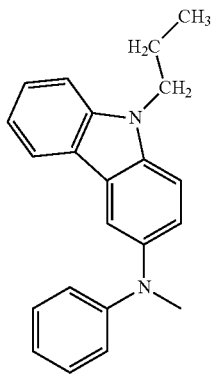 (32-21)
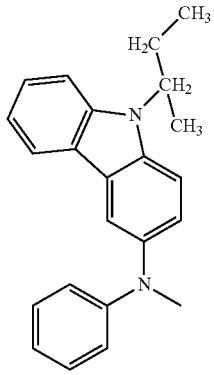 (32-22)
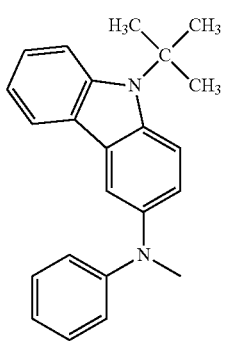 (32-23)
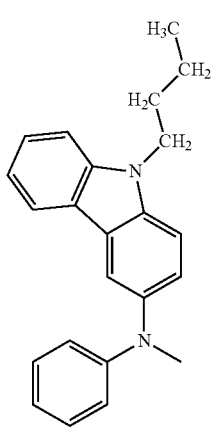 (32-24)

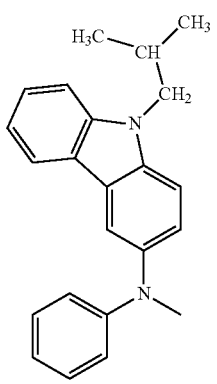 (32-25)
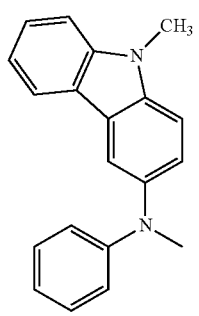 (32-18)
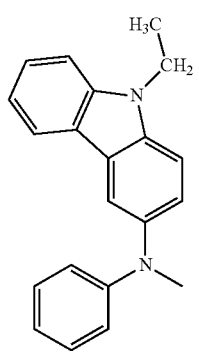 (32-19)
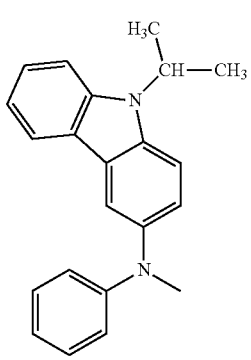 (32-20)
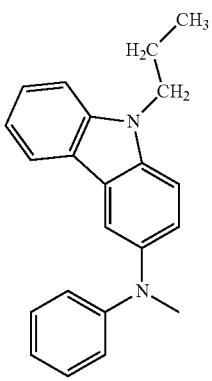 (32-21)
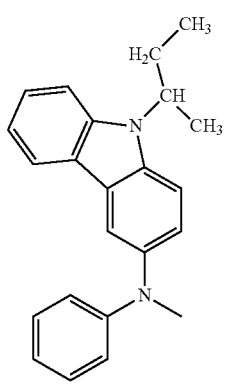 (32-22)
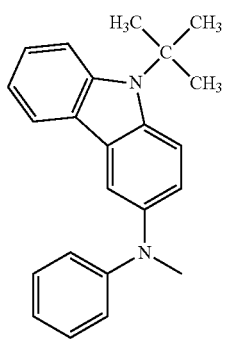 (32-23)
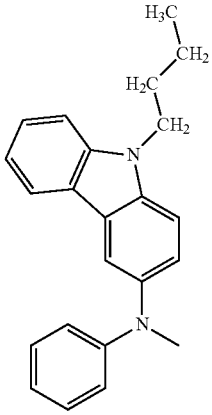 (32-24)

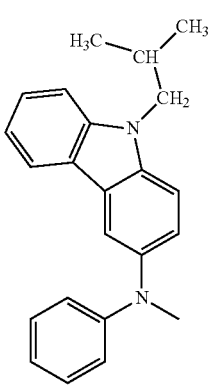
(32-25)
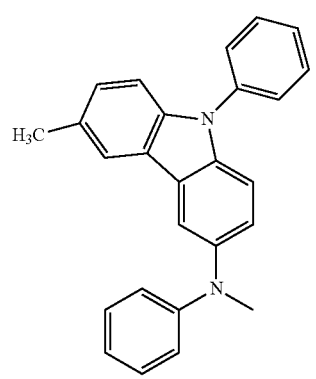
(32-32)
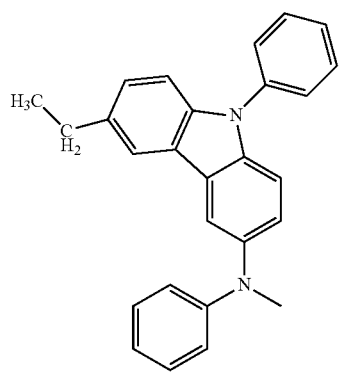
(32-33)
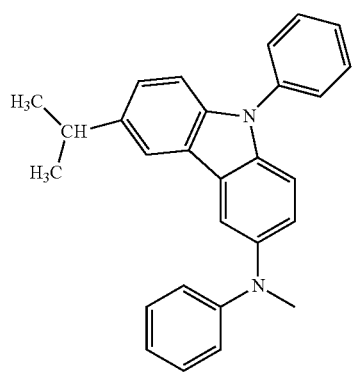
(32-34)
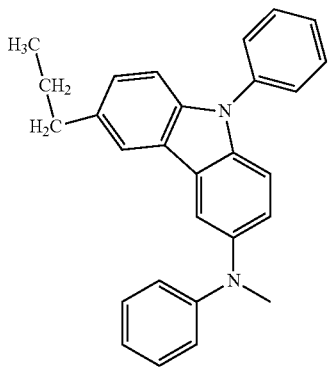
(32-35)
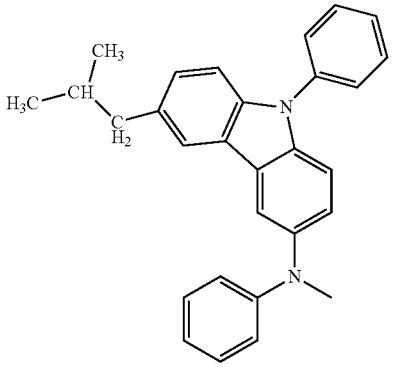
(32-36)
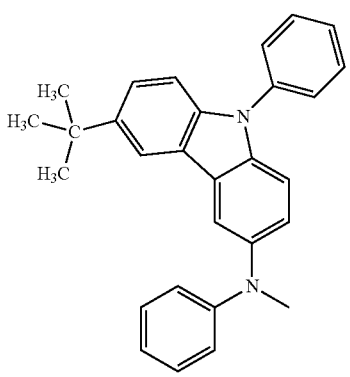
(32-37)
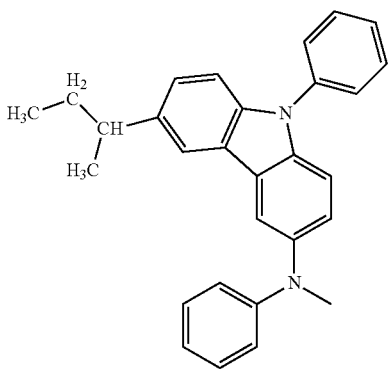
(32-38)

As specific modes of $A^{31}$ in the general formula (1-3), the following formulas (26-1) to (26-9) can be given.

(26-8)
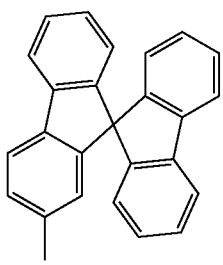
(26-9)
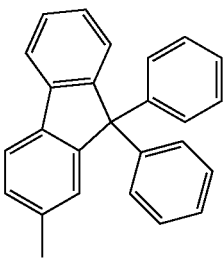
As specific modes of β in the general formula (1-3), the following formulas (27-1) to (27-9) can be given.
(27-1)
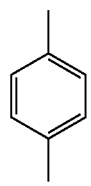
(27-2)
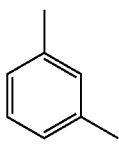
(27-3)
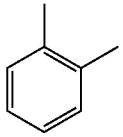
(27-4)
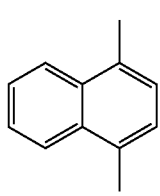
(27-5)
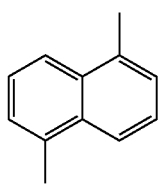
(27-6)
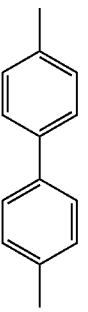
(27-7)
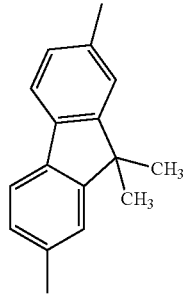
(27-8)
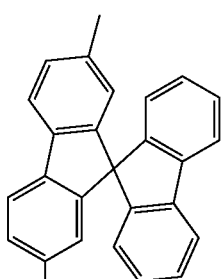
(27-9)
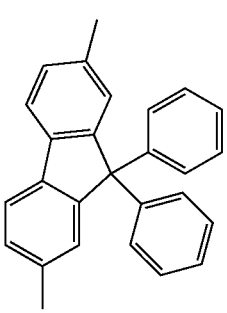
As specific modes of $R^{41}$ and $R^{42}$ in the general formula (1-3), the following formulas (28-1) to (28-18) can be respectively given.
(28-1)
H
(28-2)
$CH_3$
(28-3)
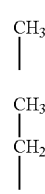
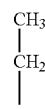

-continued
(28-4) 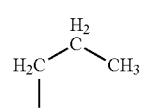
(28-5) 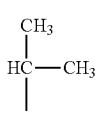
(28-6) 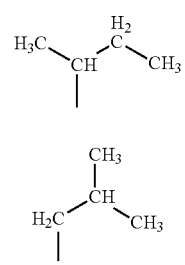
(28-7)
(28-8)
(28-9) 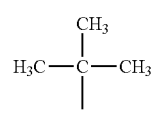
(28-10) 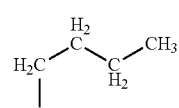
(28-11) 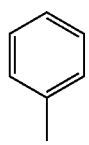
(28-12) 
(28-13) 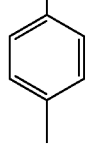
-continued
(28-14) 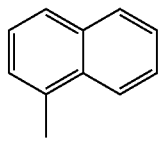
(28-15) 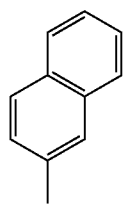
(28-16) 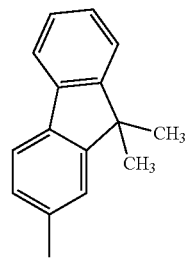
(28-17) 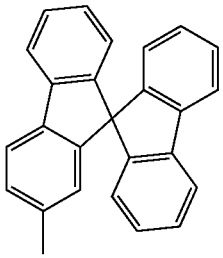
(28-18) 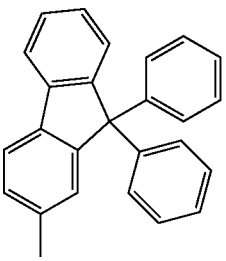
As specific examples of the general formula (1-3), the following formulas (33-1) to (33-34) can be given.

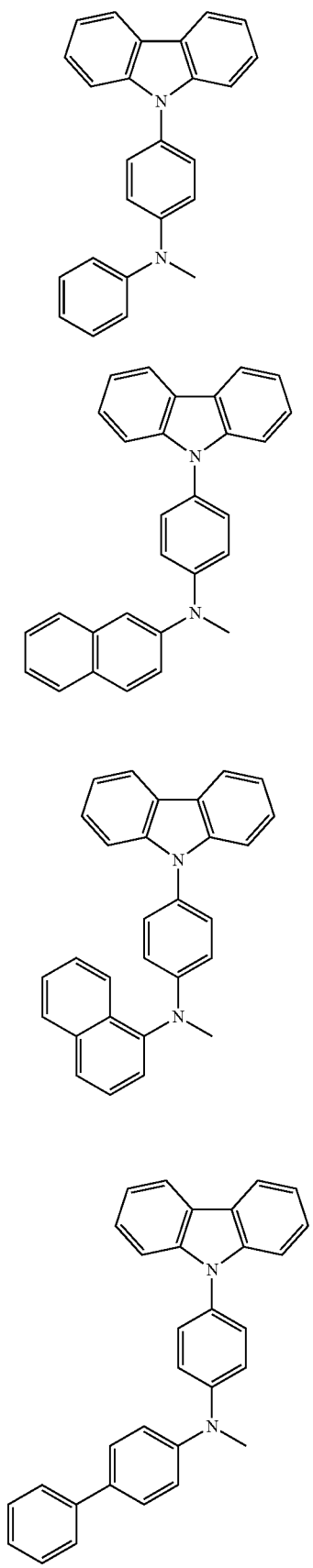
(33-1)
(33-2)
(33-3)
(33-4)
-continued
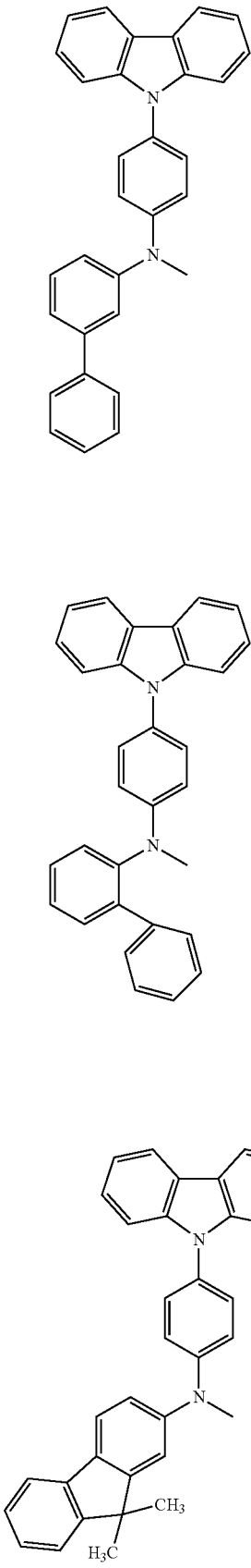
(33-5)
(33-6)
(33-7)

(33-8)
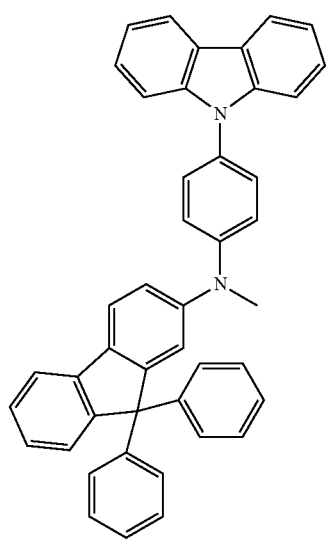
(33-9)
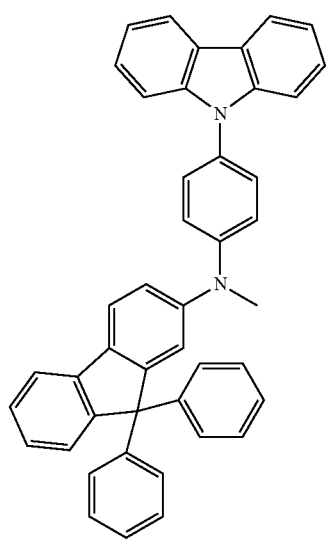
(33-1)
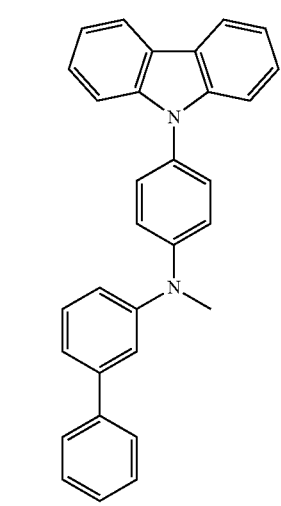
(33-2)
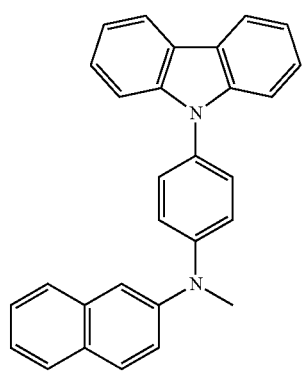
(33-3)
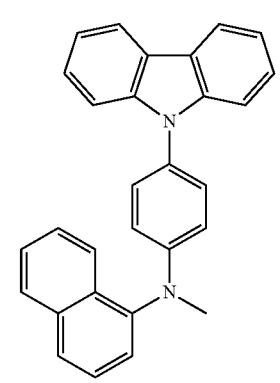
(33-4)
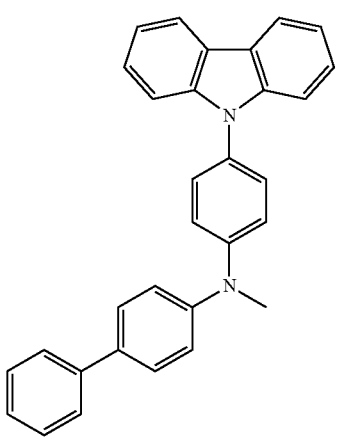
(33-5)
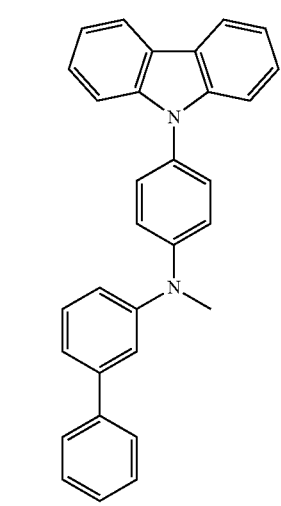

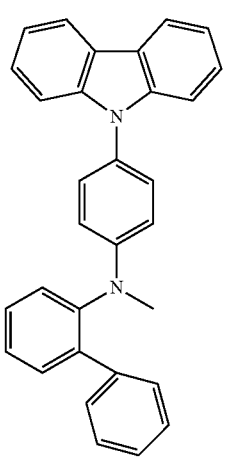
(33-6)
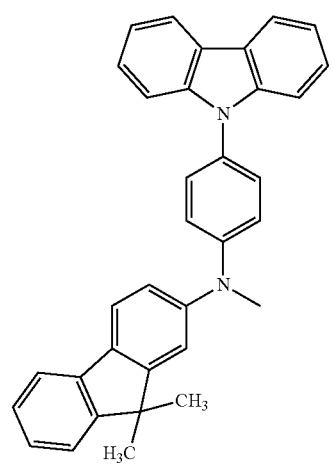
(33-7)
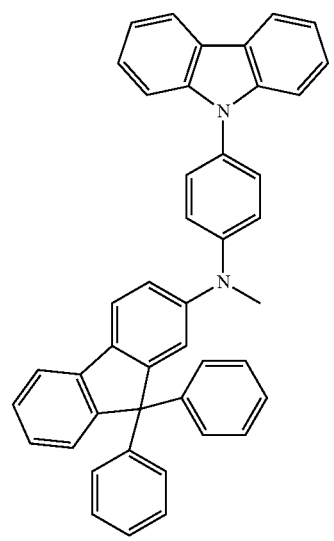
(33-8)
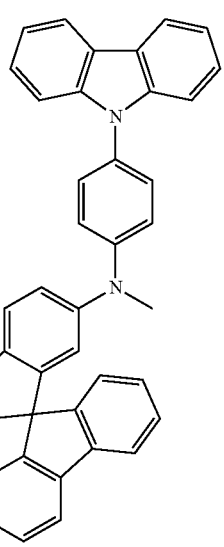
(33-9)
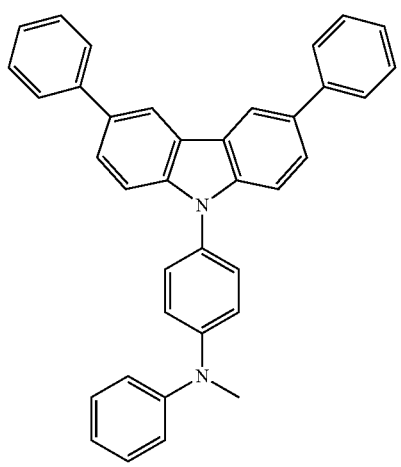
(33-18)
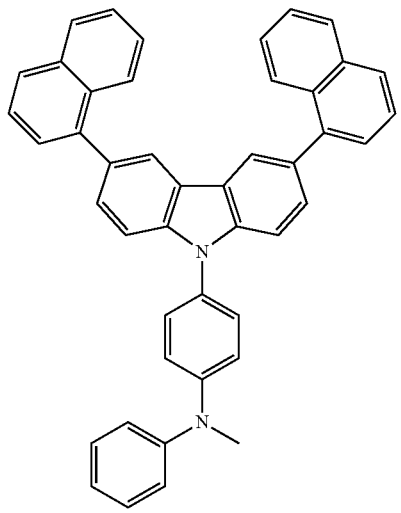
(33-19)

(33-20)
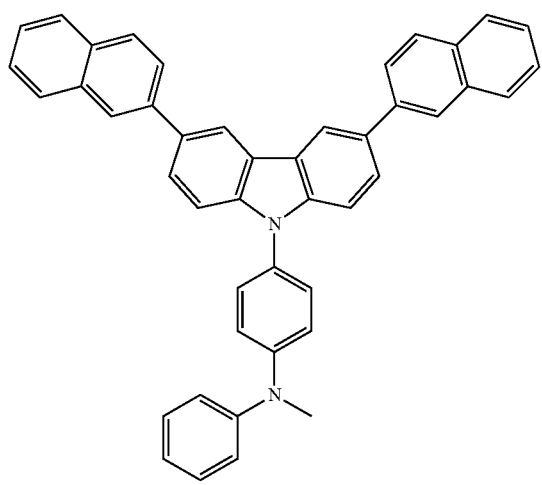
(33-23)
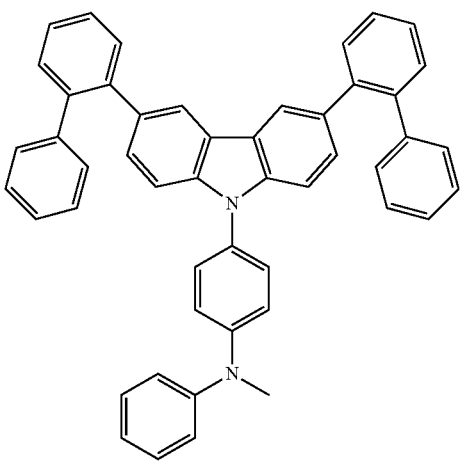
(33-21)
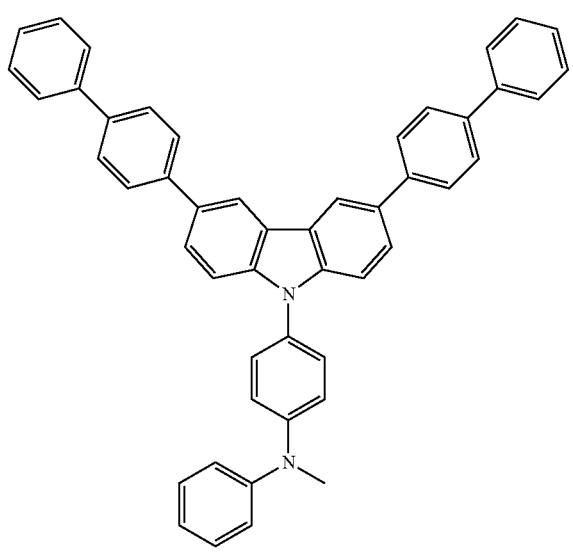
(33-24)
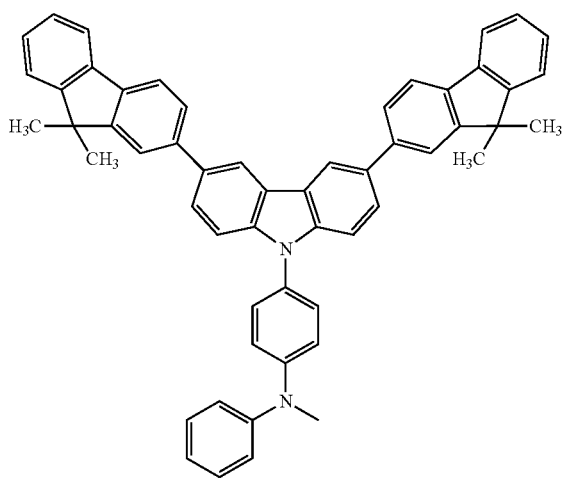
(33-22)
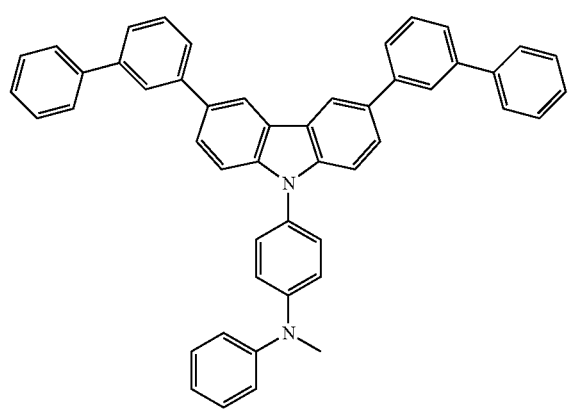
(33-25)
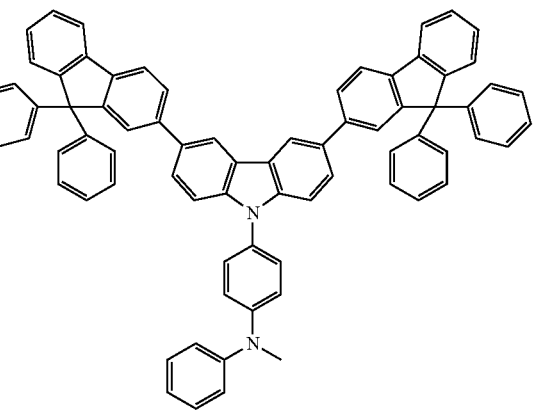

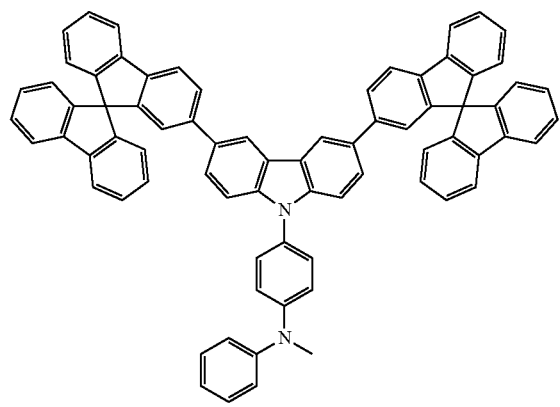
(33-26)
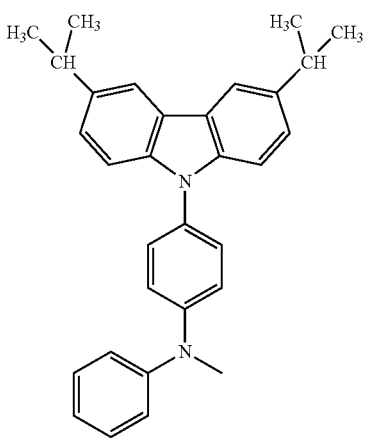
(33-29)
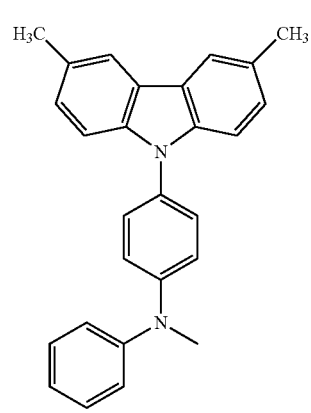
(33-27)
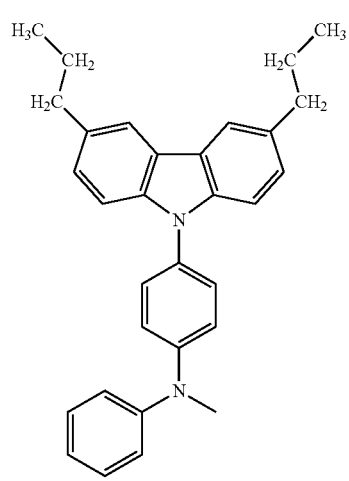
(33-30)
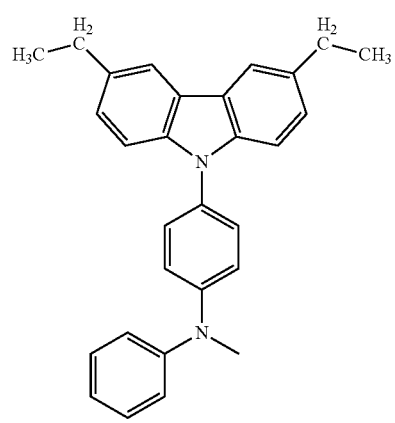
(33-28)
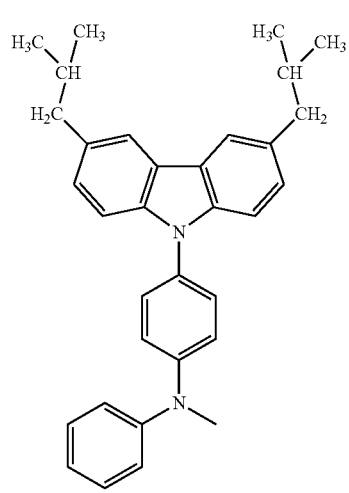
(33-31)

-continued

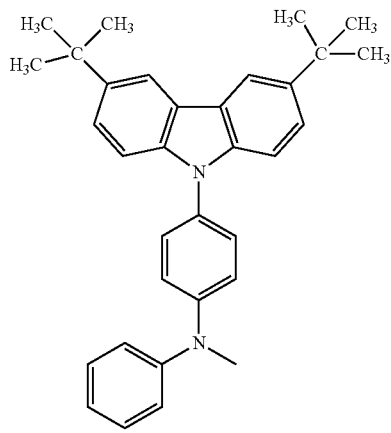

(33-32)

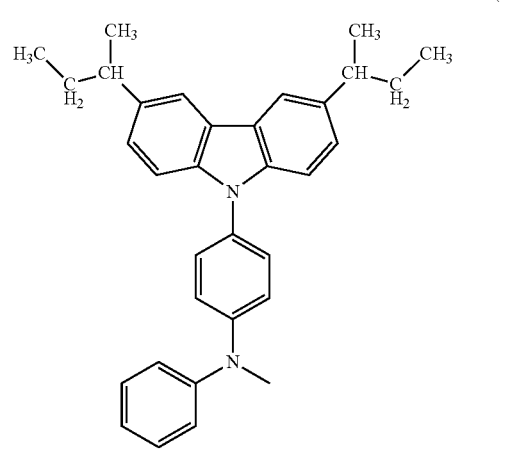

(33-33)

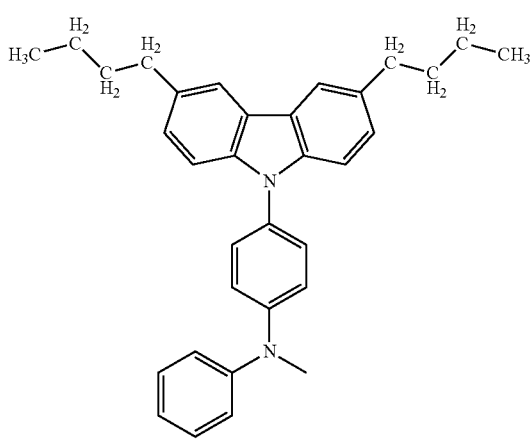

(33-34)

Embodiment Mode 2

In this embodiment mode, an example of a synthetic method of a stilbene derivative, in which $A^{11}$ represents a substituent represented by a general formula (1-1) in the general formula (1) described in Embodiment Mode 1, is described. That is, an example of a synthetic method of a stilbene derivative represented by a general formula (1-1-1) below is described. In the general formula (1-1-1), $Ar^1$ and $Ar^2$ may form a 5-membered ring by being directly bonded to each other. α in the general formula (1-1-1) represents an arylene group having 6 to 25 carbon atoms.

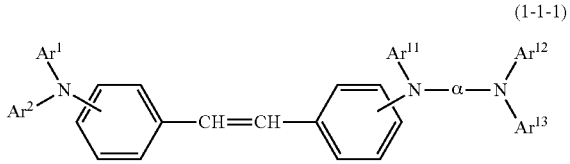

(1-1-1)

Step 1; Synthesis of a Stilbene Derivative (St1) in which any One of 2-Position to 4-Position is Halogenated First, as represented by the following synthetic scheme (A-1), by reacting benzyltriphenylphosphonium salt (α1) in which any one of 2-position to 4-position is halogenated, with a benzaldehyde derivative (β1) in the presence of a base, in other words by a so-called Wittig reaction, a stilbene derivative (St1) in which any one of 2-position to 4-position is halogenated is obtained. $X^1$ and $X^2$ in the synthetic scheme (A-1) each represent halogen, preferably bromine or iodine.

Further, this stilbene derivative (St1) can also be obtained by a Horner-Emmons reaction in which phosphonate ester (α2) is used instead of the triphenylphosphonium salt (α1), as shown in a synthetic scheme (A-1'). $R^1$ in the synthetic scheme (A-1') represents an alkyl group. As the base, organic bases such as metal alkoxide can be used.

In addition, the stilbene derivative (St1) can also be obtained by the Wittig reaction as shown in a synthesis scheme (A-1''). Namely, benzyltriphenylphosphonium salt (α3) in which any one of 2-position to 4-position is substituted by a diarylamino group having $Ar^1$ and $Ar^2$ and benzaldehyde (β2) in which any one of 2-position to 4-position is halogenated are reacted in the presence of a base. Alternatively, as shown by a synthetic scheme (A-1'''), it can also be obtained by a Horner-Emmons reaction in which phosphonate ester (α4) is used instead of the triphenylphosphonium salt (α3).

(A-1)

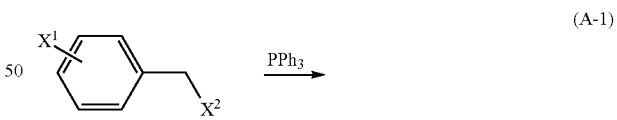

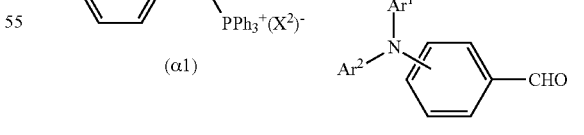

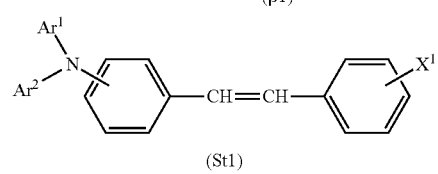

-continued

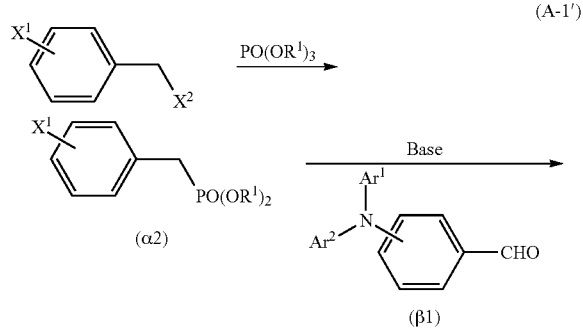

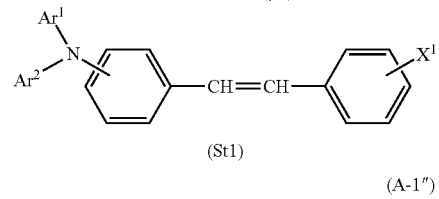

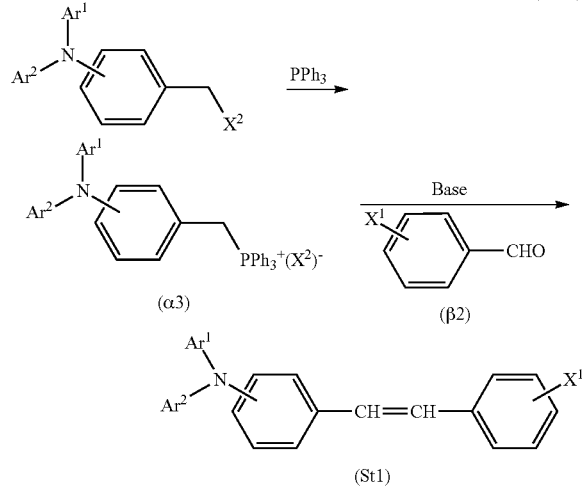

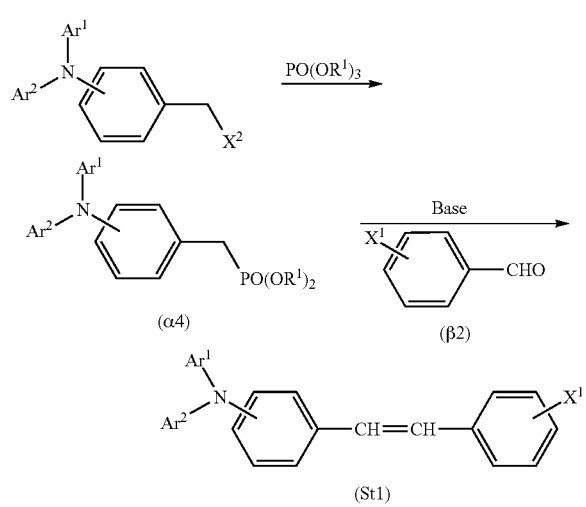

Step 2; Synthesis of a Diamine Derivative (γ2)

Next, as shown by a synthetic scheme (A-2) below, a diamine derivative (γ2) is obtained by coupling a monohalogenated triarylamine (γ1) and arylamine using a metal or a metal compound in the presence of a base. $X^3$ in the synthetic scheme (A-2) represents halogen, preferably bromine or iodine. As a specific example of a metal compound for the coupling, monovalent copper such as copper(I) iodide can be given.

As a specific example of a metal compound used as a catalyst in the coupling, a palladium catalyst such as palladium(II) acetate, tetrakis(triphenylphosphine)palladium(0), or bis(dibenzylideneacetone)palladium(0) can be given. As the base, inorganic bases such as potassium carbonate or sodium carbonate or organic bases such as metal alkoxide (for example, sodium tert-butoxide or potassium tert-butoxide) can be used.

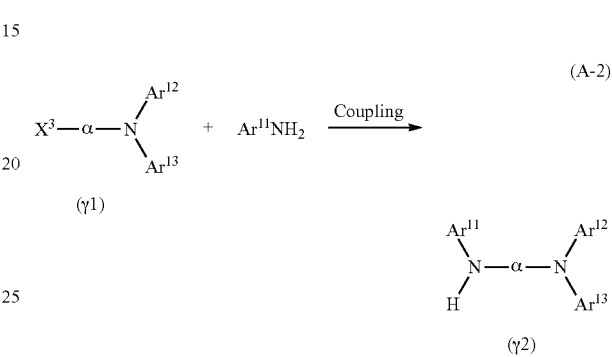

Step 3; Synthesis of a Stilbene Derivative of the Present Invention Represented by the General Formula (1)

Next, as shown by a synthesis scheme (A-3) below, a stilbene derivative of the present invention represented by the general formula (1-1-1) can be obtained by coupling the stilbene derivative (St1) obtained in Step 1 and the diamine derivative (γ2) obtained in Step 2 using a metal or a metal compound in the presence of a base. As the metal and the metal compound, any of the above-described substances can be used. As the base, inorganic bases such as potassium carbonate or sodium carbonate or organic bases such as metal alkoxide (for example, sodium tert-butoxide or potassium tert-butoxide) can be used.

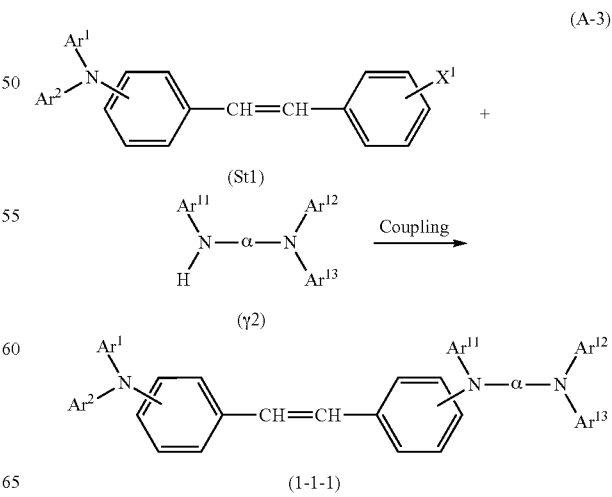

Embodiment Mode 3

In this embodiment mode, an example of a synthetic method of a stilbene derivative in a case where $A^{11}$ represents a substituent represented by a general formula (1-2) in the general formula (1) described in Embodiment Mode 1, is described. That is, an example of a synthetic method of a stilbene derivative represented by the following general formula (1-1-2) is described. In the general formula (1-1-2), $Ar^1$ and $Ar^2$ may form a 5-membered ring by being directly bonded to each other.

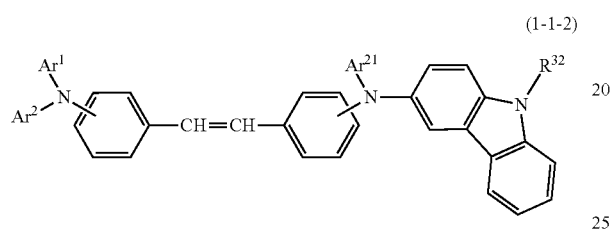

(1-1-2)

Step 1; Synthesis of a Stilbene Derivative (St1) in which any One of 2-Position to 4-Position is Halogenated A stilbene derivative (St1) can be synthesized using the synthetic schemes (A-1) to (A-1''') described in Step 1 of Embodiment Mode 2; therefore, the description of the synthesis is omitted here.

Step 2; Synthesis of a carbazol-3-amine Derivative (Cz1)

Next, as shown by a synthetic scheme (B-2) below, a carbazol-3-amine derivative (Cz1) is obtained by coupling a carbazole derivative (γ3) in which one of the 3-positions is halogenated and arylamine using a metal or a metal compound in the presence of a base. $X^4$ in the synthetic scheme (B-2) represents halogen, preferably bromine or iodine. As the metal or the metal compound for the coupling, the above-described substances can be used. As the base, inorganic bases such as potassium carbonate or sodium carbonate or organic bases such as metal alkoxide (for example, sodium tert-butoxide or potassium tert-butoxide) can be used.

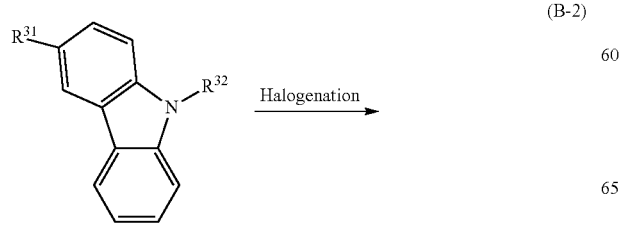

(B-2)

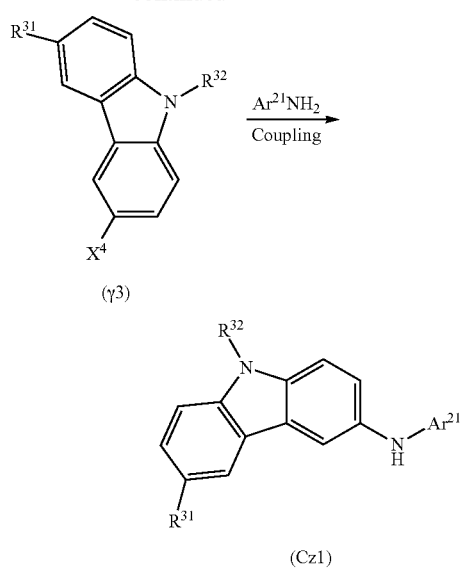

Step 3; Synthesis of a Stilbene Derivative of the Present Invention Represented by the General Formula (1)

Next, as shown by the following synthesis scheme (B-3), a stilbene derivative of the present invention represented by the general formula (1-1-2) can be obtained by coupling the stilbene derivative (St1) obtained in Step 1 and the carbazole-3-amine derivative (Cz1) obtained in Step 2 using a metal or a metal compound in the presence of a base. As the metal or the metal compound, the above-described substances can be used. As the base, inorganic bases such as potassium carbonate or sodium carbonate or organic bases such as metal alkoxide (for example, sodium tert-butoxide or potassium tert-butoxide) can be used.

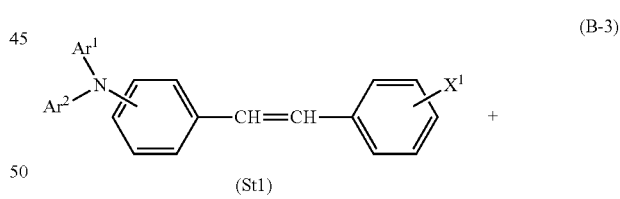

(B-3)

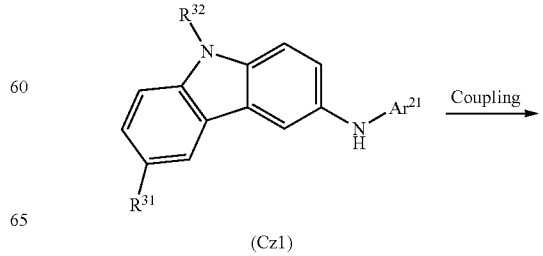

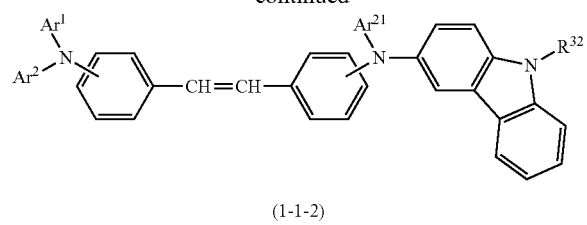

(1-1-2)

Embodiment Mode 4

In this embodiment mode, an example of a synthetic method of a stilbene derivative in a case where $A^{11}$ represents a substituent represented by a general formula (1-3) in the general formula (1), is described. That is, an example of a synthetic method of a stilbene derivative represented by the following general formula (1-1-3) is described. In the general formula (1-1-3), $Ar^1$ and $Ar^2$ may form a 5-membered ring by being directly bonded to each other.

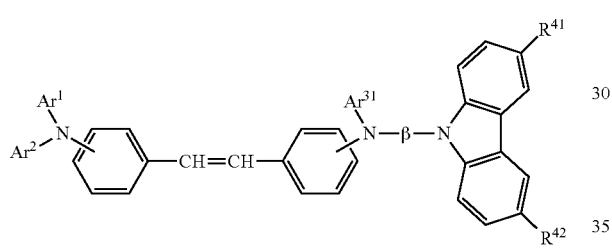

(1-1-3)

Step 1; Synthesis of a Stilbene Derivative (St1) in which any one of 2-Position to 4-Position is Halogenated A stilbene derivative (St1) can be synthesized using the synthetic schemes (A-1) to (A-1''') described in Step 1 of Embodiment Mode 2; therefore, the description of the synthesis is omitted here.

Step 2; Synthesis of a Diarylamine Derivative (Cz2) having Carbazole

Next, as shown by a synthetic scheme (C-2) below, a diarylamine derivative (Cz2) having carbazole is obtained by coupling a 9-arylcarbazole derivative (γ4) in which a halogen atom is introduced to the aryl group and arylamine using a metal or a metal compound in the presence of a base. $X^5$ and $X^6$ in the synthetic scheme (C-2) each represent halogen, preferably bromine or iodine.

β in the synthetic scheme (A-1) represents an arylene group having 6 to 25 carbon atoms. As the metal or the metal compound, used at the coupling, the above-described substances can be used. As the base, inorganic bases such as potassium carbonate or sodium carbonate or organic bases such as metal alkoxide (for example, sodium tert-butoxide or potassium tert-butoxide) can be used.

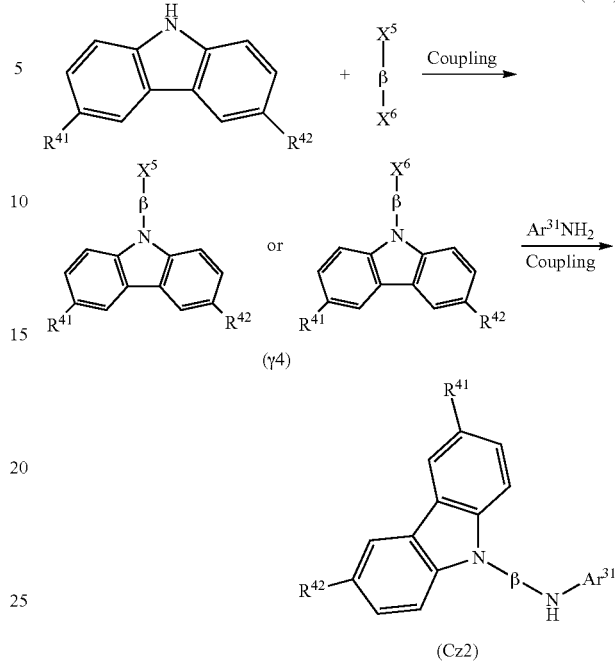

(C-2)

Step 3; Synthesis of a Stilbene Derivative of the Present Invention Represented by the General Formula (1)

Next, as shown by a synthesis scheme (C-3) below, a stilbene derivative of the present invention represented by the general formula (1-1-3) can be obtained by coupling the stilbene derivative (St1) obtained in Step 1 and the diarylamine derivative (Cz2) having carbazole obtained in Step 2 using a metal or a metal compound in the presence of a base. As the metal or the metal compound, the above-described substances can be used. As the base, inorganic bases such as potassium carbonate or sodium carbonate or organic bases such as metal alkoxide (for example, sodium tert-butoxide or potassium tert-butoxide) can be used.

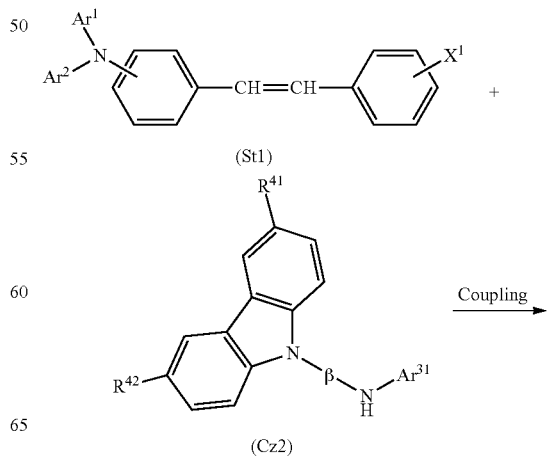

(C-3)

-continued

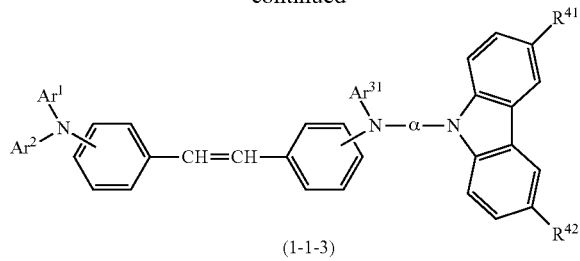

(1-1-3)

Embodiment Mode 5

In this embodiment mode, an example of a light-emitting element which uses a stilbene derivative described in Embodiment Mode 1 for a light-emitting layer or a part of a light-emitting layer, and a method for manufacturing the same is described.

An element structure of a light-emitting element of the present invention has a structure in which a layer 103 including a luminescent substance is interposed between a first electrode 101 and a second electrode 102 as shown in FIG. 1.

A stilbene derivative of the present invention is used for the layer 103 including a luminescent substance. In this embodiment mode, a case is described in which the first electrode serves as an anode and the second electrode serves as a cathode. However, in a structure of a light-emitting element of the present invention, the first electrode can also serve as a cathode and the second electrode can serve as an anode. The anode is an electrode which injects holes into the layer including a luminescent substance and the cathode is an electrode which injects electrons into the layer including a luminescent substance.

The layer 103 including a luminescent substance includes at least a light-emitting layer 104. As examples of the structure of the layer 103 including a luminescent substance, a stacked structure including a hole injecting layer, a light-emitting layer, and an electron transporting layer in that order; a stacked structure including a hole injecting layer, a hole transporting layer, a light-emitting layer, and an electron transporting layer in that order; a stacked structure including a hole injecting layer, a hole transporting layer, a light-emitting layer, a hole blocking layer, and an electron transporting layer in that order; a stacked structure including a hole injecting layer, a hole transporting layer, a light-emitting layer, a hole blocking layer, an electron transporting layer, and an electron injecting layer in that order, and the like can be given.

A stilbene derivative of the present invention is preferably used for the light-emitting layer 104. That is, it is preferable to employ a structure using a stilbene derivative of the present invention for the light-emitting layer 104 or a structure using a stilbene derivative of the present invention as a dopant (light-emitting material) for a part of the light-emitting layer 104.

Further, the light-emitting element of the present invention is preferably supported over a substrate. There is no particular limitation on the kind of the substrate, and a glass substrate, a quartz substrate, a silicon substrate, a metal substrate (for example, a stainless steel substrate), a ceramic substrate, a plastic substrate (for example, an acrylic substrate), or the like can be used.

As for an anode material for the light-emitting element, use of a metal, an alloy, a conductive compound having a high work function (a work function of 4.0 eV or more), a mixture thereof, or the like is preferred. Specific examples of the anode material include gold (Au), platinum (Pt), titanium (Ti), nickel (Ni), tungsten (W), chromium (Cr), molybdenum (Mo), iron (Fe), cobalt (Co), copper (Cu), palladium (Pd), a nitride of a metal material (for example, titanium nitride), or the like, in addition to ITO (indium tin oxide), and TZO (indium zinc oxide) which includes silicon oxide and 2 to 20 atomic % of zinc oxide in indium oxide.

In a case where a first buffer layer described below is provided in contact with the anode on the light-emission layer side of the anode, an ohmic contact is realized between the buffer layer and the anode, which allows the use of a variety of electrode material as an anode regardless work function thereof. Thus, aluminum (Al), silver (Ag), an alkali metal, an alkaline-earth metal such as magnesium (Mg), an alloy including these (e.g., Mg:Ag, Al:Li), or the like which are commonly known as materials having a low work function, can be used as the anode material.

The first buffer layer is formed by combining a metal compound and an organic compound such as an aromatic amine compound, a carbazole derivative, or an aromatic hydrocarbon (including an aromatic hydrocarbon having at least one vinyl skeleton).

As the aromatic amine compound, for example, 4,4'-bis[N-(1-naphthyl)-N-phenylamino]biphenyl (abbreviation: NPB); 4,4'-bis[N-(3-methylphenyl)-N-phenylamino]biphenyl (abbreviation: TPD); 4,4',4''-tris(N,N-diphenylamino)triphenylamine (abbreviation: TDATA); 4,4',4''-tris[N-(3-methylphenyl)-N-phenylamino]triphenylamine (abbreviation: MTDATA); and the like can be given as specific examples.

Further, 4,4'-bis(N-{4-[N,N-bis(3-methylphenyl)amino]phenyl}-N-phenylamino)biphenyl (abbreviation: DNTPD); 1,3,5-tris[N,N-di(m-tolyl)amino]benzene (abbreviation: m-MTDAB); 4,4',4''-tri(N-carbazolyl)triphenylamine (abbreviation: TCTA); 2,3-bis(4-diphenylaminophenyl)quinoxaline (abbreviation: TPAQn); 2,2',3,3'-tetrakis(4-diphenylaminophenyl)-6,6'-bisquinoxaline (abbreviation: D-TriPhAQn); 2,3-bis{4-[N-(1-naphthyl)-N-phenylamino]phenyl}dibenzo[f,h]quinoxaline (abbreviation: NPADiBzQn); and the like can be given as specific examples.

As the carbazole derivative, for example, 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); N-(2-naphthyl)carbazole (abbreviation: NCz); 4,4'-di(N-carbazolyl)biphenyl (abbreviation: CBP); 9,10-bis[4-(N-carbazolyl)phenyl]anthracene (abbreviation: BCPA); 3,5-bis[4-(N-carbazolyl)phenyl]biphenyl (abbreviation: BCPBi); 1,3,5-tris[4-(N-carbazolyl)phenyl]benzene (abbreviation: TCPB) and the like can be given as specific examples.

As the aromatic hydrocarbon (including an aromatic hydrocarbon having at least one vinyl skeleton), anthracene, 9,10-diphenylanthracene (abbreviation: DPAnth.); 2-tert-butyl-9,10-di(2-naphthyl)anthracene (abbreviation: t-BuDNA); tetracene; rubrene; pentacene; 4,4'-bis(2,2-diphenylvinyl)biphenyl (abbreviation: DPVBi); and the like can be given as specific examples.

As the metal compound, an oxide or nitride of a transition metal is preferable. In particular, an oxide or nitride of a metal which belongs to Group 4 to 8 is preferable. In addition, a material having an electron-accepting property with respect to the above-described aromatic amine compounds, carbazole derivatives, and aromatic hydrocarbons (including aromatic hydrocarbons having at least one vinyl skeleton) is preferable. As such a metal compound, for example, molybdenum oxide, vanadium oxide, ruthenium oxide, rhenium oxide, titanium oxide, chromium oxide, zirconium oxide, hafnium oxide, tantalum oxide, tungsten oxide, silver oxide, and the like can be given as specific examples.

Even when any of an aromatic amine, a carbazole derivative, or an aromatic hydrocarbon (including an aromatic hydrocarbon having at least one vinyl skeleton) is used as the organic compound in the first buffer layer, it is preferable that a weight ratio of the metal compound to the organic compound is 0.5 to 2, or a molar ratio is 1 to 4. In addition, the first buffer layer may have a thickness greater than or equal to 50 nm, because it has high conductivity.

As for a cathode material of the light-emitting element, use of a metal, an alloy, a conductive compound having a low work function (a work function of 3.8 eV or less), a mixture thereof, or the like is preferred. As specific examples of the cathode material, an element belonging to Group 1 or 2 of the periodic table, that is, an alkali metal such as Li or Cs, an alkaline earth metal such as Mg, Ca, or Sr, and the like can be given. As other examples of the cathode material, an alloy (e.g., Mg:Ag, Al:Li) or a metal compound (e.g., LiF, CsF, or $CaF_2$) which include an alkali metal or an alkaline earth metal can be used, and a transition metal which includes a rare earth metal can also be used. Further, a structure obtained by stacking metals such as Al, Ag, and ITO (indium tin oxide) or an alloy can also be used.

In a case where a second buffer layer described below is provided in contact with the cathode on a light-emitting layer side of the cathode, an ohmic contact of the buffer layer with an electrode material having a wide range of work function is possible. Thus, ITO, indium tin oxide including silicon oxide, IZO (indium zinc oxide) which includes silicon oxide and 2 to 20 atomic % of zinc oxide in indium oxide, and the like, which are commonly known as materials with a high work function, can be used as the cathode material.

The second buffer layer is formed by a combination of at least one substance selected from electron transporting substances and bipolar substances, and a substance (a donor) showing an electron-donating property with respect to these substances. As examples of the substance (the donor) showing an electron-donating property, alkali metal such as Li or Cs and an alkaline earth metal such as Mg or Ca can be given. As the electron transporting substance and the bipolar substance, a substance having an electron mobility of $1\times10^{-6}$ $cm^2/Vs$ or more is preferable. In addition, substances to be described below can be used for each of the electron transporting substance and the bipolar substance.

Formation of a thin film from the anode material and the cathode material described above using an evaporation method, a sputtering method, or the like allows the fabrication of an anode and a cathode, respectively. The anode and the cathode each preferably have a thickness of 10 to 500 nm.

The light-emitting element of the present invention has a structure in which light generated by recombination of carriers (hole and electron) in the layer including a luminescent substance is emitted outside through one or both of the anode and the cathode. In other words, the anode is made of a material having a light transmitting property in a case where light is extracted through the anode, and the cathode is made of a material having a light transmitting property in a case where light is extracted through the cathode side.

For the layer including a luminescent substance, known materials can be used, and either compounds with low molecular weight or high molecular weight can be used. The materials for forming the layer including a luminescent substance may include not only an organic compound but also an inorganic compound.

The layer including a luminescent substance is formed by appropriately combining layers such as the first buffer layer and the second buffer layer described above as well as a hole injecting layer including a hole injecting substance, a hole transporting layer including a hole transporting substance or a bipolar substance, a light-emitting layer including a luminescent substance, a hole blocking layer including a hole blocking substance, an electron transporting layer including an electron transporting substance, and an electron injecting layer including an electron injecting substance.

In the present invention, in the case of using the stilbene derivative for the light-emitting layer, the layer including a luminescent substance interposed between a pair of electrodes can be formed by stacking the light-emitting layer and other layers (for example, the hole injecting layer, the hole transporting layer, the hole blocking layer, the electron transporting layer, the electron injecting layer, the first buffer layer, the second buffer layer, or the like). Specific substances used for forming these layers are described below. Description of the first buffer layer and the second buffer layer is omitted here, because it has already been made.

The hole injecting layer is preferably formed using a hole injecting substance. As the hole injecting substance, porphyrin- and phthalocyanine-based compounds are efficient among organic compounds. For example, phthalocyanine (hereinafter, referred to as "$H_2$—Pc"), copper phthalocyanine (hereinafter, referred to as "Cu—Pc"), or the like can be used. In addition, a chemically doped conductive compound with high molecular weight such as poly(3,4-ethylenedioxythiophene) (hereinafter, referred to as "PEDOT") doped with poly(styrenesulfonic acid) (hereinafter, referred to as "PSS") can be used.

The hole transporting layer is a layer excellent in a hole transporting property, and is preferably formed of a hole transporting substance or a bipolar substance which has a hole mobility of $1\times10^{-6}$ $cm^2/Vs$ or more. The hole transporting substance is a substance having higher hole mobility than electron mobility, and is preferably a substance having a value of a ratio of hole mobility to electron mobility (=hole mobility/electron mobility) of more than 100.

As the hole transporting substance, for example, an aromatic amine-based (namely a substance having a bond of benzene ring—nitrogen) compound is preferable. As specific examples of a substance which is widely used, for example, 4,4'-bis[N-(3-methylphenyl)-N-phenylamino]biphenyl (hereinafter, referred to as "TPD"); 4,4'-bis[N-(1-naphthyl)-N-phenylamino]biphenyl (hereinafter, referred to as "NPB") which is a derivative thereof; a star burst aromatic amine compound such as 4,4',4"-tri(N-carbazolyl)triphenylamine (hereinafter, referred to as "TCTA"), 4,4',4"-tris(N,N-diphenylamino)triphenylamine (hereinafter, referred to as "TDATA"), or 4,4',4"-tris[N-(3-methylphenyl)-N-phenylamino]triphenylamine (hereinafter, referred to as MTDATA) can be given.

The bipolar substance is a substance which is described as follows: when mobility of an electron and mobility of a hole are compared with each other, a value of a ratio of mobility of one carrier to mobility of the other carrier is less than or equal to 100, preferably less than or equal to 10. As the bipolar substance, for example, 2,3-bis(4-diphenylaminophenyl)quinoxaline (abbreviation: TPAQn); 2,3-bis{4-[N-(1-naphthyl)-N-phenylamino]phenyl}dibenzo quinoxaline (abbreviation: NPADiBzQn); and the like can be given. In particular, among bipolar substances, a substance having a hole mobility and an electron mobility of $1\times10^{-6}$ $cm^2/Vs$ or more is preferable.

The light-emitting layer includes at least one kind of luminescent substance. A luminescent substance herein is a substance with excellent emission efficiency which can emit light of a desired wavelength. The light emitting layer in this embodiment mode is a layer (in other words, a layer including a host substance and a guest substance) in which a stilbene derivative of the present invention is mixed and dispersed in a layer made of a substance (host substance) having a larger band gap (the energy gap between a LUMO level and a HOMO level) than a band gap of the stilbene derivative of the present invention which serves as a guest substance (dopant). Alternatively, the light-emitting layer can have a structure in which a host substance is not used, that is, only a stilbene derivative of the present invention is used for the light-emitting layer. As for the light-emitting layer having either structure, by using a stilbene derivative of the present invention for a light-emitting layer (or a part of a light-emitting layer), a blue light-emitting element with excellent color purity can be obtained.

As a host substance which is combined with a stilbene derivative of the present invention to form a light-emitting layer, 9-[4-(N-carbazolyl)phenyl]-10-phenyl anthracene (abbreviation: CzPA), 4,4'-di(N-carbazolyl)biphenyl (abbreviation: CBP), bis[2-(2-hydroxyphenyl)benzoxazolato]zinc (abbreviation: Zn(BOX)$_2$), 9,10-di(2-naphthyl)anthracene (abbreviation: DNA), 4,4',4"-tri(N-carbazolyl) triphenylamine (abbreviation: TCTA), 2,2',2"-(1,3,5-benzenetriyl)-tris(1-phenyl-1H-benzimidazole) (abbreviation: TPBi) or the like can be used.

The electron transporting layer is a layer which is excellent in an electron transporting property, and specifically, the electron transporting layer is preferably formed of an electron transporting substance or a bipolar substance, which has an electron mobility of $1 \times 10^{-6}$ cm$^2$/Vs or more. The electron transporting substance is a substance having higher electron mobility than hole mobility, and is preferably a substance having a value of a ratio of electron mobility to hole mobility (=electron mobility/hole mobility) of more than 100.

As specific examples of an electron transporting substance, a metal complex having a quinoline skeleton or a benzoquinoline skeleton such as tris(8-quinolinolato)aluminum (hereinafter, referred to as "Alq$_3$"), tris(4-methyl-8-quinolinolato) aluminum (hereinafter, referred to as Almq$_3$), or bis(10-hydroxybenzo[h]quinolinato)beryllium (hereinafter, referred to as "BeBq$_2$"); bis(2-methyl-8-quinolinolato)(4-phenylphenolato)aluminum (hereinafter, referred to as "BAlq") which is a mixed ligand complex; or the like is preferable.

Alternatively, a metal complex having an oxazole-based or thiazole-based ligand such as bis[2-(2-hydroxyphenyl)benzoxazolato]zinc (hereinafter, referred to as "Zn(BOX)$_2$") or bis[2-(2-hydroxyphenyl)benzothiazolato]zinc (hereinafter, referred to as "Zn(BTZ)$_2$") can also be used.

Furthermore, an oxadiazole derivative such as 2-(4-biphenylyl)-5-(4-tert-butylphenyl)-1,3,4-oxadiazole (hereinafter, referred to as "PBD") or 1,3-bis[5-(p-tert-butylphenyl)-1,3,4-oxadiazol-2-yl]benzene (hereinafter, referred to as "OXD-7") can be used as well as the metal complexes described above.

Further alternatively, a triazole derivative such as 3-(4-tert-butylphenyl)-4-phenyl-5-(4-biphenylyl)-1,2,4-triazole (hereinafter, referred to as "TAZ") or 3-(4-tert-butylphenyl)-4-(4-ethylphenyl)-5-(4-biphenylyl)-1,2,4-triazole (hereinafter, referred to as "p-EtTAZ"); a phenanthroline derivative such as bathophenanthroline (hereinafter, referred to as "BPhen") or bathocuproin (hereinafter, referred to as "BCP"); and, further, 4,4-bis(5-methylbenzoxazolyl-2-yl) stilbene (hereinafter, referred to as "BzOs"); or the like can be used as well as the metal complexes described above.

As specific examples of the bipolar substance, the above-mentioned substances can also be used.

As a hole blocking substance, BAlq, OXD-7, TAZ, p-EtTAZ, BPhen, BCP, or the like which are mentioned above can be used.

As described above, by manufacturing a light-emitting element in which a stilbene derivative of the present invention is used for a light-emitting layer or a part of a light-emitting layer, a blue light-emitting element with excellent color purity can be obtained.

Embodiment Mode 6

In this embodiment mode, as an example of a thin film transistor (TFT) which can provide a light-emitting device by combining with a light-emitting element including a stilbene derivative of the present invention, a single gate TFT having a top gate structure is described with reference to FIG. 2.

Figure 2:
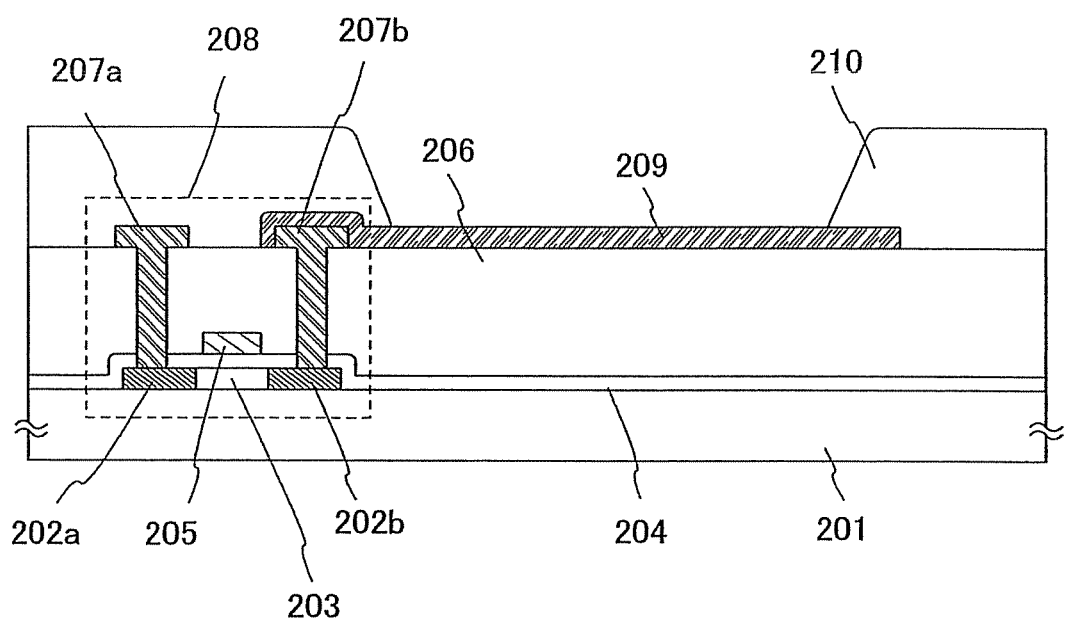
FIG. 2 shows an element substrate having a light-emitting element of the present invention.

As shown in FIG. 2, a TFT 208 is formed over a substrate 201. A drain electrode 207b of the TFT 208 is electrically connected to a first electrode 209 of a light-emitting element. Although not shown, a second electrode is formed over the first electrode 209 with a layer including a luminescent substance therebetween and thus, the light-emitting element as described in Embodiment Mode 5 is formed. With such a structure, the TFT 208 can control driving of the light-emitting element.

There is no particular limitation on the kind of the substrate 201, and a glass substrate, a quartz substrate, a silicon substrate, a metal substrate (for example, a stainless steel substrate), a ceramic substrate, a plastic substrate (for example, an acrylic substrate), or the like can be used.

In addition, although not shown, an insulating film (a base film) formed using silicon oxide, silicon nitride, silicon nitride containing oxygen, silicon oxide containing nitrogen, or the like may be formed between the substrate 201 and the TFT 208 by a method such as a plasma CVD method or a sputtering method. Note that the insulating film may be formed as a single layer film or a multilayer film. By providing an insulating film between the substrate 201 and the TFT 208, impurities can be prevented from diffusing into the TFT 208 from the substrate 201.

A source region 202a, a drain region 202b, and a channel forming region 203 in FIG. 2 are formed of a semiconductor film. As a material for the semiconductor film, a material containing silicon, silicon-germanium (SiGe), or the like as a main component can be used. As the semiconductor film, an amorphous semiconductor film or a crystalline semiconductor film can be used. In this embodiment mode, a case where the crystalline semiconductor film is used as the semiconductor film is described. The semiconductor film can be formed by a method such as a plasma CVD method or a sputtering method. The thickness of the semiconductor film is 10 to 150 nm, preferably 30 to 70 mm.

The crystalline semiconductor film can be formed by crystallizing an amorphous semiconductor film by heating or laser irradiation. Alternatively, a crystalline semiconductor film can be formed in a stage of film formation. For example, the heat-assisted or plasma-assisted crystallization using a fluorine-based gas such as GeF$_4$ or F$_2$, and a silane-based gas such as SiH$_4$ or Si$_2$H$_6$ can be adopted to form a crystalline semiconductor film.

The source region 202a and the drain region 202b are regions in which an impurity element is added to the crystalline semiconductor film. The impurity element is an element which can impart one conductivity type to the semiconductor film, and typically, phosphorus (P) or the like can be given as an impurity element imparting an n-type conductivity type, and boron (B) or the like can be given as an impurity element imparting a p-type conductivity type. When the first electrode 209 serves as an anode, an impurity element imparting p-type conductivity is preferably added. On the other hand, when the first electrode 209 serves as a cathode, an impurity element imparting n-type conductivity is preferably added. In the TFT structure shown in this embodiment mode, after forming a crystalline semiconductor film, an impurity is added to the crystalline semiconductor film by using a gate electrode 205 as a mask.

A gate insulating film 204 formed to cover the source region 202a, the drain region 202b, and the channel forming region 203 is formed using an insulator such as silicon oxide, silicon nitride, silicon nitride containing oxygen, or silicon oxide containing nitrogen by a film-formation method such as a plasma CVD method or a sputtering method. The gate insulating film 204 may be formed to have a single layer structure or a stacked structure. The thickness of the gate insulating film 204 is preferably 10 to 150 nm, more preferably 30 to 70 nm.

The gate electrode 205 can be formed using a conductive film made of a metal nitride such as tantalum nitride or titanium nitride, as well as a metal such as tungsten, aluminum, molybdenum, tantalum, titanium, copper, chromium, or niobium. The conductive film can be formed by a method such as a sputtering method. The gate electrode 205 may be formed to have a single layer structure or a stacked structure. The thickness of the gate electrode 205 is preferably greater than or equal to 200 nm, more preferably 300 to 700 nm.

An interlayer insulating film 206 formed to cover the source region 202a, the drain region 202b, the channel forming region 203, and the gate electrode 205 can be formed using an inorganic-based insulator such as silicon oxide, silicon nitride, silicon nitride including oxygen, or silicon oxide including nitrogen. Besides, an organic resin such as acrylic resin, polyimide, or siloxane-based resin can be used. Note that "siloxane-based resin" is a compound including an element such as silicon (Si), oxygen (O) or hydrogen (H) and further including an Si—O—Si bond (siloxane bond). Such an insulator described above can be formed by a method such as a plasma CVD method, a sputtering method, a coating method, or a spin coating method. The thickness of the interlayer insulating film 206 is preferably 0.3 to 2 μm, more preferably 0.5 to 1 μm.

A source electrode 207a and a drain electrode 207b formed over the interlayer insulating film 206 are electrically connected to the source region 202a and the drain region 202b, respectively. The source electrode 207a and the drain electrode 207b can be formed of an element selected from tantalum, tungsten, titanium, molybdenum, aluminum, copper, chromium, niobium, and the like; or an alloy material or a compound material containing any of the above-described elements as its main component. Alternatively, a semiconductor material typified by polycrystalline silicon doped with an impurity element such as phosphorus can be used.

The source electrode 207 and the drain electrode 207b may be formed to have a single layer structure or a stacked structure. As a specific example of a case where a two-layer structure is employed as the stacked structure, for example, a structure can be given, in which a tantalum nitride film and a tungsten film, a tungsten nitride film and a tungsten film, or a molybdenum nitride film and a molybdenum film are stacked. The thicknesses of the source electrode 207a and the drain electrode 207b are preferably greater than or equal to 200 nm, more preferably 300 to 700 nm.

The drain electrode 207b is electrically connected to the first electrode 209 of the light-emitting element. The material for forming the first electrode 209 is described in Embodiment Mode 5 and the description is omitted here.

An insulator 210 is formed to cover the source electrode 207a, the drain electrode 207b, and the peripheral portion of the first electrode 209. The insulator 210 is preferably formed to have a curvature on its side. The insulator 210 can be formed using acrylic resin, polyimide, silicon oxide, silicon nitride, siloxane-based resin, or the like.

This embodiment mode describes the case where the TFT 208 is a single gate TFT having a top gate structure; however, the present invention is not limited to this structure. That is, a TFT having a bottom gate structure or a multigate type having plural gate electrodes may be used. Further, a TFT having an LDD (Light Doped Drain) structure which has a low concentration impurity region including an impurity at lower concentration than a drain region, between a channel forming region and a drain region, may be employed. Furthermore, a transistor with a gate-overlapped LDD structure in which a low concentration impurity region formed between a channel forming region and a drain region overlaps with a gate electrode, may be used.

By using a stilbene derivative of the present invention for a light-emitting layer of the light-emitting element in a light-emitting device having a TFT described in this embodiment mode and a light-emitting element connected to the TFT, a light-emitting device showing blue emission with excellent color purity can be provided.

Embodiment Mode 7

In this embodiment mode, as an example of a thin film transistor (TFT) which can provide a light-emitting device by combining with a light-emitting element including a stilbene derivative of the present invention, a channel-etch type TFT having a bottom gate structure is described with reference to FIG. 3A and a channel-stop type TFT having a bottom gate structure is described with reference to FIG. 3B.

Figure 3A:
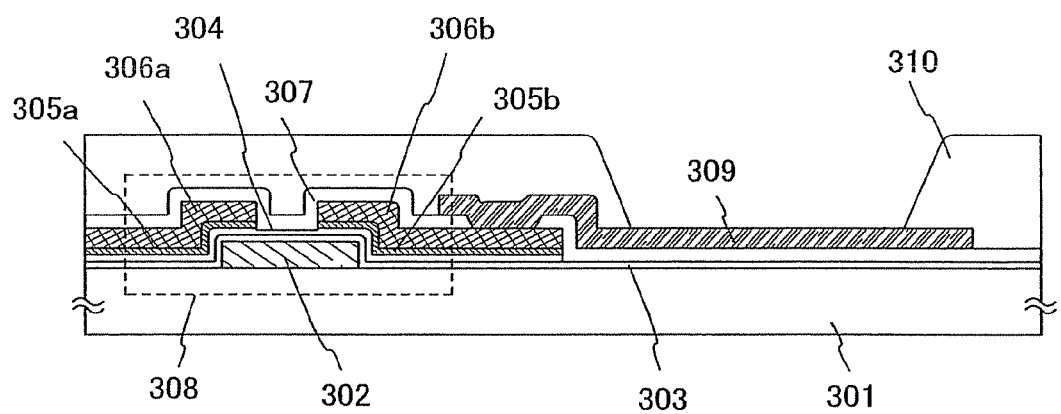
FIGS. 3A and 3B each show an element substrate having a light-emitting element of the present invention.

As shown in FIG. 3A, a channel etch type TFT 308 having a bottom gate structure is formed over a substrate 301. A drain electrode 306b of the TFT 308 is electrically connected to a first electrode 309 of a light-emitting element.

Although not shown, a second electrode is formed over the first electrode 309 with a layer including a luminescent substance therebetween. Thus, the light-emitting element as described in Embodiment Mode 5 is formed. With such a structure, the TFT 308 can control driving of the light-emitting element.

There is no particular limitation on the kind of the substrate 301, and the same materials as the substrate 201 shown in Embodiment Mode 6 can be used. In addition, an insulating film which can be provided between the substrate 301 and the TFT 308 can be formed by the same method and using the same material as in Embodiment Mode 6.

A gate electrode 302 is formed over the substrate 301. A gate insulating film 303 is formed over the gate electrode 302. Note that the gate electrode 302 and the gate insulating film 303 can be formed by the same method and using the same material as the gate electrode 205 and the gate insulating film 204, respectively, described in Embodiment Mode 6.

In a position of overlapping with the gate electrode 302 with the gate insulating film 303 interposed therebetween, a channel forming region 304 formed of a first semiconductor film is formed. The first semiconductor film can be formed by the same method and using the same material as the semiconductor film described in Embodiment Mode 6. In this embodiment mode, a case is described where an amorphous semiconductor film is used as the first semiconductor film. The thickness of the first semiconductor film used here is 10 to 150 nm, preferably 30 to 70 nm.

A source region 305a and a drain region 305b formed of a second semiconductor film are formed over the first semiconductor film. As the second semiconductor film, an amorphous semiconductor film or a crystalline semiconductor film, each of which contains silicon, silicon-germanium (SiGe), or the like as its main component and contains an impurity imparting an n-type or p-type conductivity type, can be used. In this embodiment mode, a case is described where an amorphous semiconductor film is used as the second semiconductor film. The second semiconductor film is an amorphous semiconductor film including an impurity imparting an n-type or p-type conductivity type beforehand. The second semiconductor film can be formed by a method such as a plasma CVD method. The thickness of the second semiconductor film used here is set from 10 to 150 nm, preferably 30 to 70 nm.

A source electrode 306a and a drain electrode 306b are formed over and in contact with the source region 305a and the drain region 305b, respectively. Note that the source electrode 306a and the drain electrode 306b can be formed by the same method, using the same material, and with the same thickness as the source electrode 207a and the drain electrode 207b shown in Embodiment Mode 6.

The TFT 308 includes the gate electrode 302, the gate insulating film 303, the channel forming region 304, the source region 305a, the drain region 305b, the source electrode 306a, and the drain electrode 306b. An interlayer insulating film 307 is formed to cover the TFT 308. The interlayer insulating film 307 can be formed using the same material as the interlayer insulating film 206 described in Embodiment Mode 6.

The drain electrode 306b is electrically connected to the first electrode 309 of the light-emitting element through an opening portion formed in part of the interlayer insulating film 307. The method, material, and thickness for forming the first electrode 309 are described in Embodiment Mode 5 and the description is omitted here.

An insulator 310 formed to cover the TFT 308 and the peripheral portion of the first electrode 309 can be formed by the same method, using the same material, and with the same thickness as the insulator 210 shown in Embodiment Mode 6.

Next, a channel-stop type TFT 328 having a bottom gate structure is described with reference to FIG. 3B. The TFT 328 is formed over a substrate 321, and a drain electrode 326b of the TFT 328 is electrically connected to a first electrode 329 of the light-emitting element. Although not shown, a second electrode is formed over the first electrode 329 with a layer including a luminescent substance therebetween. Thus, the light-emitting element as described in Embodiment Mode 5 is formed. With such a structure, the TFT 328 can control driving of the light-emitting element.

Figure 3B:
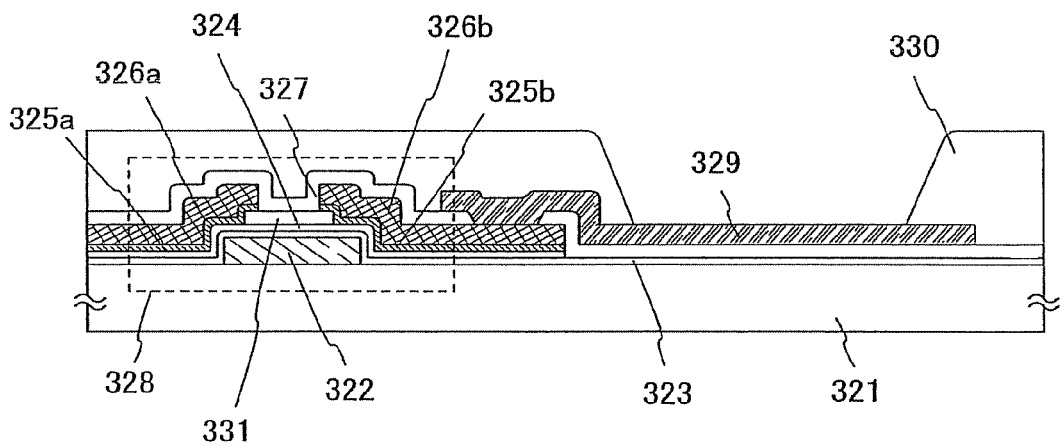

In the channel-stop type TFT 328 having a bottom gate structure shown in FIG. 3B, a protective film 331 is provided over a channel forming region 324, in a position of overlapping with the gate electrode.

Note that the protective film 331 is a film having a function of protecting the first semiconductor film forming the channel forming region 324 in order not to be etched when a second semiconductor film and a conductive film are processed to form a source region 325a, a drain region 325b, a source electrode 326a, and a drain electrode 326b. The protective film 331 may be formed using an insulating film such as silicon oxide, silicon nitride, silicon nitride containing oxygen, or silicon oxide containing oxygen by a film-formation method such as a plasma CVD method or a sputtering method.

In addition, a gate electrode 322, a gate insulating film 323, the channel forming region 324, the source region 325a, the drain region 325b, the source electrode 326a, the drain electrode 326b, an interlayer insulating film 327, the first electrode 329, and an insulator 330 shown in FIG. 3B may be formed by the same method, using the same material, and with the same thickness as the gate electrode 302, the gate insulating film 303, the channel forming region 304, the source region 305a, the drain region 305b, the source electrode 306a, the drain electrode 306b, the interlayer insulating film 307, the first electrode 309, and the insulator 310, respectively, described with reference to FIG. 3A. Thus, description made in FIG. 3A is referred to, and description of the method, material, and thickness thereof is omitted here.

By using a stilbene derivative of the present invention for a light-emitting layer of a light-emitting element in a light-emitting device having a TFT described in this embodiment mode and a light-emitting element connected to the TFT, a light-emitting device showing blue emission with excellent color purity can be provided in the present invention.

Embodiment Mode 8

In this embodiment mode, a light-emitting device having a light-emitting element manufactured using the present invention in a pixel portion is described with reference to FIGS. 4A and 4B. Note that the structure of a light-emitting device in this specification includes a control means such as a driver circuit for driving the light-emitting element, as well as the light-emitting element of the present invention.

Figure 4A:
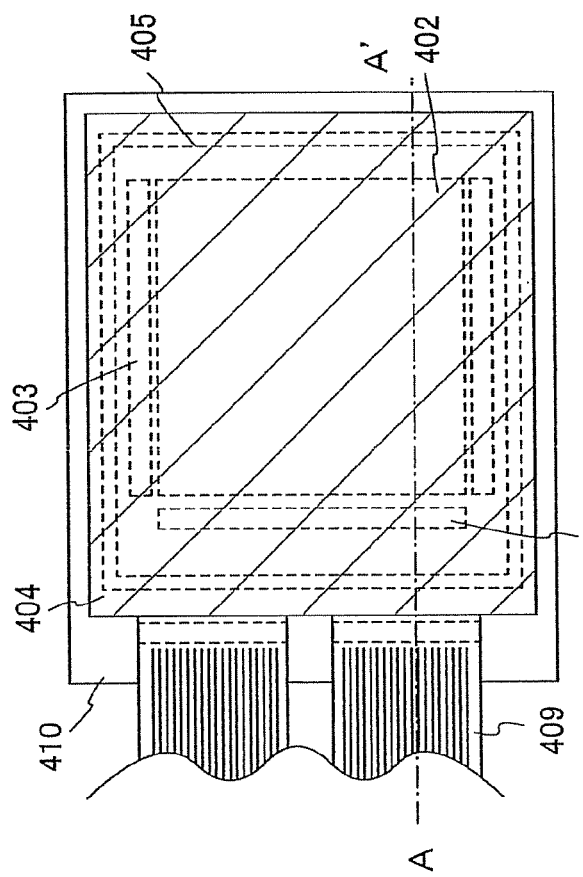
FIGS. 4A and 4B show a light-emitting device having a light-emitting element of the present invention.
Figure 4B:
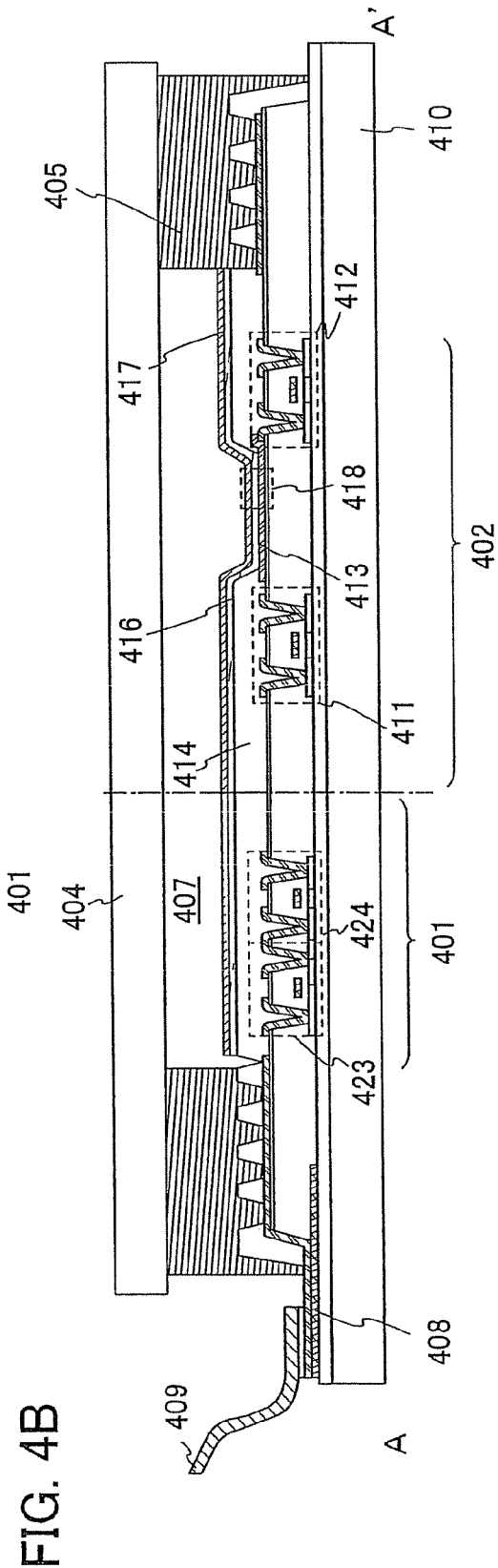

FIG. 4A is a top view showing the light-emitting device, and FIG. 4B is a cross-sectional view taken along a line A-A' of FIG. 4A. A reference numeral 401 indicated by a dashed line denotes a driver circuit portion (a source side driver circuit); 402, a pixel portion; and 403, a driver circuit portion (a gate side driver circuit). Reference numeral 404 denotes a sealing substrate; reference numeral 405 denotes a sealant; and an inner side region surrounded by the sealant 405 is a space 407.

Reference numeral 408 denotes a wiring for transmitting signals input to the source side driver circuit 401 and the gate side driver circuit 403 and receives a video signal, a clock signal, a start signal, a reset signal, and the like from an FPC (Flexible Printed Circuit) 409 serving as an external input terminal. Only the FPC is shown here, however, a printed wiring board (PWB) may be attached to the FPC. In this specification, the light-emitting device includes the light-emitting device on which the FPC or the PWB is mounted as well as the light-emitting device itself.

Next, a cross-sectional structure of the light-emitting device is described with reference to FIG. 4B. In FIG. 4B, the source side driver circuit 401 which is the driver circuit portion and the pixel portion 402 are formed over an element substrate 410.

In this embodiment mode, as the source side driver circuit 401, a CMOS circuit which is obtained by combining an n-channel TFT 423 and a p-channel TFT 424 is formed. However, the TFT forming the driver circuit may be a PMOS circuit or an NMOS circuit. Although a driver-integrated type light-emitting device, in which the pixel portion and the driver circuit are formed in an integrated manner over the substrate, is shown in this embodiment mode, the light-emitting device is not necessarily limited to this structure. That is, a light-emitting device, in which a driver circuit portion fabricated over a substrate is attached to a substrate over which a pixel portion is formed, can also be manufactured.

The pixel portion 402 is formed of a plurality of pixels having a switching TFT 411, a current control TFT 412, and a first electrode 413 electrically connected to a drain of the current control TFT 412. An insulator 414 is formed to cover an end portion of the first electrode 413. In this embodiment mode, the insulator 414 is formed using a positive type photosensitive acrylic resin film. Over the first electrode 413, a layer 416 including a luminescent substance and a second electrode 417 are formed.

Here, it is desirable to use a material having a high work function as a material for forming the first electrode 413 in a case of serving the first electrode 413 as an anode. For example, a single layer structure using an indium tin oxide (ITO) film, an indium zinc oxide (IZO) film, a titanium nitride film, a chromium film, a tungsten film, a Zn film, a Pt film, or the like; a two-layer structure of a film mainly containing titanium nitride and a film mainly containing aluminum; a three-layer structure of a titanium nitride film, a film mainly containing aluminum, and a titanium nitride film; or the like can be used. It is preferred to form the first electrode 413 as a stacked structure because a good ohmic contact can be readily achieved between the first electrode 413 with the drain electrode of the current control TFT 412.

The layer 416 including a luminescent substance can be formed by an evaporation method using an evaporation mask or an inkjet method. As the material which forms the layer 416 including a luminescent substance or the structure of the layer 416 including a luminescent substance, the material and the structure described in Embodiment Mode 5 can be appropriately used; therefore, the description is omitted here.

Further, in this embodiment mode, a buffer layer is provided to be in contact with one electrode (an anode or a cathode) of the two electrodes of the light-emitting element, to be in contact with the two electrodes, or to be in contact with neither of the two electrodes.

The second electrode (cathode) 417 is formed over the layer 416 including a luminescent substance.

By attaching the sealing substrate 404 to the element substrate 410 with the sealant 405, a structure is obtained in which a light-emitting element 418 is provided in the space 407 surrounded by the element substrate 410, the sealing substrate 404, and the sealant 405. A structure in which the space 407 is filled with an inert gas (nitrogen or argon) and a structure in which the space 407 is filled with the sealant 405 are preferable in order to suppress deterioration of a light-emitting element of the present invention.

As the sealant 405, it is preferable to use a material (for example, an epoxy-based resin) which does not transmit moisture and oxygen as little as possible. Further, there is no particular limitation on a material to be used for the sealing substrate 404, and a glass substrate, a quartz substrate, a silicon substrate, a metal substrate (for example, a stainless steel substrate), a ceramic substrate, a plastic substrate (for example, an acrylic substrate), or the like can be used.

As described above, by manufacturing a light-emitting device with the use of a stilbene derivative of the present invention, a light-emitting device showing blue emission with excellent color purity can be provided. The light-emitting device shown in this embodiment mode can be freely combined with any of the structures shown in Embodiment Modes 1 to 7.

Embodiment Mode 9

In this embodiment mode, an example is explained, in which a light-emitting element having a stilbene derivative manufactured according to the present invention is applied to an electronic device. As specific examples of an electronic device, there are a video camera, a digital camera, a projector, a head mounted display (a goggle type display), a car navigation system, a car stereo, a personal computer, a game machine, a mobile information terminal (e.g., a mobile computer, a mobile phone, or an electronic book), an image reproducing device provided with a recording medium (specifically, a device which reproduces a recording medium such as Digital Versatile Disc (DVD) and is provided with a display which can display the image), and the like. Specific examples of an electronic device are shown in FIGS. 5A to 5C.

Figure 5A:
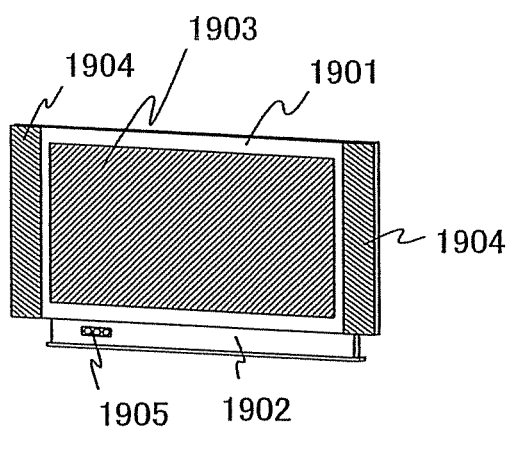
FIGS. 5A to 5C each show an electronic device of the present invention.

FIG. 5A shows a display device, which includes a chassis 1901, a supporting base 1902, a display portion 1903, a speaker portion 1904, a video input terminal 1905, and the like. Since the light-emitting element having a stilbene derivative described in the above embodiment modes has excellent color purity of blue, by using the light-emitting element for the display portion 1903, a display device which is excellent in color reproducibility can be manufactured. The display device includes all display devices used for displaying information, for example, for a computer, for TV broadcast reception, or for advertisement display.

Figure 5B:
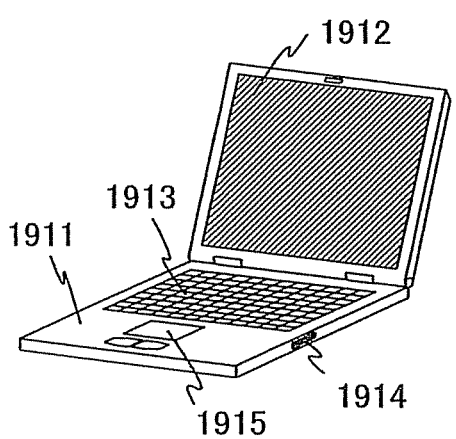

FIG. 5B shows a computer, which includes a chassis 1911, a display portion 1912, a keyboard 1913, an external connecting port 1914, a pointing device 1915, and the like. Since the light-emitting element having a stilbene derivative described in the above embodiment modes has excellent color purity of blue, by using the light-emitting element for the display portion 1912, a computer which is excellent in color reproducibility can be manufactured.

Figure 5C:
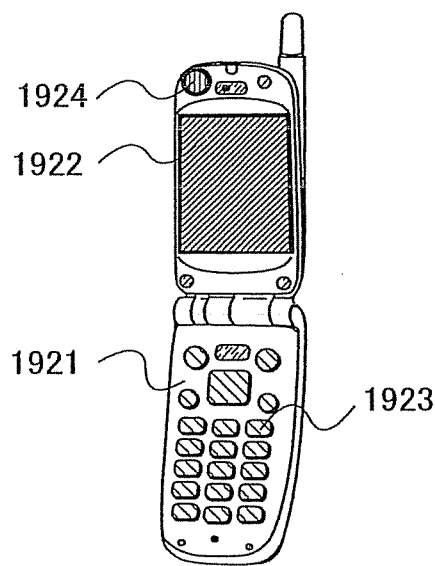

FIG. 5C shows a mobile phone, which is a typical example of a mobile information terminal. This mobile phone includes a chassis 1921, a display portion 1922, a sensor portion 1924, operation keys 1923, and the like. The sensor portion 1924 includes an optical sensor element, and current consumption of the mobile phone can be reduced by controlling luminance of the display portion 1922 in accordance with illuminance obtained at the sensor portion 1924 or by controlling luminance of the operation key 1923 in accordance with the illuminance obtained at the sensor portion 1924.

In addition, in the case of a mobile phone having an imaging function such as a CCD, whether or not a person taking a picture looks into an optical finder is detected based on the change in the amount of light received by a sensor of the sensor portion 1924 provided in the vicinity of the optical finder. In the case where a person taking a picture looks into the optical finder, power consumption can be suppressed by turning off the display portion 1922. Since the light-emitting element having a stilbene derivative described in the above embodiment modes has excellent color purity of blue, by using the light-emitting element for the display portion 1922, a mobile phone which is excellent in color reproducibility can be manufactured.

As described above, the applicable range of the light-emitting element having a stilbene derivative manufactured according to the present invention is so wide that the light-emitting element having a stilbene derivative manufactured according to the present invention can be used for electronic devices in various fields. This embodiment mode can be freely combined with any of the above embodiment modes.

Embodiment 1

In this embodiment, an example of a synthetic method of a stilbene derivative of the present invention is explained. It is to be noted that a stilbene derivative of the present invention is not limited to being manufactured by the synthetic method described in this embodiment.

In this embodiment, an example of a synthetic method of (K)-4-{N-[4-(9H-carbazol-9-yl)phenyl]-N-phenyl}amino-4'-(9H-carbazol-9-yl)stilbene (hereinafter, abbreviated as "YGACzS") which is an example of the stilbene derivative is described. A synthetic scheme of the substance is shown in the following Steps 1 to 4.

Step 1; Synthesis of 4-bromobenzyl triphenylphosphonium bromide

First, 25.2 g (101 mmol) of 4-bromobenzyl bromide and 100 mL of acetone were placed in a 200 mL conical flask, and 29.1 g (111 mmol) of triphenylphosphine was added thereto. This reaction mixture was stirred at room temperature for 23 hours. After the completion of the reaction, the precipitate in the reaction mixture was collected by suction filtration. 50.5 g of a white powdered solid, 4-bromobenzyl triphenylphosphonium bromide, which was the target substance, was obtained in a yield of 97.6%. A synthetic scheme (a-1) of 4-bromobenzyl triphenylphosphonium bromide is shown below.

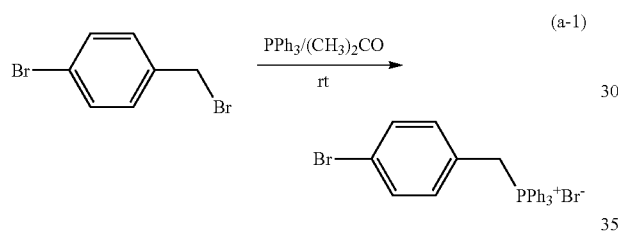

(a-1)

Step 2; Synthesis of (E)-4-bromo-4'-(9H-carbazol-9-yl)stilbene

Next, 9.44 g (18.4 mmol) of 4-bromobenzyl triphenylphosphonium bromide obtained in Step 1 and 5.00 g (18.4 mmol) of 4-(9H-carbazol-9-yl)benzaldehyde were placed into a 300 mL three-neck flask, and nitrogen substitution was carried out in the three-neck flask. Then, 50 mL of tetrahydrofuran (THF) was added thereto. A suspension in which 2.07 g (18.4 mmol) of potassium tert-butoxide was mixed in 50 mL of THF was dropped into this mixture. After the completion of the dropping, the reaction mixture was stirred at room temperature for 24 hours.

After the completion of the reaction, water was added to the reaction mixture, and the precipitate was collected by suction filtration. 4.41 g of a yellow powdered solid, (E)-4-bromo-4'-(9H-carbazol-9-yl)stilbene, which was the target substance, was obtained in a yield of 56.4%. It was confirmed that (Z)-4-bromo-4'-(9H-carbazol-9-yl)stilbene which is an isomer of the target substance was included in the obtained filtrate. A synthetic scheme (a-2) of (E)-4-bromo-4'-(9H-carbazol-9-yl)stilbene is shown below.

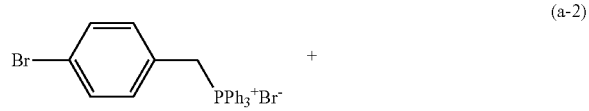

(a-2)

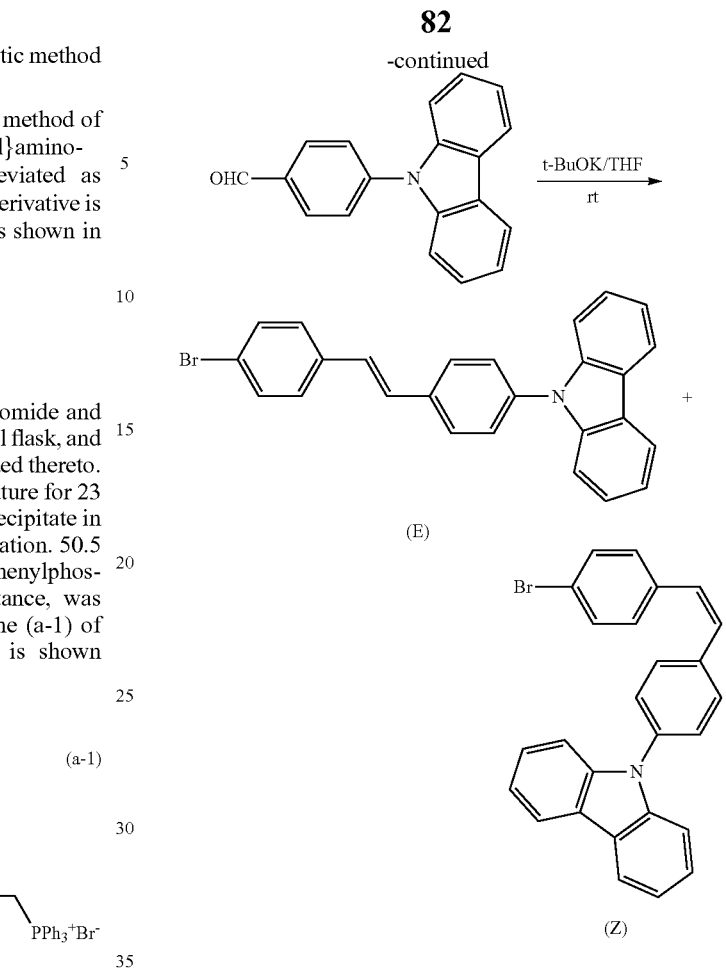

Step 3; Synthesis of N-[(4-(9H-carbazol-9-yl)]phenyl-N-phenylamine (hereinafter, abbreviated as "YGA")

56.3 g (0.24 mol) of 1,4-dibromobenzene, 31.3 g (0.18 mol) of carbazole, 4.6 g (0.024 mol) of copper iodide, 66.3 g (0.48 mol) of potassium carbonate, and 2.1 g (0.008 mol) of 18-crown-6-ether were placed into a 300 mL three-neck flask, and nitrogen substitution was carried out in the three-neck flask. 8 mL of 1,3-dimethyl-3,4,5,6-tetrahydro-2(1H)-pyrimidinone (abbreviation: DMPU) was added to this mixture, and then the mixture was stirred at 180° C. for 6 hours under a nitrogen stream.

After the reaction mixture was cooled to room temperature, the precipitate was removed by suction filtration, and the filtrate was obtained. This filtrate was washed with a diluted hydrochloric acid, a saturated sodium hydrogencarbonate aqueous solution, and brine in that order, and then dried with magnesium sulfate. After the drying, the reaction mixture was filtered and the obtained filtrate was concentrated. The oily substance obtained by this concentration was purified by silica gel column chromatography (hexane:ethyl acetate=9:1), and this was recrystallized with chloroform and hexane. 20.7 g of a light-brown plate-like crystal, which was the target substance, was obtained in a yield of 35%. This compound was identified by a nuclear magnetic resonance method (NMR) as N-(4-bromophenyl)carbazole.

$^1$H NMR of this compound is shown below.

$^1$H NMR (300 MHz, CDCl$_3$) δ=8.14 (d, J=7.8 Hz, 2H), 7.73 (d, J=8.7 Hz, 2H), 7.46 (d, J=8.4 Hz, 2H), 7.42-7.26 (m, 6H).

Next, 5.4 g (17.0 mmol) of the obtained N-(4-bromophenyl)carbazole, 1.8 mL (20.0 mmol) of aniline, 100 mg (0.17 mmol) of bis(dibenzylideneacetone)palladium(0) (abbreviation: Pd(dba)$_2$), and 3.9 g (40 mmol) of sodium tert-butoxide (abbreviation: tert-BuONa) were put into a 200 mL three-neck flask, and nitrogen substitution was carried out in the three-neck flask. After a 10 wt % hexane solution of 0.1 mL of tri-tert-butylphosphine (abbreviation: P(tert-Bu)$_3$) and 50 mL of dehydrated toluene were added to this mixture, stirring was performed at 80° C. for 6 hours under a nitrogen stream.

Then, the reaction mixture was filtered through Florisil, celite, and alumina. The filtrate obtained by the filtration was washed with water and brine, and then dried with magnesium sulfate. The reaction mixture was filtered, and the filtrate was concentrated, and an oily substance was obtained. This substance was purified by silica gel column chromatography (hexane:ethyl acetate=9:1), and 4.1 g of the target substance was obtained in a yield of 73%. This compound was identified by a nuclear magnetic resonance method (NMR) as N-[(4-(9H-carbazol-9-yl)]phenyl-N-phenylamine (abbreviation: YGA).

$^1$H NMR data of this compound is shown below.

$^1$H NMR (300 MHz, DMSO-d$_6$) δ=8.47 (s, 1H) 8.22 (d, J=7.8 Hz, 2H), 7.44-7.16 (m, 14H), 6.92-6.87 (m, 1H)

A synthetic scheme (a-3) of YGA is shown below.

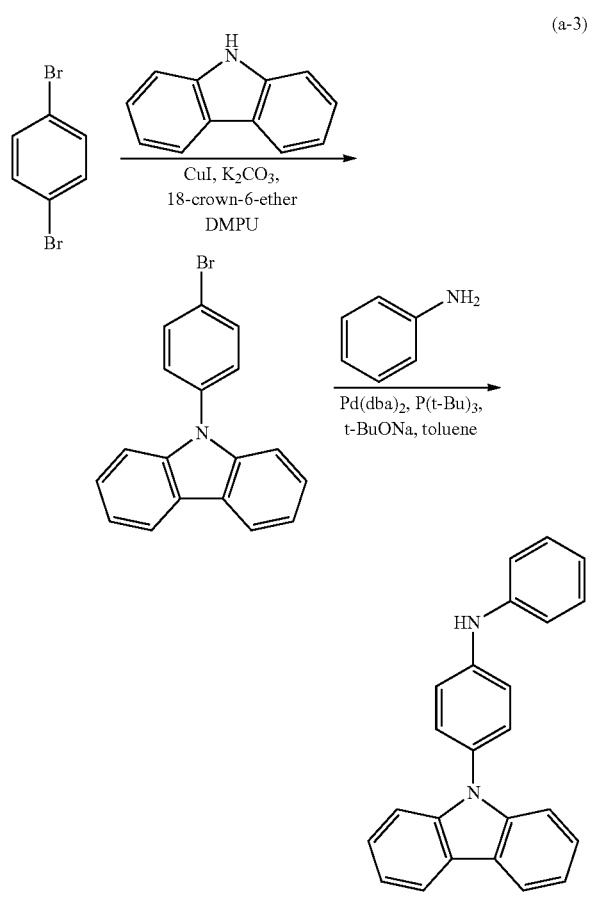

(a-3)

Step 4; Synthesis of (E)-4-{N-[4-(9H-carbazol-9-yl)phenyl]-N-phenyl}amino-4'-(9H-carbazol-9-yl)stilbene (YGACzS)

Next, 1.0 g (2.4 mmol) of the (E)-4-bromo-4'-(carbazol-9-yl)stilbene obtained in Step 2, 0.87 g (2.6 mmol) of the N-(4-carbazol-9-yl)-N-phenylamine (YGA) obtained in Step 3, 0.068 g (0.12 mmol) of bis(dibenzylideneacetone)palladium(0), and 1.1 g (12 mmol) of sodium tert-butoxide were placed in a 100 mL three-neck flask, and nitrogen substitution was carried out in the three-neck flask. 20 mL of toluene and 0.095 g (0.047 mmol) of tri-tert-butylphosphine (10% hexane solution) were added to this mixture. This reaction mixture was stirred at 80° C. for 7 hours.

After the completion of the reaction, the reaction solution was washed with water, and the aqueous phase was extracted with ethyl acetate. The extracted solution combined with the organic phase was dried with magnesium sulfate. After the drying, the mixture was subjected to suction filtration and the filtrate was concentrated. The obtained solid was dissolved in a mixed solvent of toluene and chloroform, and the resulting solution was subjected to suction filtration through Florisil, celite, and alumina. The filtrate was concentrated, and the obtained solid was recrystallized with a mixed solvent of chloroform and hexane. 1.5 g of a light-yellow powdered solid, which was the target substance, was obtained in a yield of 92%. This compound was identified by a nuclear magnetic resonance method (NMR) as (E)-4-{N-[4-(9H-carbazol-9-yl)phenyl]-N-phenyl}amino-4'-(9H-carbazol-9-yl)stilbene (YGACzS).

A synthetic scheme (a-4) of YGACzS is shown below.

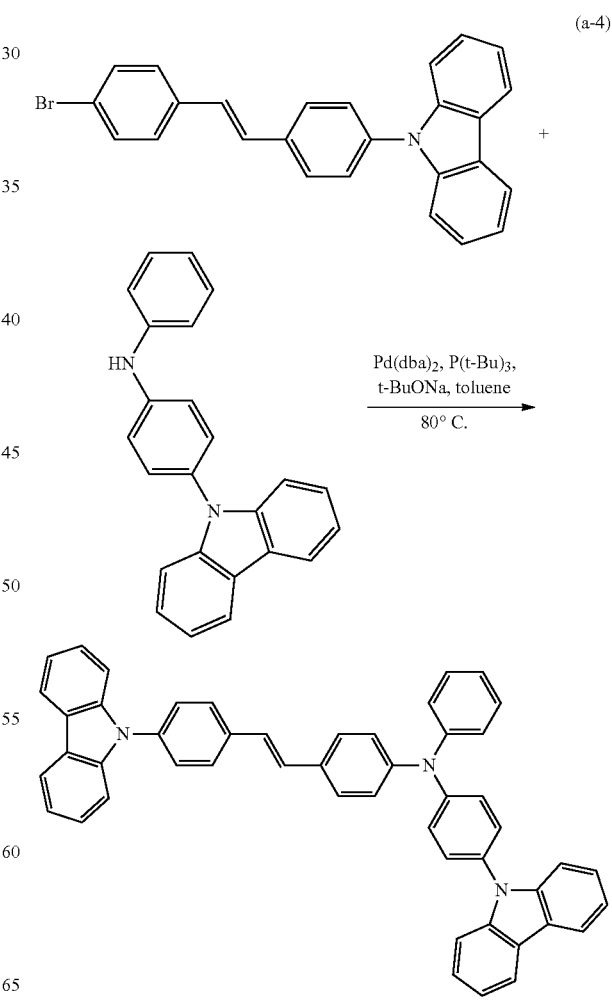

(a-4)

Figure 6A:
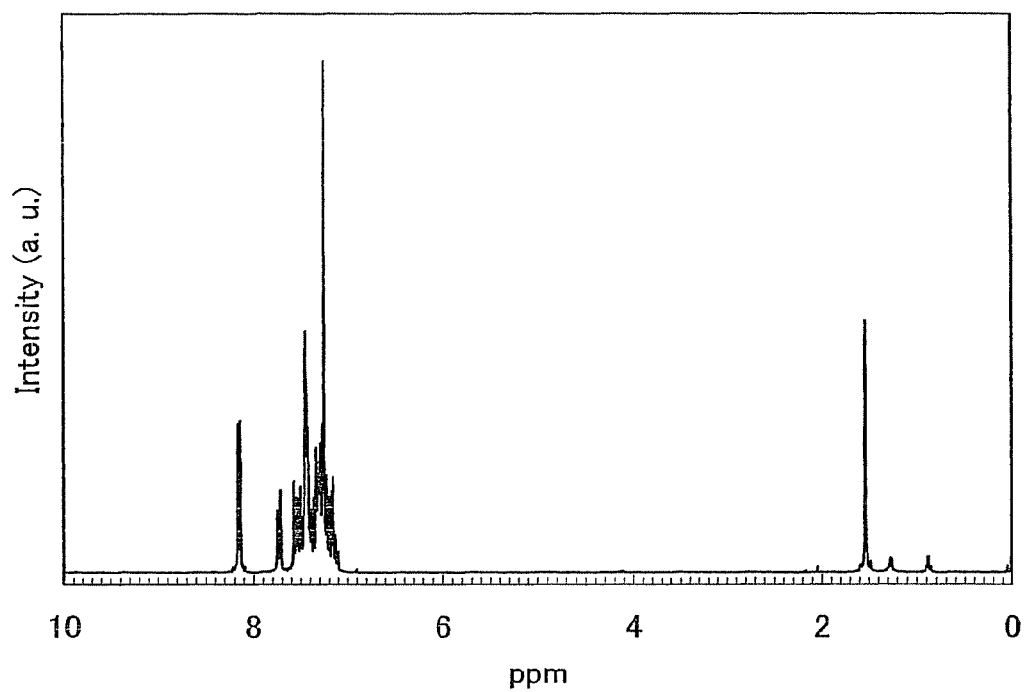
FIGS. 6A and 6B each show a $^1$H NMR chart of (E)-4-{N-[4-(9H-carbazol-9-yl)phenyl]-N-phenyl}amino-4'-(9H-carbazol-9-yl)stilbene (abbreviation: YGACzS)
Figure 6B:
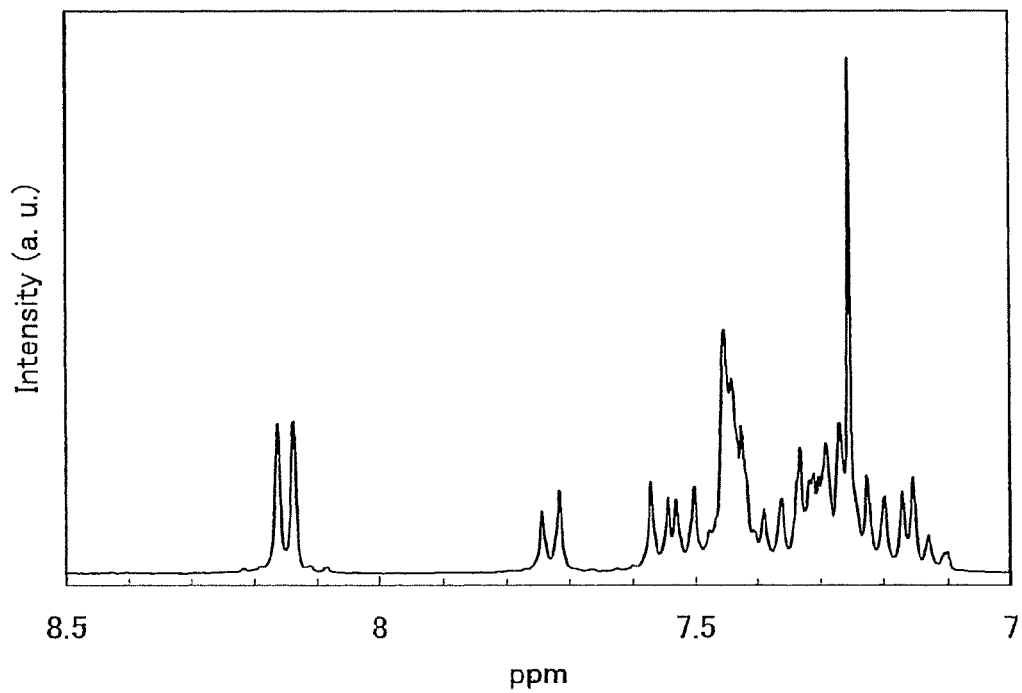

¹H NMR data of the obtained YGACzS is shown below. FIGS. 6A and 6B are each a ¹H NMR chart, and FIG. 6B is an enlarged chart of the 7 ppm to 8.5 ppm range in FIG. 6A.

¹H NMR (CDCl$_3$, 300 MHz): δ=7.10-7.57 (m, 29H), 7.73 (d, J=8.1 Hz, 2H), 8.15 (d, J=7.8 Hz, 4H)

Thermogravimetry-differential thermal analysis (TG-DTA) was performed on the obtained YGACzS. The measurement performed using a thermogravimetric/differential thermal analyzer (TG/DTA 320, manufactured by Seiko Instruments Inc.) revealed that the 5% weight loss temperature was 437.8° C., which means that the YGACzS is a material having favorable heat resistance.

Figure 7A:
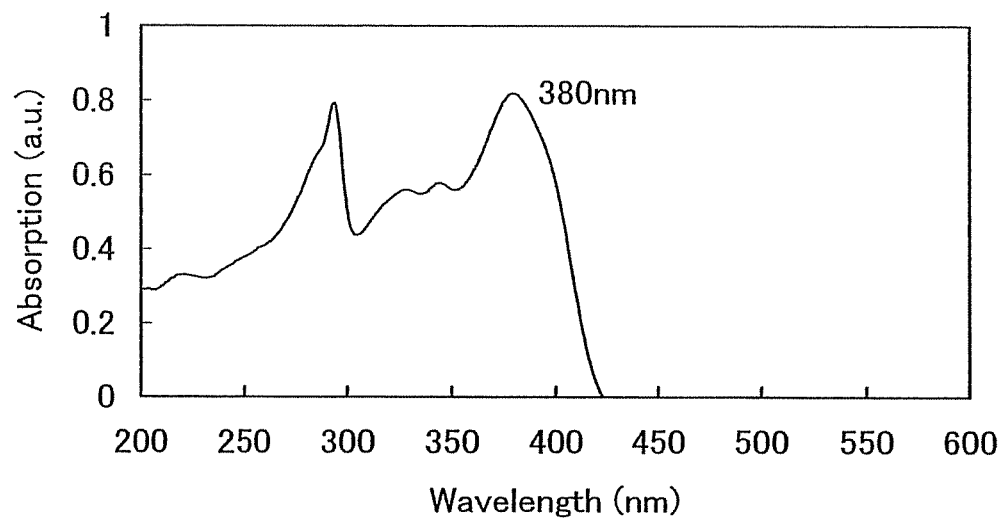
FIGS. 7A and 7B each show an absorption spectrum of YGACzS.

FIG. 7A shows an absorption spectrum of YGACzS in toluene. In FIG. 7A, the horizontal axis indicates the wavelength (nm) and the vertical axis indicates the absorption intensity (arbitrary unit).

Figure 7B:
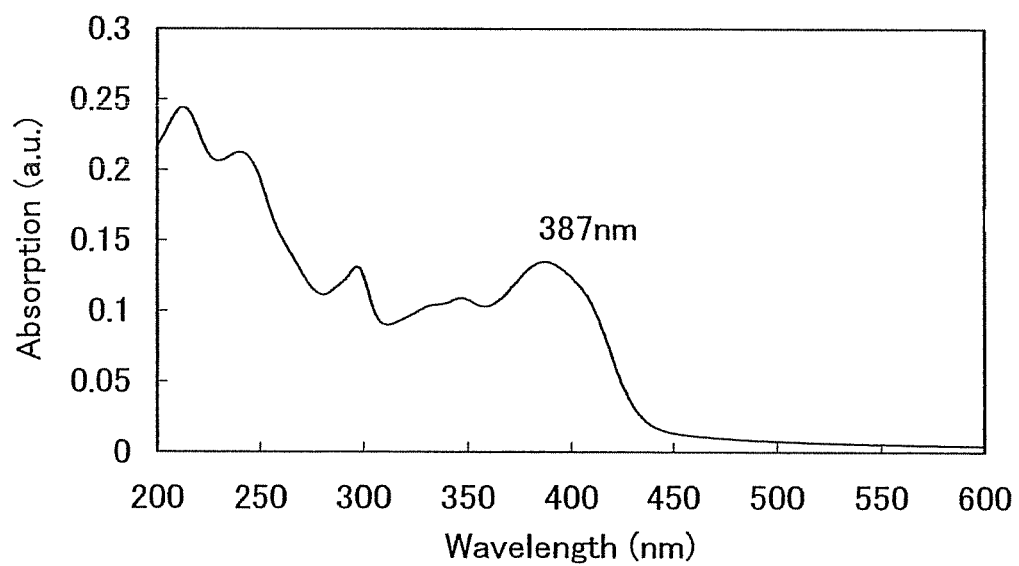

FIG. 7B shows an absorption spectrum in a thin film state obtained by depositing the obtained YGACzS by an evaporation method. In FIG. 7B, the horizontal axis indicates the wavelength (nm) and the vertical axis indicates the absorption intensity (arbitrary unit). The absorption spectra were measured using an ultraviolet-visible spectrophotometer (V-550, manufactured by JASCO Corporation).

Figure 8A:
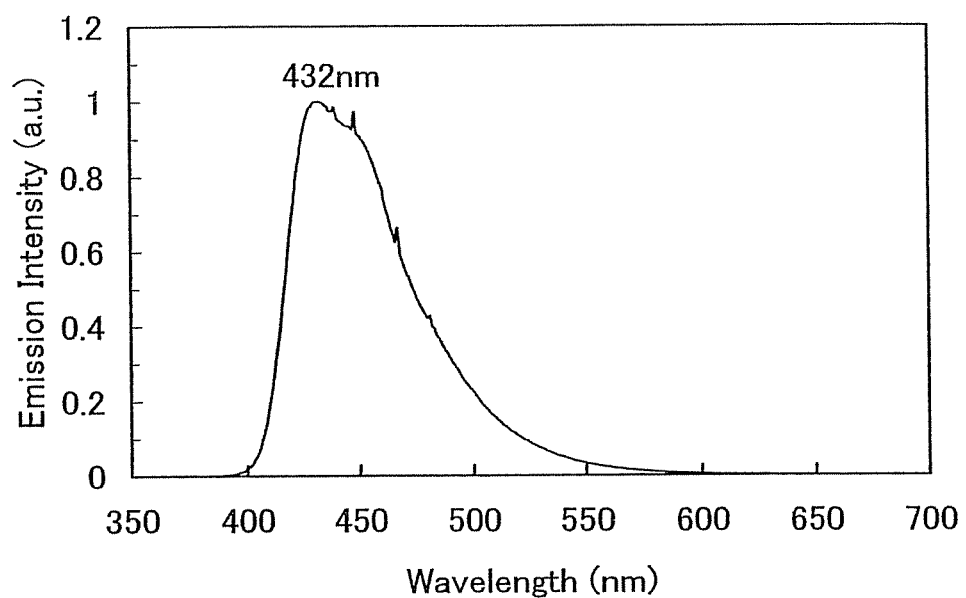
FIGS. 8A and 8B each show an emission spectrum of YGACzS.

FIG. 8A shows an emission spectrum (excitation wavelength: 370 nm) of the obtained YGACzS in toluene. In FIG. 8A, the horizontal axis indicates the wavelength (nm) and the vertical axis indicates the emission intensity (arbitrary unit). It is apparent from FIG. 8A that light emission from the YGACzS has a peak at 432 nm in the toluene solution. Further, emission color of the YGACzS in the toluene solution was visually identified as being bluish.

Figure 8B:
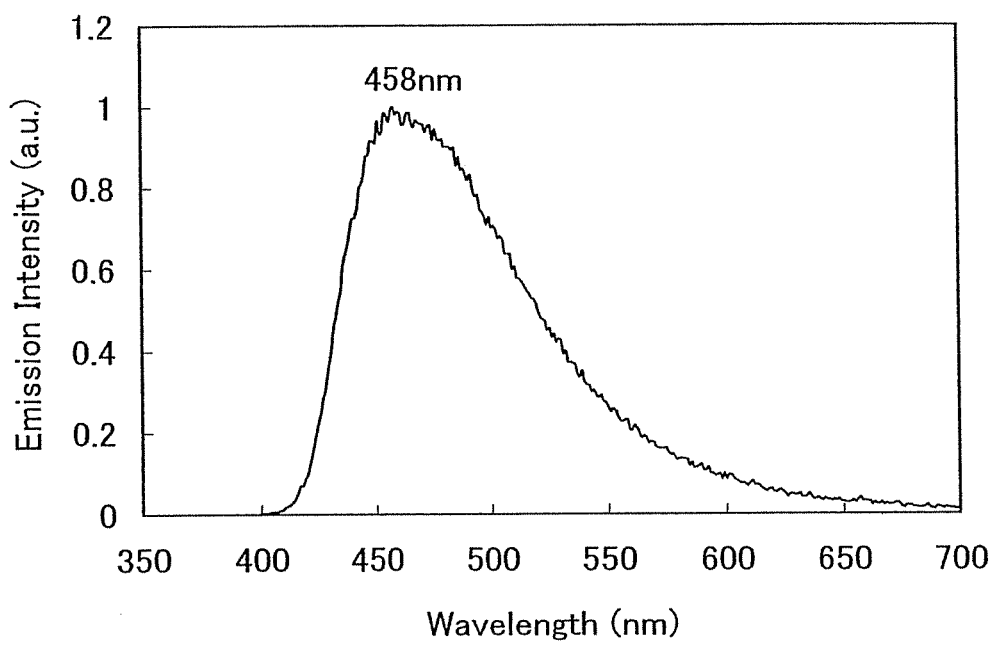

FIG. 8B shows an emission spectrum (excitation wavelength: 387 nm) in a thin film state obtained by depositing the obtained YGACzS by an evaporation method. In FIG. 8B, the horizontal axis indicates the wavelength (nm) and the vertical axis indicates the emission intensity (arbitrary unit). It is apparent from FIG. 8B that light emission from the YGACzS has a peak at 458 nm in the thin film state. Further, emission color of the YGACzS in the thin film state was able to be visually identified as being bluish. The emission spectrum was measured using a fluorescence spectrophotometer (FS920, manufactured by Hamamatsu Photonics Corporation).

The obtained YGACzS was deposited by an evaporation method, and an ionization potential of YGACzS in a thin film state was estimated to be 5.35 eV by using a photoelectron spectroscopy device (AC-2, manufactured by Riken Keiki Co., Ltd.). From the measurement result of the ionization potential, it was found that the value of the HOMO level was −5.35 eV. Further, the absorption spectrum of the compound in a thin film state was measured using an UV-visible spectrophotometer (V-550, manufactured by JASCO Corporation). The absorption edge of the longer wavelength side was obtained from a Tauc plot assuming direct transition. The LUMO level was obtained by considering the energy of the absorption edge as a band gap (2.91 eV). The LUMO level was −2.44 eV.

An oxidation reduction characteristic of the YGACzS was measured by a cyclic voltammetry (CV) technique. An electrochemical analyzer (ALS model 600A, manufactured by BAS Inc.) was used for the measurement.

The solution for the CV measurement was prepared by using dehydrated dimethylformamide (DMF) (produced by Aldrich Corp., 99.8%, catalog number: 22705-6) as a solvent, dissolving a supporting electrolyte, tetra-n-butylammonium perchlorate (n-Bu$_4$NClO$_4$) (produced by Tokyo Chemical Industry Co., Ltd., catalog number: T0836), at a concentration of 100 mmol/L, and then dissolving YGACzS which was the object of measurement at a concentration of 1 mmol/L.

A platinum electrode (a PTE platinum electrode, manufactured by BAS Inc.) was used as a working electrode, a platinum electrode (a Pt counter electrode (5 cm) for VC-3 use, manufactured by BAS Inc.) was used as an auxiliary electrode, and an Ag/Ag$^+$ electrode (an RE5 non-aqueous solvent reference electrode, manufactured by BAS Inc.) was used as a reference electrode. The measurement was performed at room temperature. A scan in which the potential of the working electrode with respect to the reference electrode was varied from 0.4 V to −0.03 V after changing it from −0.03 V to 0.4 V was regarded as one cycle, and the scan was performed for 100 cycles with respect to both the oxidation region and the reduction region. The scan rate of the CV measurement was set at 0.1 V/s.

Figure 9A:
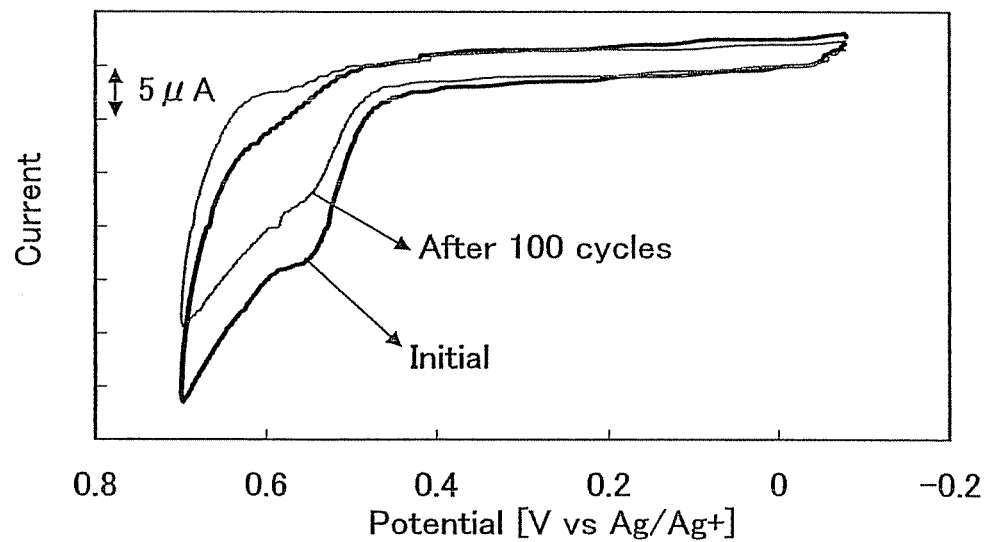
FIGS. 9A and 9B each show a result of CV measurement of YGACzS.

FIG. 9A shows results of a measurement of oxidation characteristics of the YGACzS. In FIG. 9A, the horizontal axis indicates a potential (V) of the working electrode with respect to the reference electrode, and the vertical axis indicates the amount of current (μA) flowing between the working electrode and the auxiliary electrode. It can be seen from FIG. 9A that the oxidation potential was 0.55 V (vs. Ag/Ag$^+$ electrode).

Figure 9B:
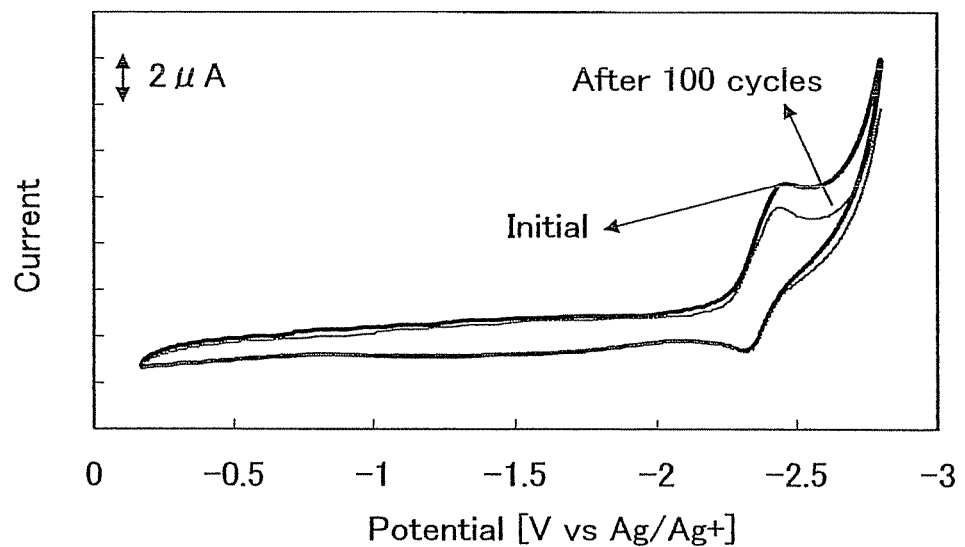

FIG. 9B shows results of a measurement of a reduction characteristic of YGACzS. In FIG. 9B, the horizontal axis indicates a potential (V) of the working electrode with respect to the reference electrode, and the vertical axis indicates a value of current (μA) flowing between the working electrode and the auxiliary electrode. It can be seen from FIG. 9B that the reduction potential was −2.44 V (vs. Ag/Ag$^+$ electrode). Although 100-cycle scans were conducted, the peak position and the peak intensity of the CV curve hardly changed. Therefore, it can be concluded that YGACzS of the present invention is very stable with respect to the repeated process between the reduction and following oxidation.

Embodiment 2

In this embodiment, a synthetic method of a stilbene derivative which is different from the stilbene derivative described in Embodiment 1 is described.

In this embodiment, an example of a synthetic method of (E)-4-{N-[4-(9H-carbazol-9-yl)phenyl]-N-phenyl}amino-4'-diphenylaminostilbene (hereinafter, abbreviated as "YGA-DPhAS") which is an example of a stilbene derivative, is described. A synthetic scheme of the substance is shown in the following Steps 1 to 4.

Step 1; Synthesis of 4-bromobenzyl triphenylphosphonium bromide

First, 25.2 g (101 mmol) of 4-bromobenzyl bromide and 100 mL of acetone were placed in a 200 mL conical flask, and 29.1 g (111 mmol) of triphenylphosphine was added thereto. This reaction mixture was stirred at room temperature for 23 hours. After the completion of the reaction, the precipitate in the reaction mixture was collected by suction filtration. 50.5 g of a white powdered solid, 4-bromobenzyl triphenylphosphonium bromide, which was the target substance, was obtained in a yield of 97.6%. A synthetic scheme (b-1) of 4-bromobenzyl triphenylphosphonium bromide is shown below.

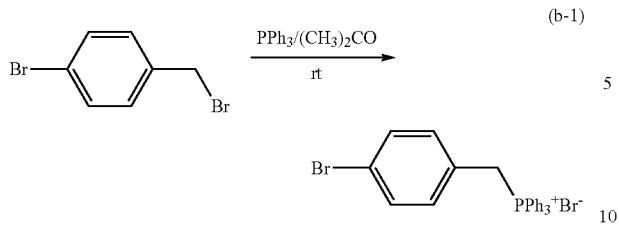

(b-1)

Step 2; Synthesis of
(E)-4-bromo-4'-(N,N-diphenyl)aminostilbene

Next, 5.77 g (11.3 mmol) of 4-bromobenzyl triphenylphosphonium bromide obtained in Step 1 and 3.08 g (11.3 mmol) of 4-(N,N-diphenyl)amino benzaldehyde were placed into a 300 mL three-neck flask, and nitrogen substitution was carried out in the three-neck flask. Then, 50 mL of tetrahydrofuran (THF) was added to this mixture. Further, a suspension in which 1.26 g (11.3 mmol) of potassium tert-butoxide was mixed in 30 mL of THF was dropped to this mixture.

After the completion of the drop, the reaction mixture was stirred at room temperature for 24 hours. After the completion of the reaction, water was added to the reaction mixture, and the precipitate was collected by suction filtration. 1.50 g of a light yellow powdered solid, (E)-4-bromo-4'-(N,N-diphenyl) aminostilbene], which was the target substance, was obtained in a yield of 31.2%. It was confirmed that (Z)-4-bromo-4'-(N,N-diphenyl)aminostilbene] was contained in the filtrate obtained by the suction filtration. A synthetic scheme (b-2) of (E)-4-bromo-4'-(N,N-diphenyl)aminostilbene is shown below.

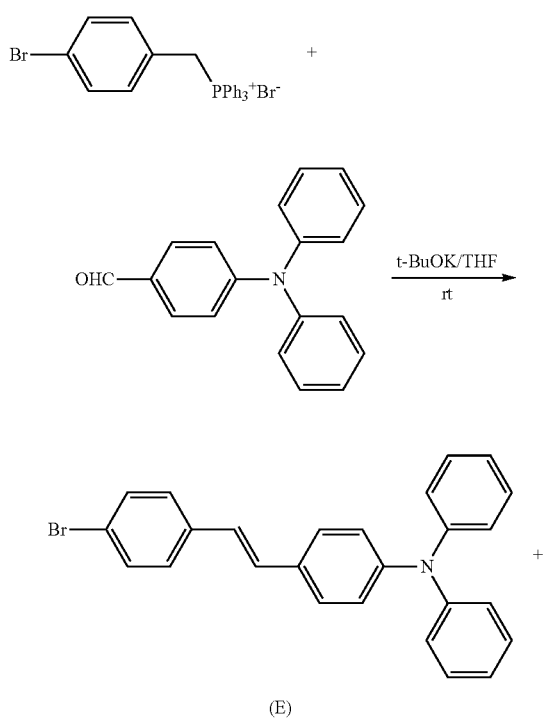

(b-2)

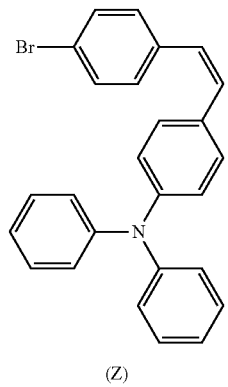

(Z)

Step 3; Synthesis of N-[4-(9H-carbazol-9-yl)]phenyl-N-phenylamine (YGA)

YGA is the same as the substance described in Step 3 of Embodiment 1; therefore, its synthesis will not be described here.

Step 4; Synthesis of (E)-4-{N-[4-(9H-carbazol-9-yl)phenyl]-N-phenyl}amino-4'-diphenylaminostilbene (YGADPhAS)

Next, 1.0 g (2.4 mmol) of (E)-4-bromo-4'-(N,N-diphenyl)aminostilbene obtained in Step 2, 0.86 g (2.6 mmol) of N-[4-(9H-carbazol-9-yl)]phenyl-N-phenylamine (YGA) obtained in Step 3, 0.067 g (0.12 mmol) of bis(dibenzylideneacetone)palladium(0), and 1.1 g (12 mmol) of sodium tert-butoxide were placed in a 100 mL three-neck flask, and nitrogen substitution was carried out in the three-neck flask.

20 mL of toluene and 0.10 g (0.047 mmol) of tri-tert-butylphosphine (10% hexane solution) were added to this mixture. This reaction mixture was stirred at 80° C. for 6 hours. After the completion of the reaction, the reaction solution was washed with water, and the aqueous phase was extracted with ethyl acetate. The extracted solution combined with the organic phase was dried with magnesium sulfate. After the drying, this mixture was subjected to suction filtration and the filtrate was concentrated. The obtained solid was dissolved in toluene, and the resulting solution was subjected to suction filtration through Florisil, celite, and alumina.

The filtrate was concentrated, and the obtained solid was recrystallized with a mixed solvent of chloroform and hexane. 0.26 g of a yellow powdered solid, which was the target substance, was obtained in a yield of 16%. This compound was identified by a nuclear magnetic resonance method (NMR) as (E)-4-{N-[4-(9H-carbazol-9-yl)phenyl]-N-phenyl}amino-4'-diphenylaminostilbene (abbreviation: YGADPhAS). A synthetic scheme (b-3) of YGADPhAS is shown below.

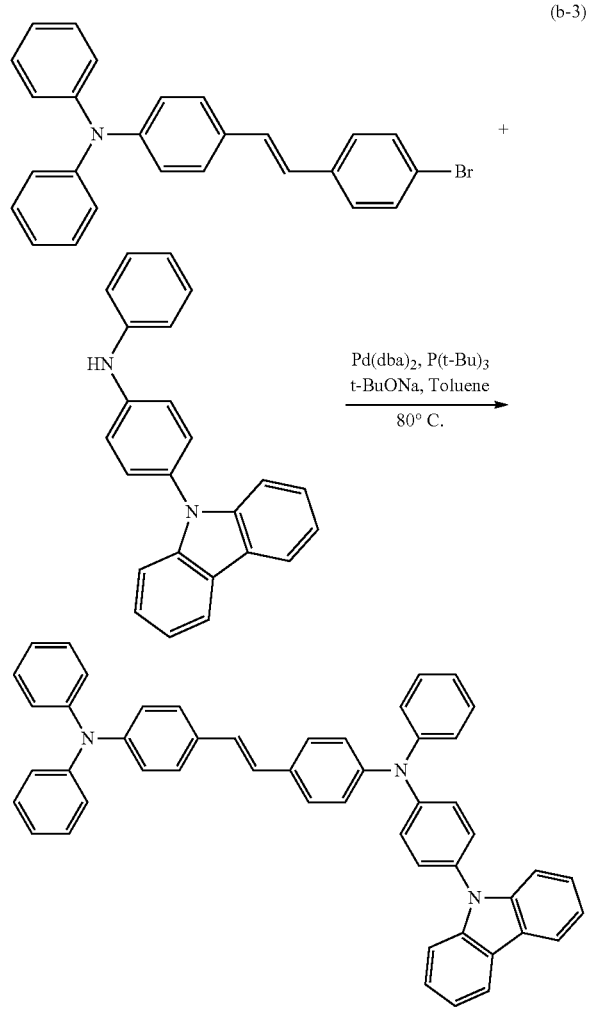

Figure 10A:
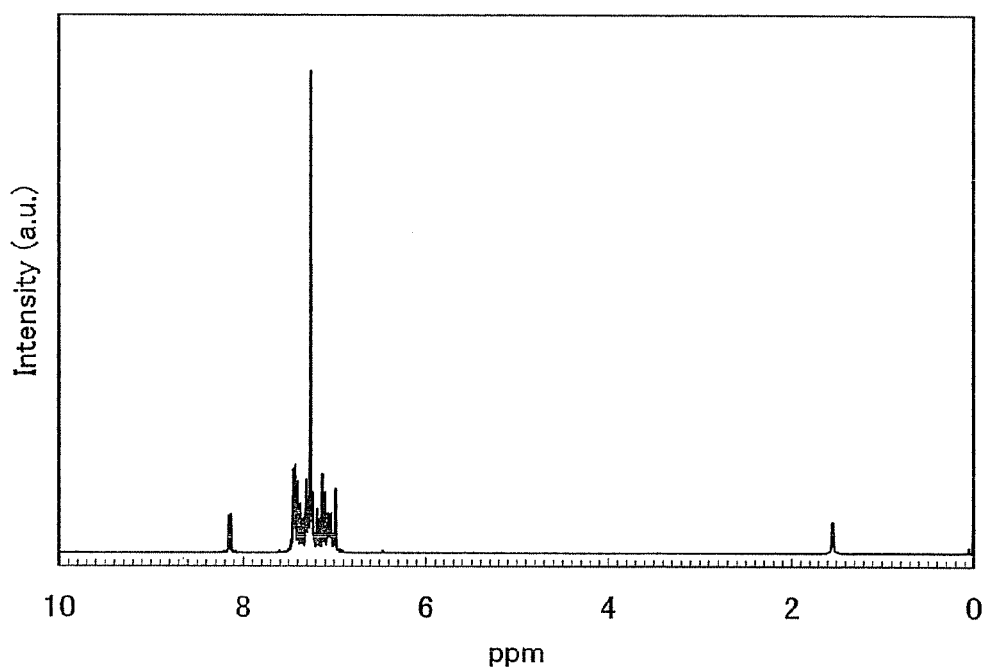
FIGS. 10A and 10B each show a $^1$H NMR chart of (E)-4-{N-[4-(9H-carbazol-9-yl)phenyl]-N-phenyl}amino-4'-diphenylaminostilbene (Abbreviation: YGADPhAS)
Figure 10B:
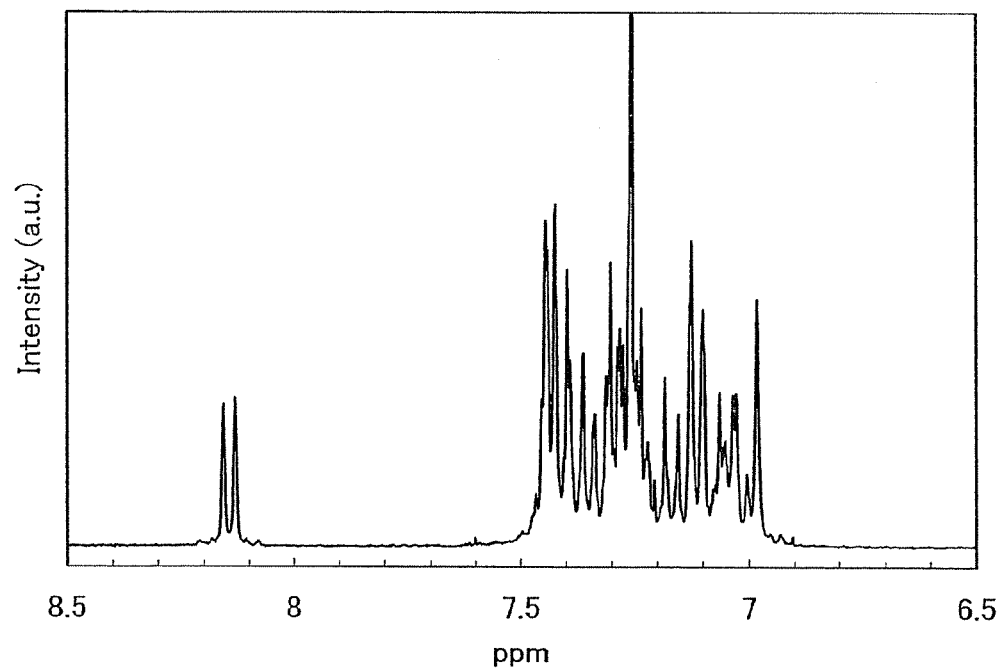

¹H NMR data of the obtained YGADPhAS is shown below. FIGS. 10A and 10B are each a ¹H NMR chart, and FIG. 10B is an enlarged chart of the 6.5 ppm to 8.5 ppm range in FIG. 10A.

¹H NMR (CDCl$_3$, 300 MHz): δ=6.98-7.45 (m, 35H), 8.14 (d, J=7.2 Hz, 2H)

Thermogravimetry-differential thermal analysis (TG-DTA) was performed on the obtained YGADPhAS. The measurement performed using a thermogravimetric/differential thermal analyzer (TG/DTA 320, manufactured by Seiko Instruments Inc.) revealed that the temperature of 5% weight loss is 415.8° C., which means that the YGADPhAS is a material having good heat resistance.

Figure 11A:
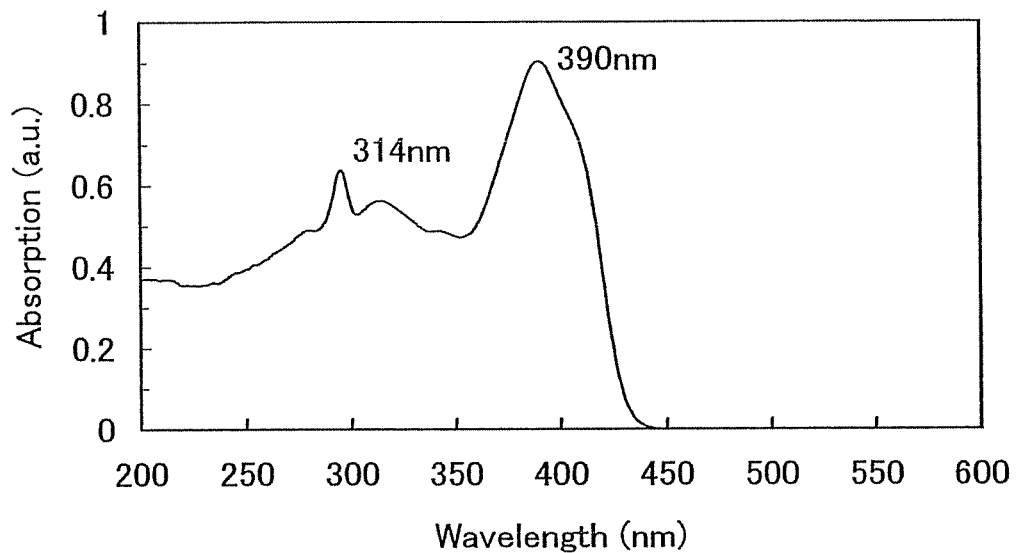
FIGS. 11A and 11B each show an absorption spectrum of YGADPhAS.

FIG. 11A shows an absorption spectrum of YGADPhAS in toluene. In FIG. 11A, the horizontal axis indicates the wavelength (nm) and the vertical axis indicates the absorption intensity (arbitrary unit).

Figure 11B:
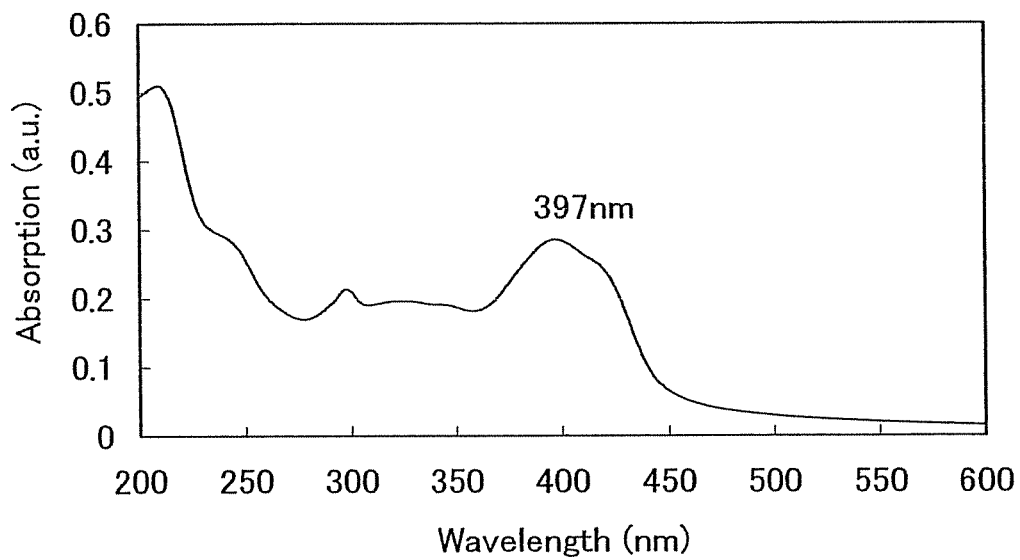

FIG. 11B shows an absorption spectrum in a thin film state obtained by depositing the obtained YGADPhAS by an evaporation method. In FIG. 11B, the horizontal axis indicates the wavelength (nm) and the vertical axis indicates the absorption intensity (arbitrary unit). The absorption spectra were measured using an ultraviolet-visible spectrophotometer (V-550, manufactured by JASCO Corporation).

Figure 12A:
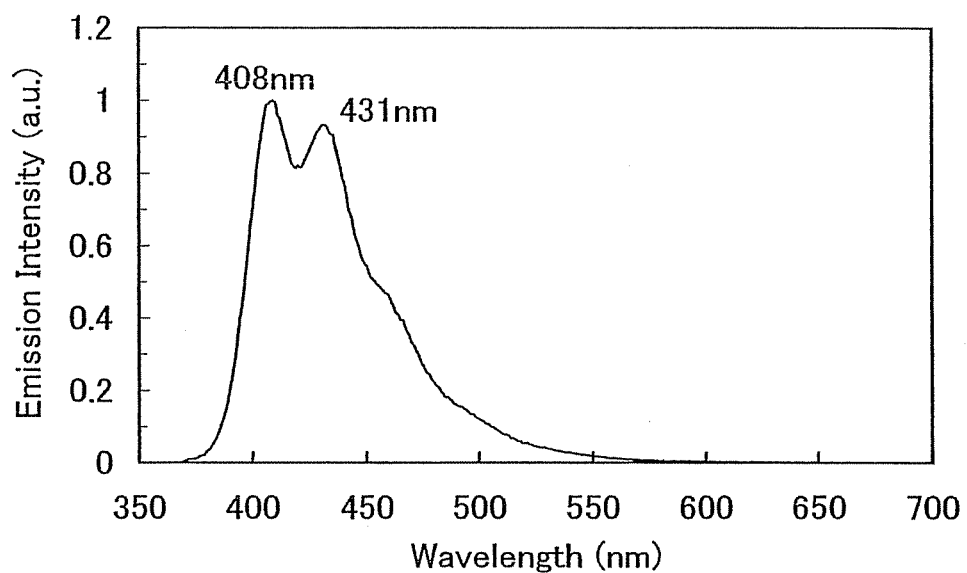
FIGS. 12A and 12B each show an emission spectrum of YGADPhAS.

FIG. 12A shows an emission spectrum (excitation wavelength: 390 nm) of a toluene solution of the obtained YGADPhAS. In FIG. 12A, the horizontal axis indicates the wavelength (nm) and the vertical axis indicates the emission intensity (arbitrary unit). It is apparent from FIG. 12A that light emission from the YGADPhAS has peaks at 408 nm and 431 nm in the toluene solution. Further, emission color of the YGADPhAS in the toluene solution was visually identified as being bluish.

Figure 12B:
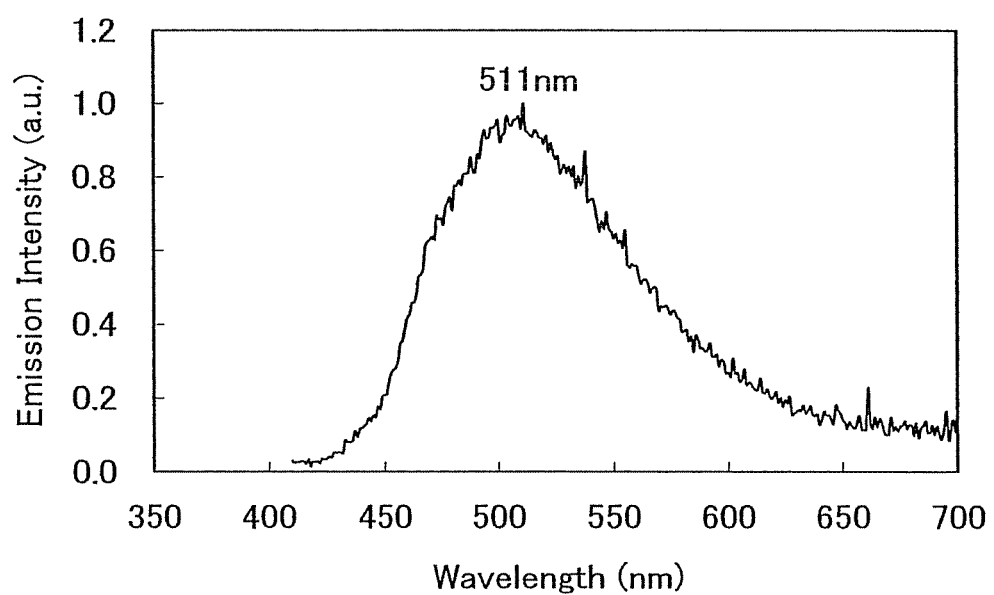

FIG. 12B shows an emission spectrum (excitation wavelength: 397 nm) in the thin film state obtained by depositing the obtained YGADPhAS by an evaporation method. In FIG. 12B, the horizontal axis indicates the wavelength (nm) and the vertical axis indicates the emission intensity (arbitrary unit). It is apparent from FIG. 12B that light emission from the YGADPhAS has a peak at 511 nm in the thin film state. Further, emission color of the YGADPhAS in the thin film state was visually identified as being bluish. The emission spectra were measured using a fluorescence spectrophotometer (FS920, manufactured by Hamamatsu Photonics Corporation).

The obtained YGADPhAS was deposited by an evaporation method, and an ionization potential of the compound in a thin film state was measured using a photoelectron spectroscopy device (AC-2, manufactured by Riken Keiki Co., Ltd.). The measurement result was 5.22 eV, which means that the value of the HOMO level was −5.22 eV. Further, the absorption spectrum of the compound in a thin film state was measured using a UV-visible spectrophotometer (V-550, manufactured by JASCO Corporation). The absorption edge on the longer wavelength side was obtained from a Tauc plot assuming direct transition. The LUMO level was obtained by considering the energy of the absorption edge as a band gap (2.82 eV). The LUMO level was −2.40 eV.

Subsequently, oxidation characteristics of the YGADPhAS were measured by a cyclic voltammetry (CV) technique. An electrochemical analyzer (ALS model 600A, manufactured by BAS Inc.) was used for the measurement.

The solution for the CV measurement was prepared by using dehydrated dimethylformamide (DMF) (produced by Aldrich Corp., 99.8%, catalog number: 22705-6) as a solvent, dissolving a supporting electrolyte of tetra-n-butylammonium perchlorate (n-Bu$_4$NClO$_4$) (produced by Tokyo Chemical Industry Co., Ltd., catalog number: T0836) at a concentration of 100 mmol/L, and then dissolving the YGADPhAS which was the object of measurement at a concentration of 1 mmol/L.

A platinum electrode (PTE platinum electrode, manufactured by BAS Inc.) was used as a working electrode, a platinum electrode (Pt counter electrode (5 cm) for VC-3 use, manufactured by BAS Inc.) was used as an auxiliary electrode, and an Ag/Ag$^+$ electrode (RE5 non-aqueous solvent reference electrode, manufactured by BAS Inc.) was used as a reference electrode. The measurement was performed at room temperature. A scan in which the potential of the working electrode with respect to the reference electrode was varied from 0.4 V to −0.03 V after being changed from −0.03 V to 0.4 V was regarded as one cycle, and the scan was performed for 100 cycles. The scan rate of the CV measurement was 0.1 V/s.

Figure 13A:
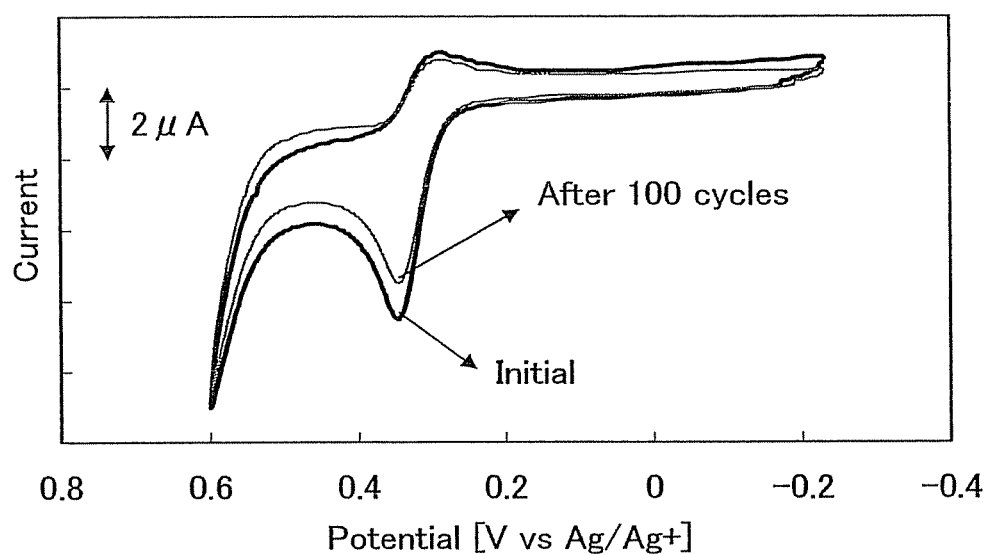
FIGS. 13A and 13B each show a result of CV measurement of YGADPhAS.
Figure 13B:
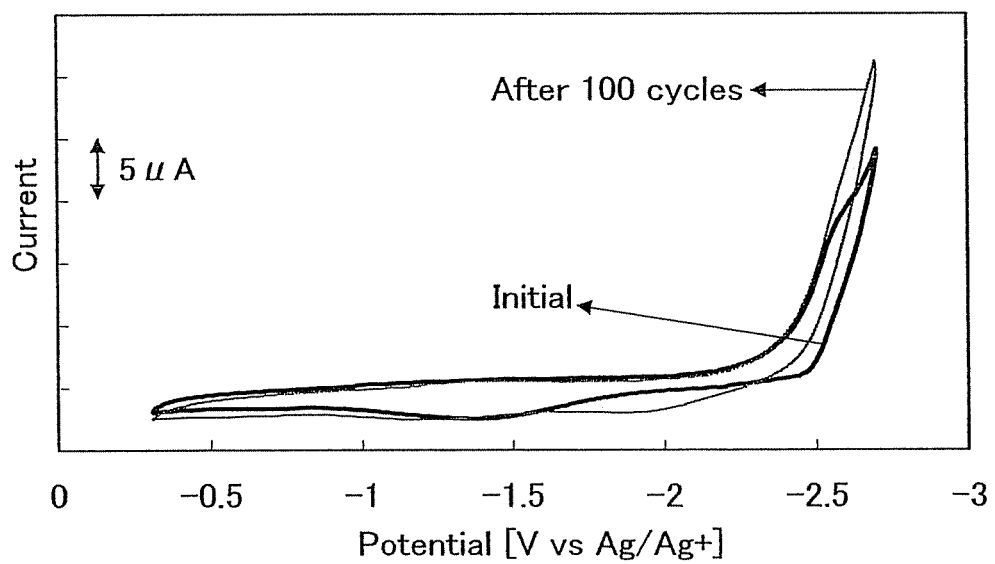

FIG. 13A and FIG. 13B show the results of the measurement of the oxidation characteristics and reduction characteristics of the YGADPhAS, respectively. In FIG. 13, the horizontal axis indicates a potential (V) of the working electrode with respect to the reference electrode, and the vertical axis indicates the amount of current (μA) flowing between the working electrode and the auxiliary electrode. From FIG. 13, it can be seen that the oxidation potential was 0.34 V (vs. Ag/Ag$^+$ electrode). Despite the fact that the scan was repeated for 100 cycles, the peak position and the peak intensity of the CV curve hardly change before and after the measurement. Thus, it was concluded that YGADPhAS of the present invention is very stable with respect to the repeated process between the oxidation and following reduction.

Embodiment 3

In this embodiment, a synthetic method of N-{4-[(E)-4-(9H-carbazol-9-yl)styryl]phenyl}-N,9-diphenyl-9H-carbazol-3-amine represented by the following structure (hereinafter, abbreviated as "PCACzS") in which $A^{11}$ corresponds to the general formula (1-2) of the general formula (3) is shown.

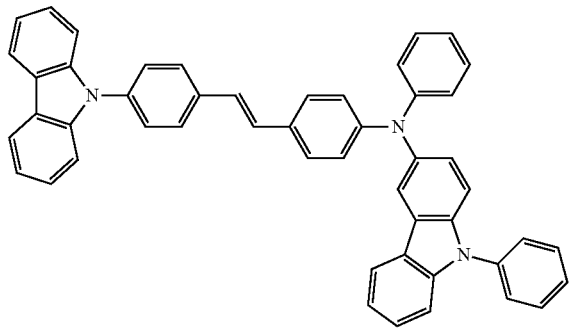

First, (E)-4-bromo-4'-(9H-carbazol-9-yl)stilbene was synthesized in accordance with the synthetic schemes (a-1) and (a-2) shown in Embodiment 1. Then, in a 50 mL three-neck flask, 620 mg (1.5 mmol) of (E)-4-bromo-4'-(9H-carbazol-9-yl)stilbene; 500 mg (1.5 mmol) of N,9-diphenyl-9H-carbazol-3-amine (abbreviation: PCA); 55 mg (0.1 mmol) of bis(dibenzylideneacetone)palladium(0); and a suspension of 200 mg (2.0 mmol) of sodium tert-butoxide, 15 mL of dehydrated xylene, and 600 μL (0.3 mmol) of tri-tert-butylphosphine (10% hexane solution) were heated and stirred at 110° C. for 11 hours under a nitrogen atmosphere.

After the completion of the reaction, approximately 200 mL of toluene was added to this suspension, and the mixture was subjected to suction filtration through Florisil, alumina, and celite. The obtained filtrate was washed with water and dried with magnesium sulfate. This suspension was filtered through Florisil, alumina, and celite, and the obtained filtrate was concentrated. This concentrate was subjected to silica gel column chromatography (a developing solvent was a mixed solvent of toluene and hexane), and the target substance was obtained. The obtained target substance was recrystallized with an acetate:hexane mixed solvent.

140 mg of N-{4-[(E)-4-(9H-carbazol-9-yl)styryl]phenyl}-N,9-diphenyl-9H-carbazol-3-amine (abbreviation: PCACzS), a yellow powder which was the target substance, was obtained in a yield of 14%. Rf values in silica gel thin layer chromatography (TLC) (in the developing solvent, hexane:ethyl acetate=10:1) were as follows: the target substance was 0.43, (E)-4-bromo-4'-(9H-carbazol-9-yl)stilbene was 0.60, and PCA was 0.35.

Figure 26A:
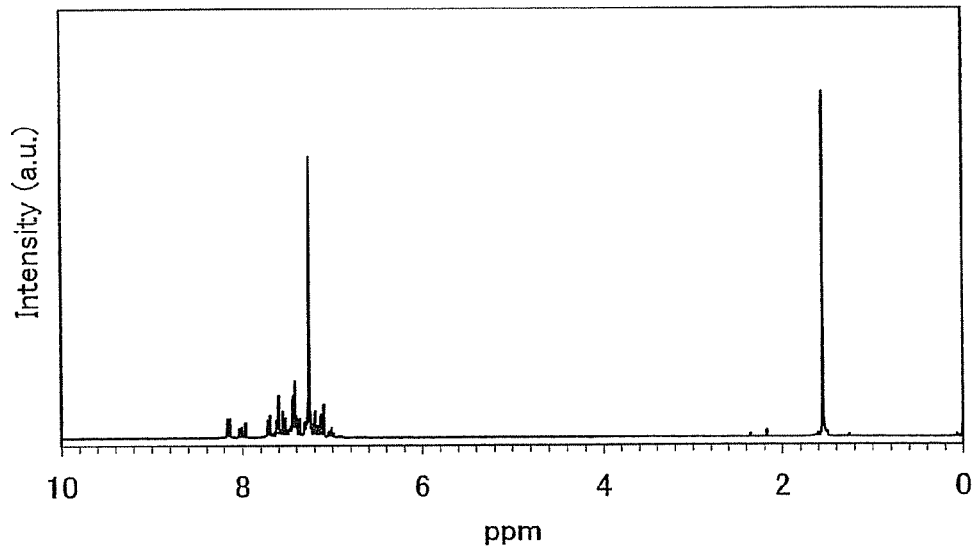
FIGS. 26A and 26B each show a $^1$H NMR chart of N-{4-[(E)-4-(9H-carbazol-9-yl)styryl]phenyl}-N,9-diphenyl-9H-carbazol-3-amine (Abbreviation: PCACzS)
Figure 26B:
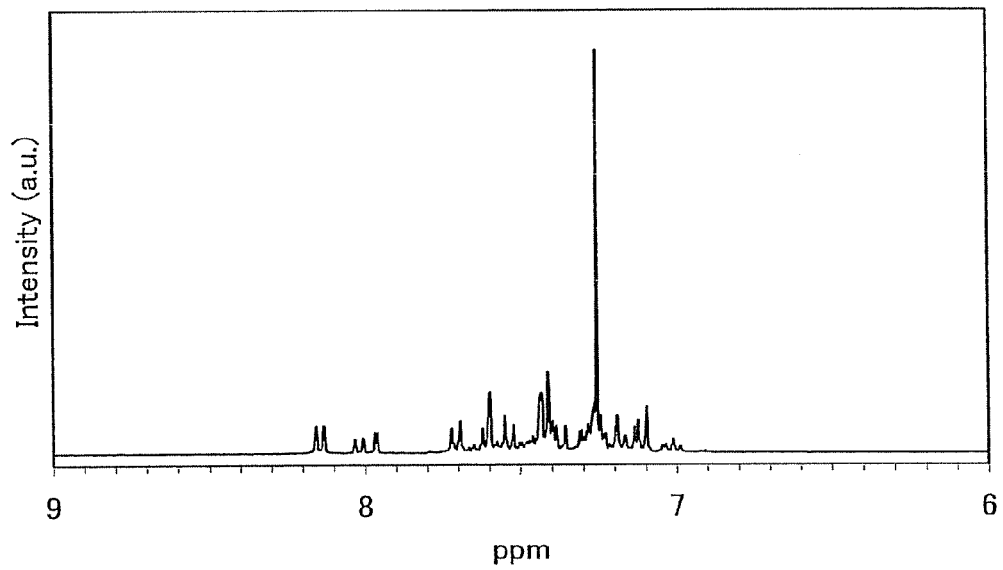

$^1$H NMR data is shown below. FIGS. 26A and 26B are each a $^1$H NMR chart, and FIG. 26B is an enlarged chart of the 6 ppm to 9 ppm range in FIG. 26A.

$^1$H NMR (CDCl$_3$, 300 MHz): δ=6.99-7.72 (m, 31H), 7.96 (d, J=2.4 Hz, 1H), 8.02 (d, J=7.8 Hz, 1H), 8.15 (d, J=7.3 Hz, 2H)

Figure 27:
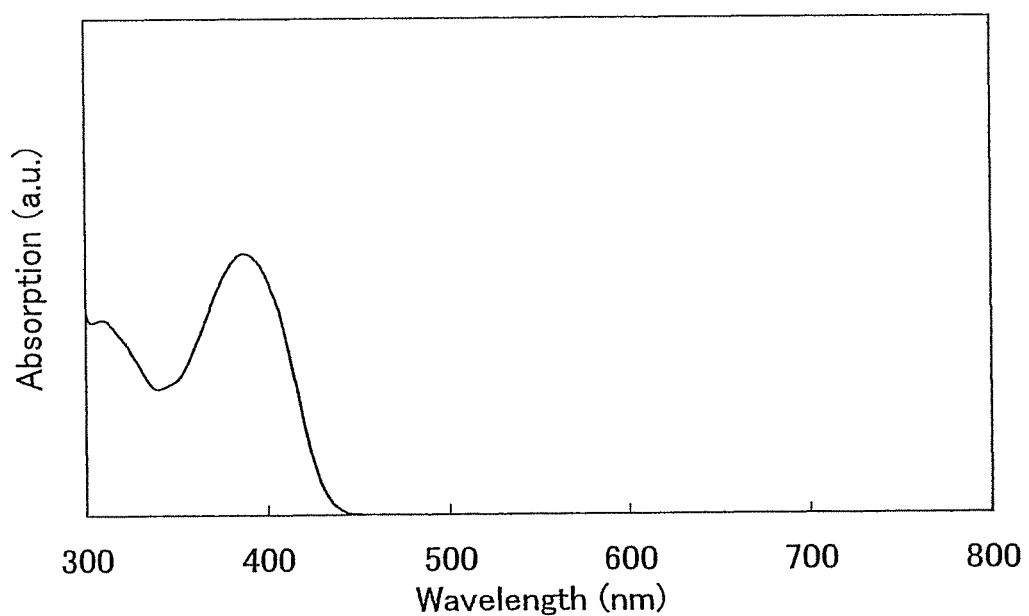
FIG. 27 shows an absorption spectrum of PCACzS.

FIG. 27 shows an absorption spectrum of PCACzS in toluene. The horizontal axis indicates the wavelength (nm) and the vertical axis indicates the absorption intensity (arbitrary unit). The sample solution was put into a quartz cell, and measurement was carried out by using an ultraviolet-visible spectrophotometer (V-550, manufactured by JASCO Corporation). A spectrum in which absorption spectra of the quartz and toluene are abstracted from an absorption spectrum of the sample is shown in FIG. 27.

Figure 28:
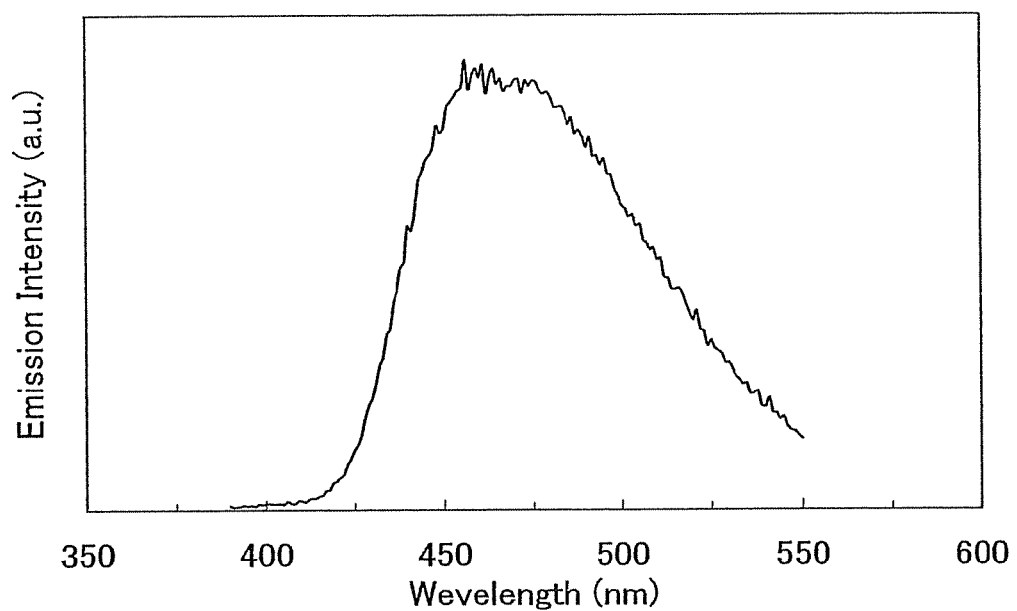
FIG. 28 shows an emission spectrum of PCACzS.

FIG. 28 shows an emission spectrum of PCACzS in toluene. In FIG. 28, the horizontal axis indicates the wavelength (nm) and the vertical axis indicates the emission intensity (arbitrary unit). It was found that light emission had emission peaks at 460 nm and 473 nm in the toluene solution (excitation light was 375 nm). Further, emission color in the toluene solution was visually identified as being bluish. The emission spectrum was measured using a fluorescence spectrophotometer (FS920, manufactured by Hamamatsu Photonics Corporation).

Thermogravimetry-differential thermal analysis (TG-DTA) was performed on PCACzS using a high vacuum differential type differential thermal balance (type DTA2410SA, manufactured by Bruker AXS K. K.). The measurement performed under atmospheric air showed the temperature of 5% weight loss at 455° C., which means that the YGACzS has good heat resistance.

Embodiment 4

In this embodiment, a synthetic method of N-{4-[(E)-4-(diphenylamino)styryl]phenyl}-N,N',N'-triphenyl-1,4-phenylenediamine represented by the following structure (hereinafter, abbreviated as "DPAPhAS") in which $A^{11}$ corresponds to the general formula (1-1) of the general formula (1) is shown.

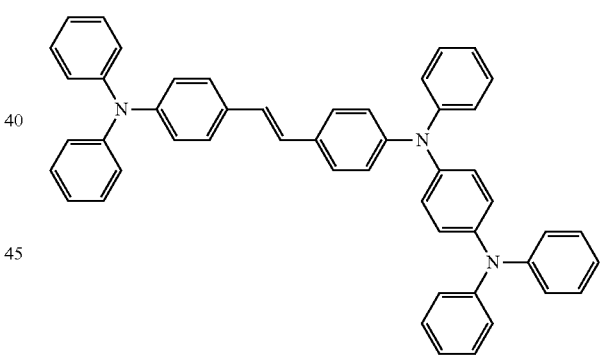

First, (E)-4-bromo-4'-(N,N-diphenyl)aminostilbene was synthesized in accordance with synthetic schemes (b-1) and (b-2) shown in Embodiment 2. Then, in a 50 mL three-neck flask, 490 mg (1.2 mmol) of (E)-4-bromo-4'-(N,N-diphenyl)aminostilbene; 400 mg (1.2 mmol) of N,N,Y-triphenyl-1,4-phenylenediamine (abbreviation: DPA); 55 mg (0.1 mmol) of bis(dibenzylideneacetone)palladium(0); and a suspension of 200 mg (2.0 mmol) of sodium tert-butoxide, 15 mL of dehydrated xylene, and 600 μL (0.3 mmol) of tri-tert-butylphosphine (10% hexane solution) were heated and stirred at 110° C. for 7 hours under a nitrogen atmosphere.

After the completion of the reaction, approximately 200 mL of toluene was added to this suspension, and the mixture was subjected to suction filtration through Florisil, alumina, and celite. The obtained filtrate was washed with water and dried with magnesium sulfate. This suspension was filtered through Florisil, alumina, and celite, and the obtained filtrate was concentrated. This concentrate was subjected to silica gel column chromatography (a developing solvent was a mixed solution of toluene and hexane), and the target substance was obtained. The obtained target substance was recrystallized with an acetate:hexane mixed solvent.

480 mg of N-{4-[(E)-4-(diphenylamino)styryl]phenyl}-N,N',N'-triphenyl-1,4-phenylenediamine (abbreviation: DPAPhAS), a yellow powder which was the target substance, was obtained in a yield of 59%. Rf values in silica gel thin layer chromatography (TLC) (in the developing solvent, hexane:ethyl acetate=10:1) were as follows: the target substance was 0.45, (E)-4-bromo-4'-(N,N-diphenyl)aminostilbene was 0.55, and DPA was 0.34.

Figure 29A:
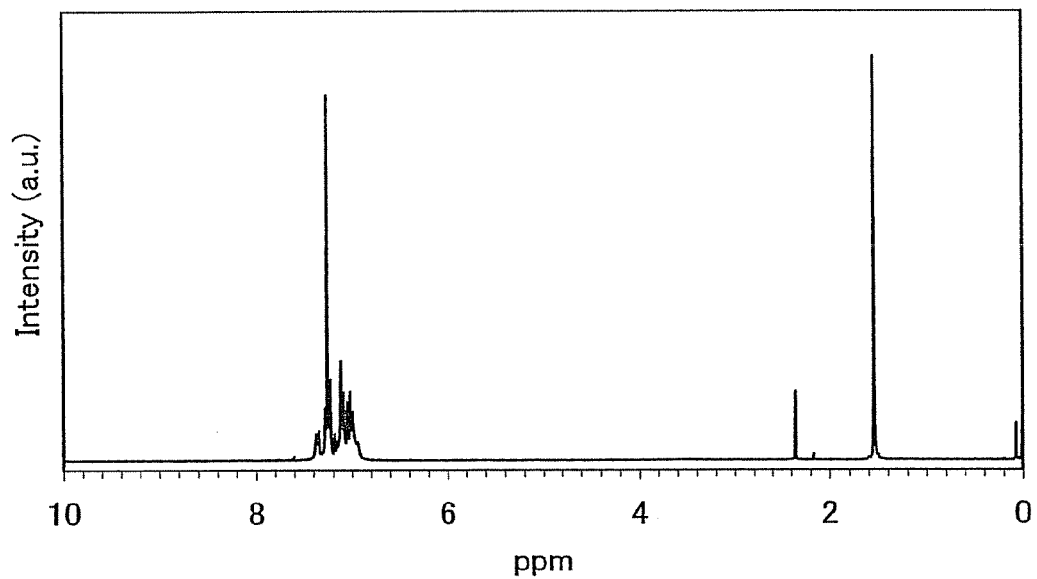
FIGS. 29A and 29B each show a $^1$H NMR chart of N-{4-[(E)-4-(diphenylamino)styryl]phenyl}-N,N',N'-triphenyl-1,4-phenylenediamine (Abbreviation: DPAPhAS)
Figure 29B:
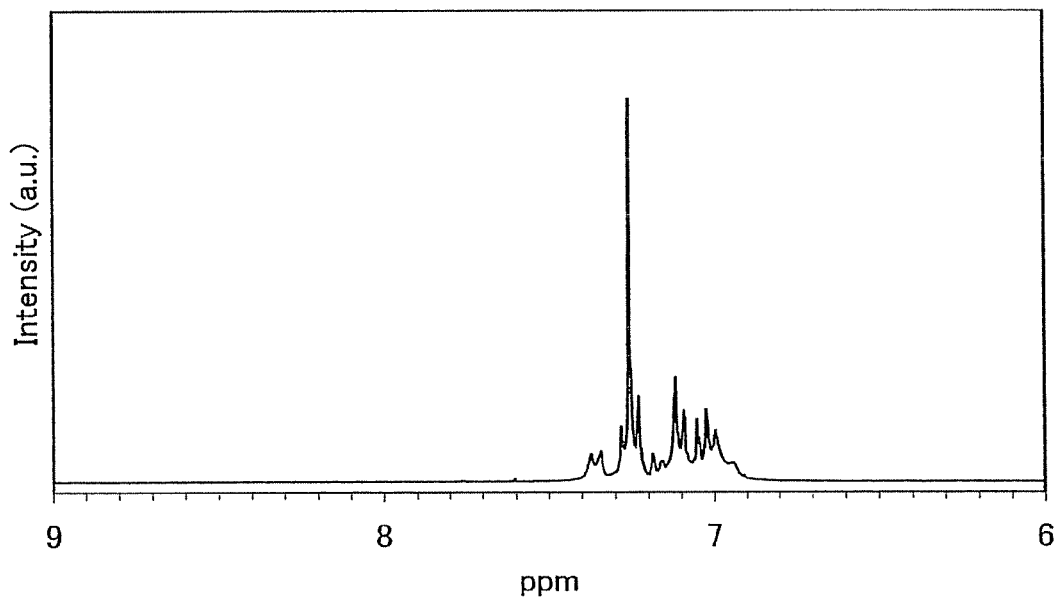

$^1$H NMR data is shown below. FIGS. 29A and 29B are each a $^1$H NMR chart, and FIG. 29B is an enlarged chart of the 6 ppm to 9 ppm range in FIG. 29A.

$^1$H NMR (CDCl$_3$, 300 MHz): δ=6.93 (s, 2H), 6.98-7.27 (m, 33H), 7.35 (d, J=8.4 Hz, 4H)

Figure 30:
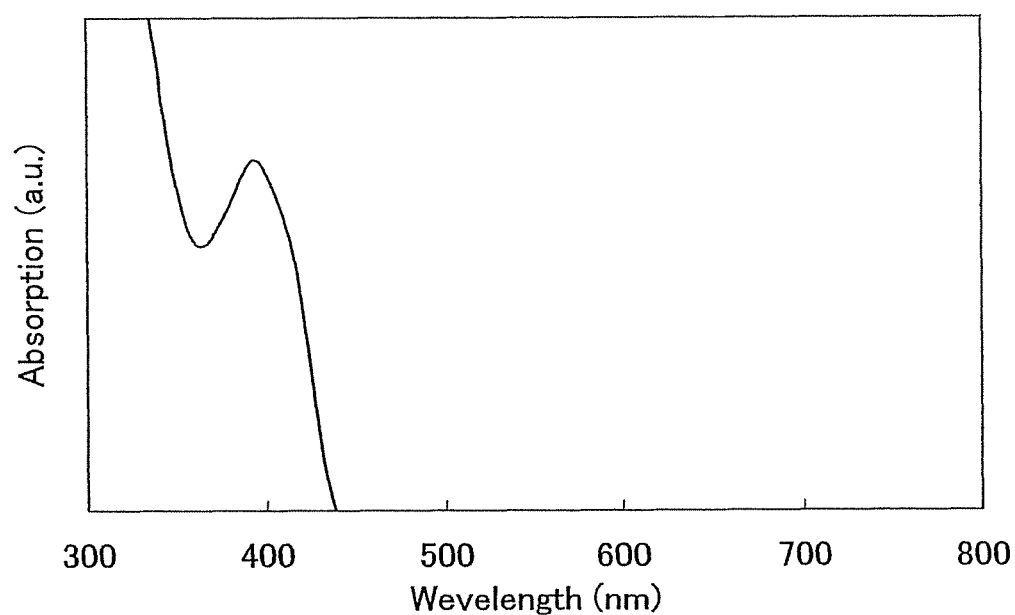
FIG. 30 shows an absorption spectrum of DPAPhAS.

FIG. 30 shows an absorption spectrum of DPAPhAS in toluene. The horizontal axis indicates the wavelength (nm) and the vertical axis indicates the absorption intensity (arbitrary unit). The sample solution was put into a quartz cell, and the measurement was conducted by using an ultraviolet-visible spectrophotometer (V-550, manufactured by JASCO Corporation) A spectrum in which absorption spectra of the quartz and toluene are abstracted from an absorption spectrum of the sample is shown in FIG. 30.

Figure 31:
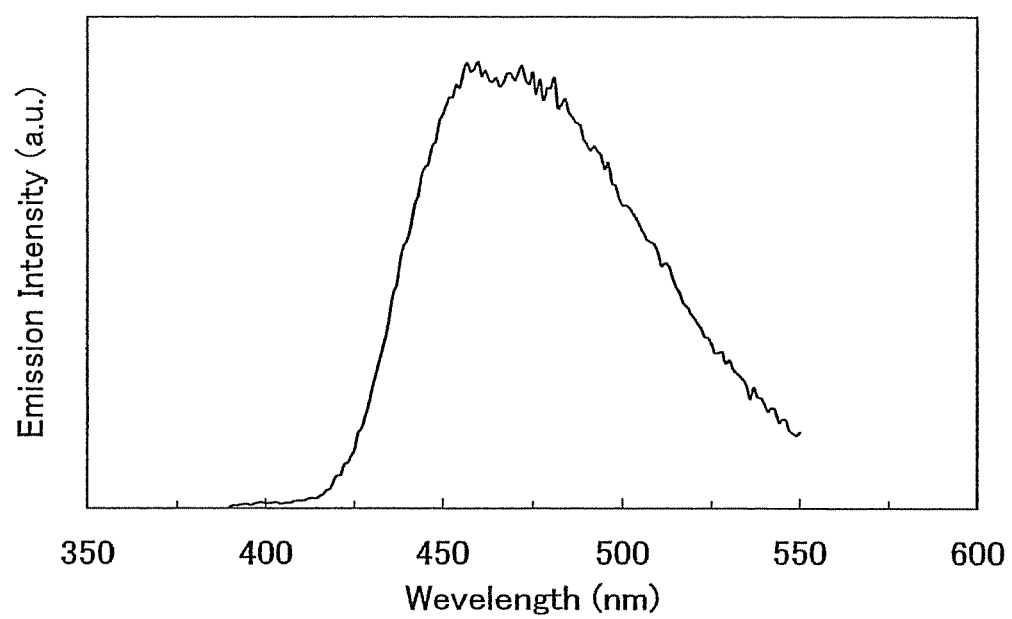
FIG. 31 shows an emission spectrum of DPAPhAS.

FIG. 31 shows an emission spectrum of DPAPhAS in toluene obtained by using a fluorescence spectrophotometer (FS920, manufactured by Hamamatsu Photonics Corporation). The horizontal axis indicates the wavelength (nm) and the vertical axis indicates the emission intensity (arbitrary unit). It was found that light emission had emission peaks at 460 nm and 472 nm in the toluene solution (excitation light was 375 nm). Further, emission color in the toluene solution was visually identified as being bluish.

Thermogravimetry-differential thermal analysis (TG-DTA) was performed on DPAPhAS using a high vacuum differential type differential thermal balance (type DTA2410SA, manufactured by Bruker AXS K. K.). The measurement performed under atmospheric air demonstrated that the 5% weight loss temperature was 434° C., which means that the DPAPhAS has good heat resistance. The measurement was performed Embodiment 5

In this embodiment, a method for manufacturing a light-emitting element in which (E)-4-{N-[4-(9H-carbazol-9-yl)phenyl]-N-phenyl}amino-4'-(9H-carbazol-9-yl)stilbene (YGACzS) prepared by the synthetic method described in Embodiment 1 is used for a part (a dopant) of a light-emitting layer is described.

First, a first electrode was formed over a substrate. In this embodiment, a glass substrate was used as the substrate. As a material for the first electrode, ITSO (indium tin oxide including silicon oxide which was obtained by a sputtering method using a target in which silicon oxide of 2 to 10 weight % was included in ITO) which is a transparent conductive film was used. After the ITSO was formed to have a thickness of 110 nm by a sputtering method, the shape of the first electrode was made to be a square of 2 mm×2 mm by etching.

Then, as pretreatment for forming the light-emitting element over the first electrode, a surface of the substrate was washed with a porous resin (typically made of PVA (polyvinyl alcohol), nylon, or the like), and after that, heat treatment was performed at 200° C. for 1 hour under atmospheric air and UV ozone treatment was performed for 370 seconds. Further, heat treatment was performed at 170° C. for 30 minutes under reduced pressure.

Subsequently, a layer including a luminescent substance was formed over the first electrode. The layer including a luminescent substance in this embodiment had a structure in which a hole injecting layer, a hole transporting layer, a light-emitting layer, an electron transporting layer, and an electron injecting layer were sequentially stacked by a vacuum evaporation method.

First, the hole injecting layer was formed over the first electrode. The hole injecting layer was formed by co-evaporation of 4,4'-bis[N-(1-naphthyl)-N-phenylamino]biphenyl (abbreviation: NPB) and molybdenum oxide so that a weight ratio of the NPB to the molybdenum oxide was 4:1. The hole injecting layer was formed to have a thickness of 50 nm.

Subsequently, the hole transporting layer was formed over the hole injecting layer. The hole transporting layer was formed by evaporation of NPB. The hole transporting layer was formed to have a thickness of 10 nm.

The light-emitting layer was formed over the hole transporting layer. The light-emitting layer was formed by co-evaporation of 4,4'-di(N-carbazolyl)biphenyl (abbreviation: CBP) and YGACzS which is a stilbene derivative of the present invention so that a weight ratio of the CBP to the YGACzS was 1:0.05. The light-emitting layer was formed to have a thickness of 30 nm.

Subsequently, the electron transporting layer was formed over the light-emitting layer. The electron transporting layer was formed by evaporation of bathocuproine (abbreviation: BCP). The electron transporting layer was formed to have a thickness of 10 nm.

Then, the electron injecting layer was formed over the electron transporting layer. The electron injecting layer was formed by co-evaporation of Alq$_3$ and lithium so that a weight ratio of the Alq$_3$ to the lithium was 1:0.01. The electron injecting layer was formed to have a thickness of 20 nm.

NPB, CBP, BCP, and Alq$_a$ used for forming the layer including a luminescent substance in this embodiment are shown below.

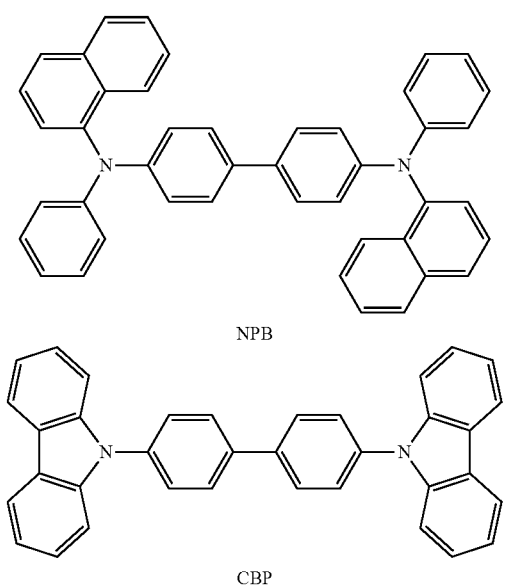

NPB

CBP

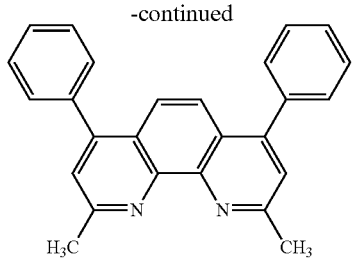

BCP

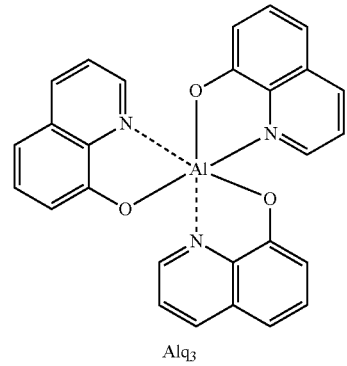

Alq₃

Then, a second electrode was formed over the electron injecting layer. The second electrode was formed by vacuum evaporation of Al. The second electrode was formed to have a thickness of 200 nm.

According to the above-described procedure, the light-emitting element was manufactured. It is to be noted that the light-emitting element is preferably prevented from being exposed to atmospheric air because deterioration of the light-emitting element is promoted when it is exposed to atmospheric air. Therefore, in this embodiment, sealing was performed using a sealing substrate under a nitrogen atmosphere.

The light-emitting element manufactured as described above was driven by applying voltage to the light-emitting element, and characteristics of the light-emitting element were measured. The light-emitting element manufactured in this embodiment is hereinafter referred to as "element 1".

Figure 14:
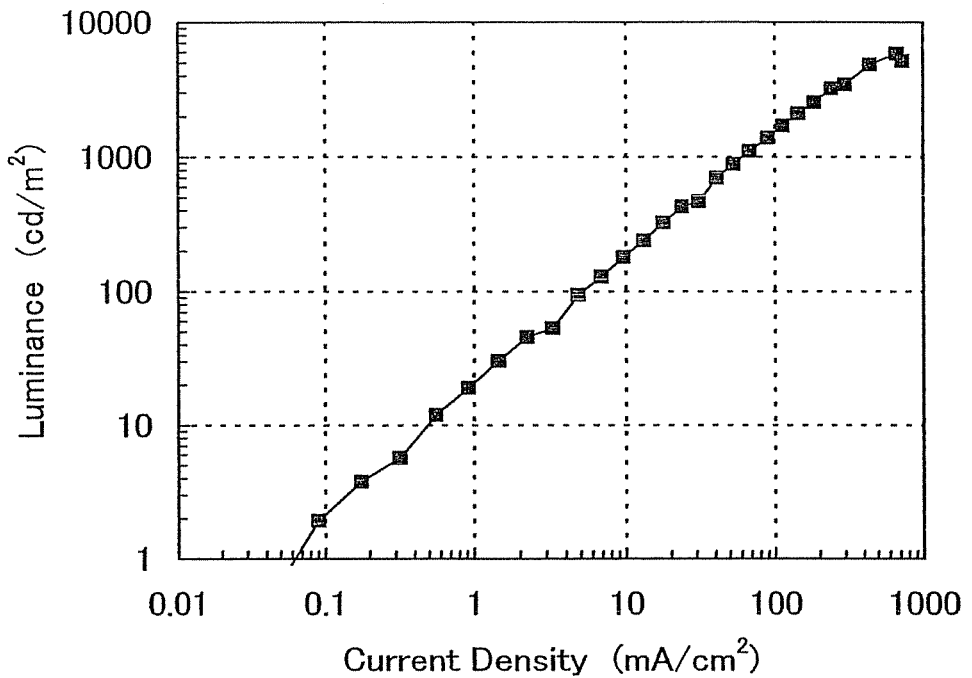
FIG. 14 shows element characteristics of a light-emitting element manufactured using YGACzS.
Figure 15:
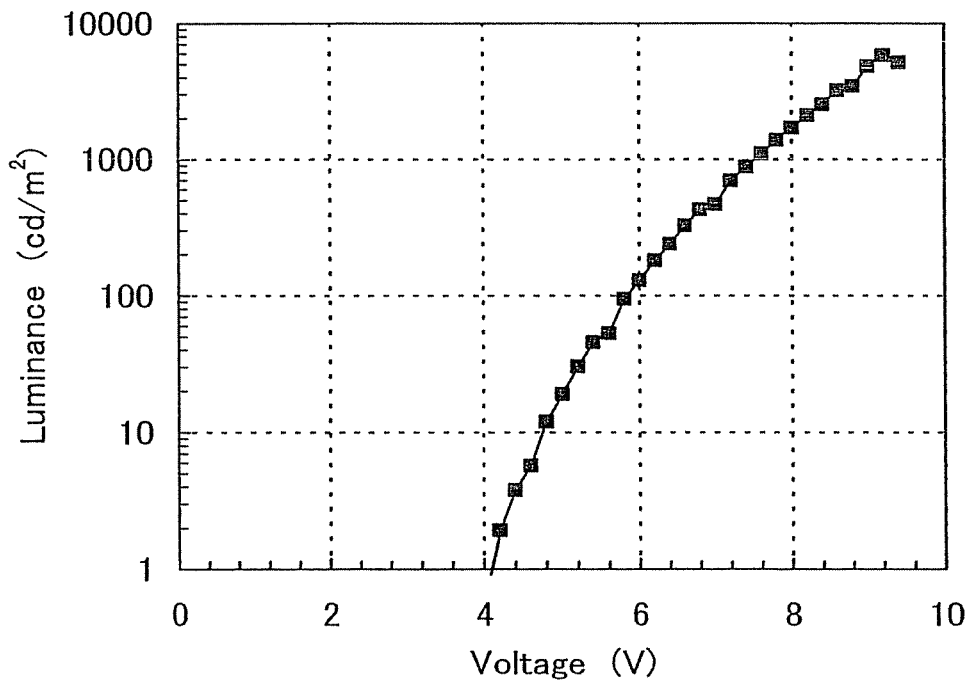
FIG. 15 shows element characteristics of a light-emitting element manufactured using YGACzS.
Figure 16:
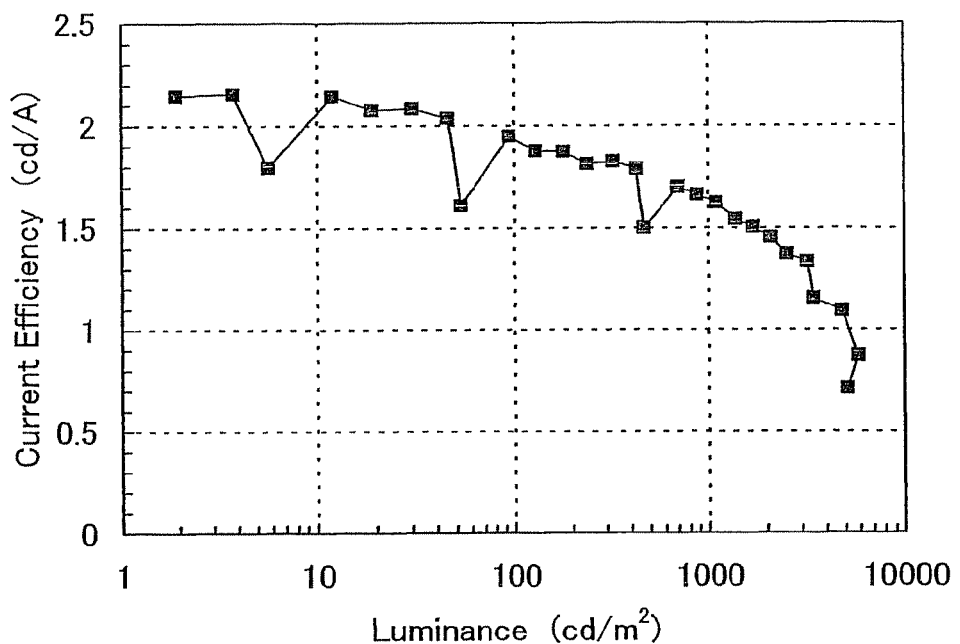
FIG. 16 shows element characteristics of a light-emitting element manufactured using YGACzS.
Figure 17:
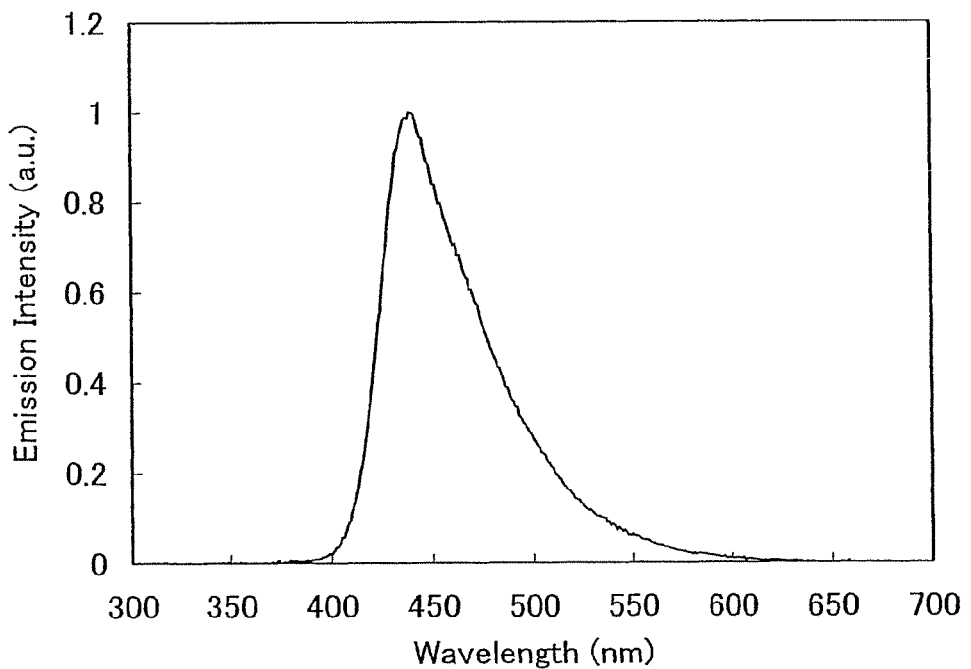
FIG. 17 shows an emission spectrum of a light-emitting element manufactured using YGACzS.

FIG. 14 shows current density-luminance characteristics of the element 1, FIG. 15 shows voltage-luminance characteristics thereof, FIG. 16 shows luminance-current efficiency characteristics thereof, and FIG. 17 shows an emission spectrum thereof. When a voltage of 6.8 V was applied, the element 1 showed a current density of 23.9 mA/cm², a luminance of 430 cd/cm², and a current efficiency of 1.8 cd/A. The element 1 had a peak at 442 nm, and chromaticity coordinates in a CIE colorimetric system were (x, y)=(0.15, 0.09). From these results, it can be seen that the element 1 shows blue emission which substantially conforms to the NTSC standard and is extremely excellent in color purity.

Embodiment 6

In this embodiment, a method for manufacturing a light-emitting element in which (E)-4-{N-[4-(9H-carbazol-9-yl)phenyl]-N-phenyl}amino-4'-(9H-carbazol-9-yl)stilbene (YGACzS) prepared by the synthetic method described in Embodiment 1 is used for a light-emitting layer is described. The light-emitting element to be described in this embodiment is manufactured so that it has the same structure as the light-emitting element described in Embodiment 5, except for the light-emitting layer. Therefore, description of a method for manufacturing and structure is omitted except for that of the light-emitting layer.

The light-emitting layer in this embodiment was formed by evaporation of YGACzS which is a stilbene derivative of the present invention. The light-emitting layer was formed to have a thickness of 30 nm. That is, the light-emitting layer in this embodiment differs from the light-emitting layer in Embodiment 3 in that only YGACzS which is a stilbene derivative of the present invention is used for the light-emitting layer in this embodiment, whereas YGACzS which is a stilbene derivative of the present invention is used as a guest substance (a dopant) of the light-emitting layer in Embodiment 3.

The light-emitting element was manufactured by the above-described method. It is to be noted that the light-emitting element is preferably prevented from being exposed to atmospheric air because deterioration of the light-emitting element is promoted when it is exposed to atmospheric air. Therefore, in this embodiment, sealing was performed using a sealing substrate under a nitrogen atmosphere.

The light-emitting element manufactured as described above was driven by applying voltage to the light-emitting element, and characteristics of the light-emitting element were measured. The light-emitting element manufactured in this embodiment is hereinafter referred to as "element 2".

Figure 18:
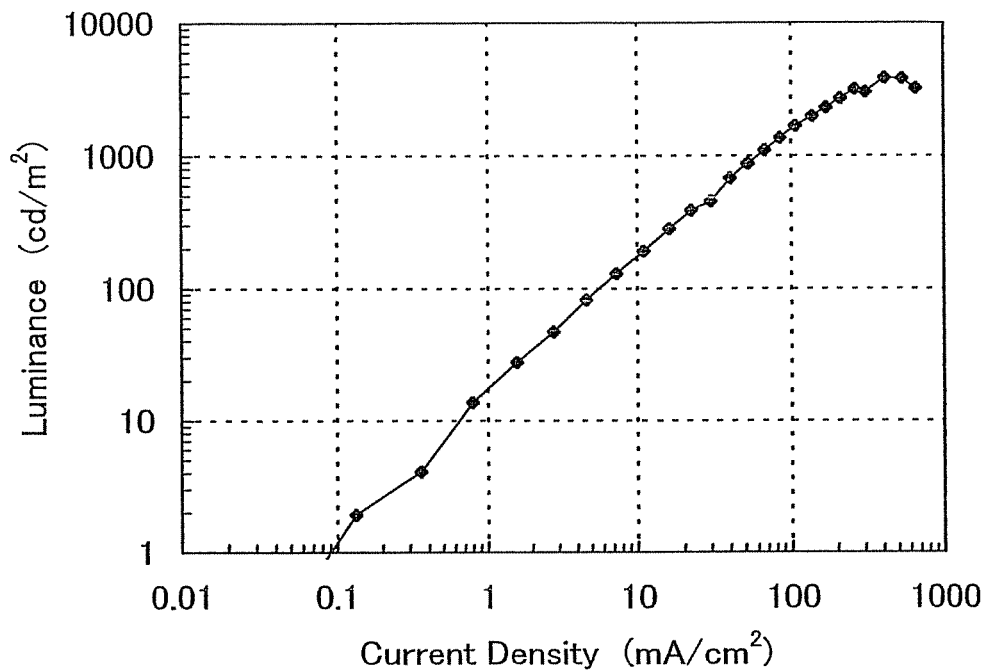
FIG. 18 shows element characteristics of a light-emitting element manufactured using YGACzS.
Figure 19:
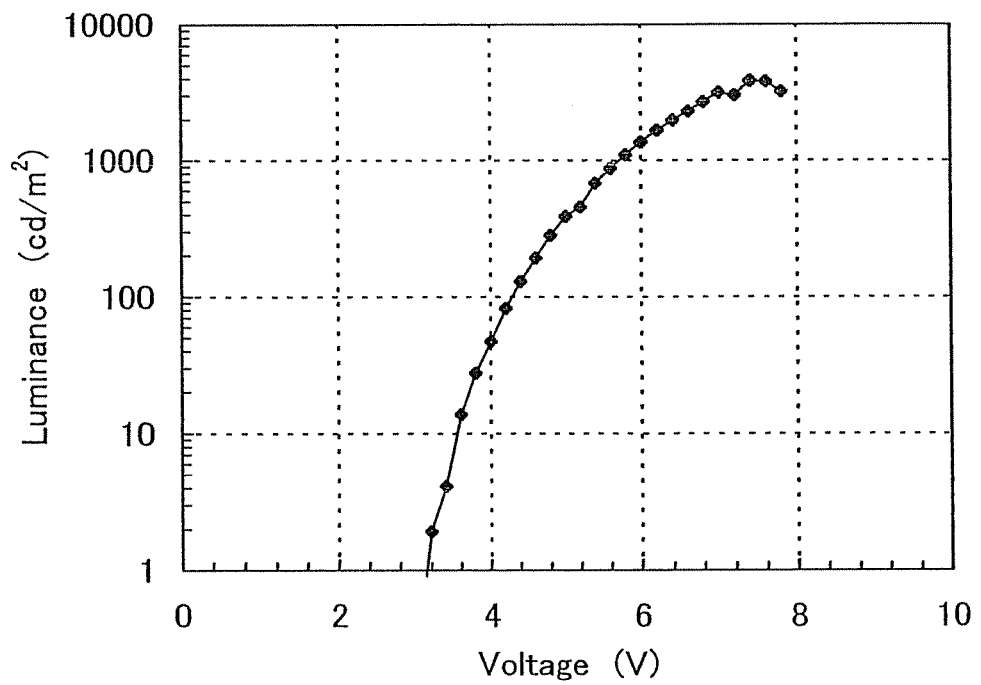
FIG. 19 shows element characteristics of a light-emitting element manufactured using YGACzS.
Figure 20:
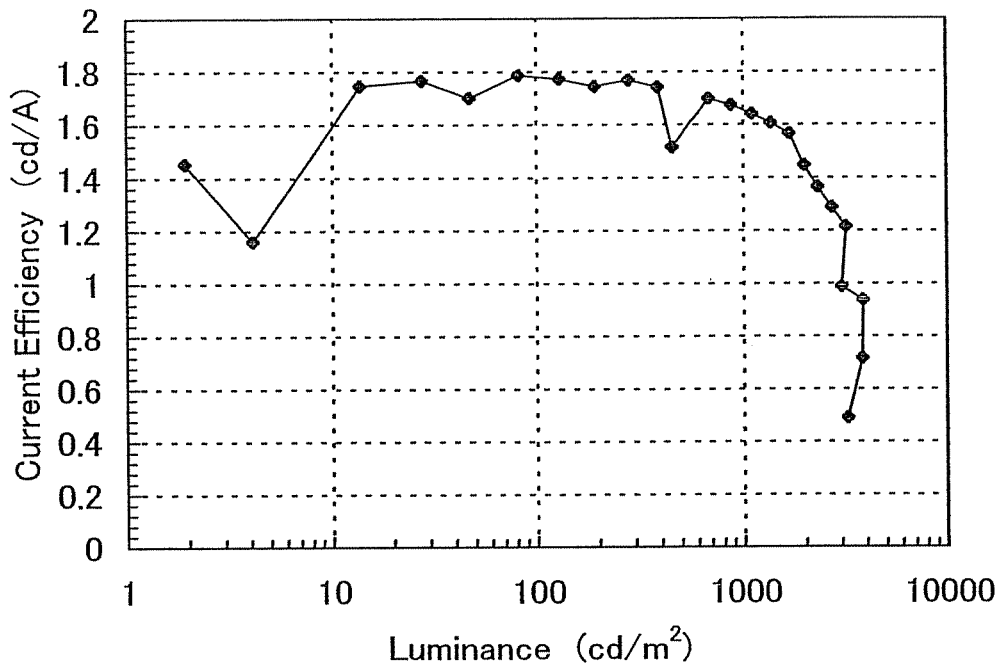
FIG. 20 shows element characteristics of a light-emitting element manufactured using YGACzS.
Figure 21:
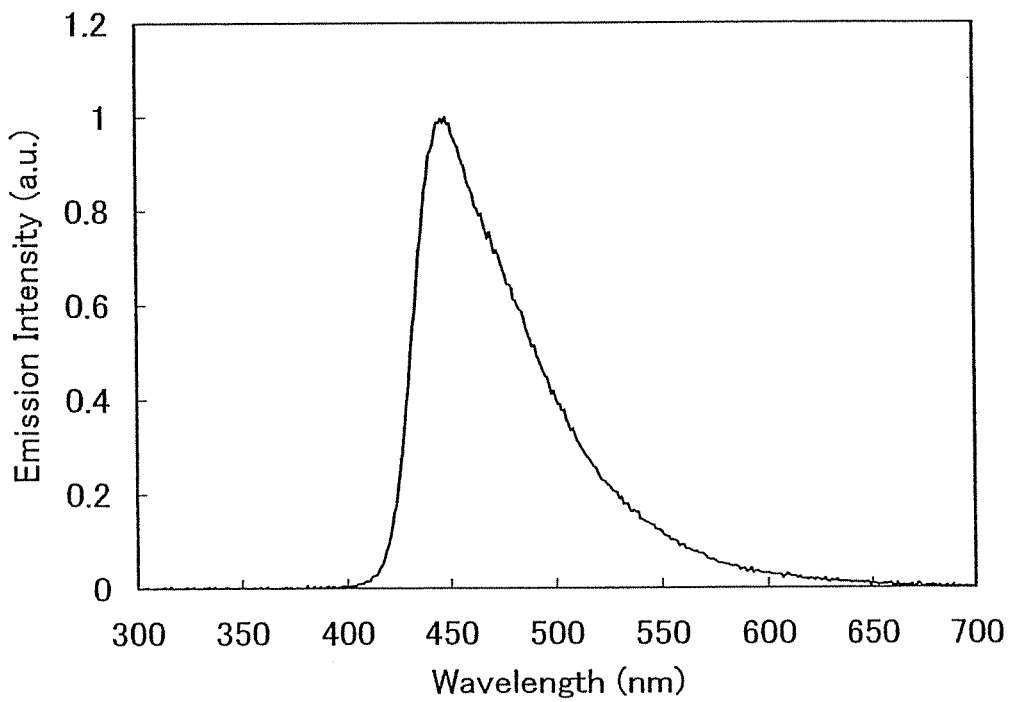
FIG. 21 shows element characteristics of a light-emitting element manufactured using YGACzS.

FIG. 18 shows current density-luminance characteristics of the element 2, FIG. 19 shows voltage-luminance characteristics thereof, FIG. 20 shows luminance-current efficiency characteristics thereof, and FIG. 21 shows emission spectrum thereof. When a voltage of 5.4 V was applied, the element 2 showed a current density of 40.1 mA/cm², a luminance of 680 cd/cm², and a current efficiency of 1.7 cd/A. The element 2 had a peak at 450 nm, and chromaticity coordinates in a CIE colorimetric system were (x, y)=(0.16, 0.14). From these results, it can be seen that the element 2 manufactured using the light-emitting layer formed using only YGACzS also shows blue emission which is excellent in color purity.

Embodiment 7

In this embodiment, a method for manufacturing a light-emitting element in which (E)-4-{N-[4-(9H-carbazol-9-yl)phenyl]-N-phenyl}amino-4'-diphenylaminostilbene (YGA-DPhAS) prepared by the synthetic method described in Embodiment 2 is used for a part (a dopant) of a light-emitting layer is described.

The light-emitting element described in this embodiment is manufactured so that the structure is the same as that of the light-emitting element described in Embodiment 5, except for the light-emitting layer. Therefore, description of a method for manufacturing and structure is omitted, except for that of the light-emitting layer.

The light-emitting layer in this embodiment was formed by co-evaporation of 4,4'-di(N-carbazolyl)biphenyl (abbreviation: CBP) and YGADPhAS, which is a stilbene derivative of the present invention, so that a weight ratio of the CBP and the YGADPhAS was 1:0.05. The light-emitting layer was formed to have a thickness of 30 nm. That is, the light-emitting layer in this embodiment differs from the light-emitting layer in Embodiment 5 in that the YGADPhAS is used as a guest substance of the light-emitting layer in this embodiment, whereas the YGACzS is used as a guest substance of the light-emitting layer in Embodiment 5.

The light-emitting element was manufactured by the above-described method. It is to be noted that the light-emitting element is preferably prevented from being exposed to atmospheric air because deterioration of the light-emitting element is promoted when it is exposed to atmospheric air. Therefore, in this embodiment, sealing was performed using a sealing substrate under a nitrogen atmosphere.

The light-emitting element manufactured as described above was driven by applying voltage to the light-emitting element, and characteristics of the light-emitting element were measured. The light-emitting element manufactured in this embodiment is hereinafter referred to as "element 3".

Figure 22:
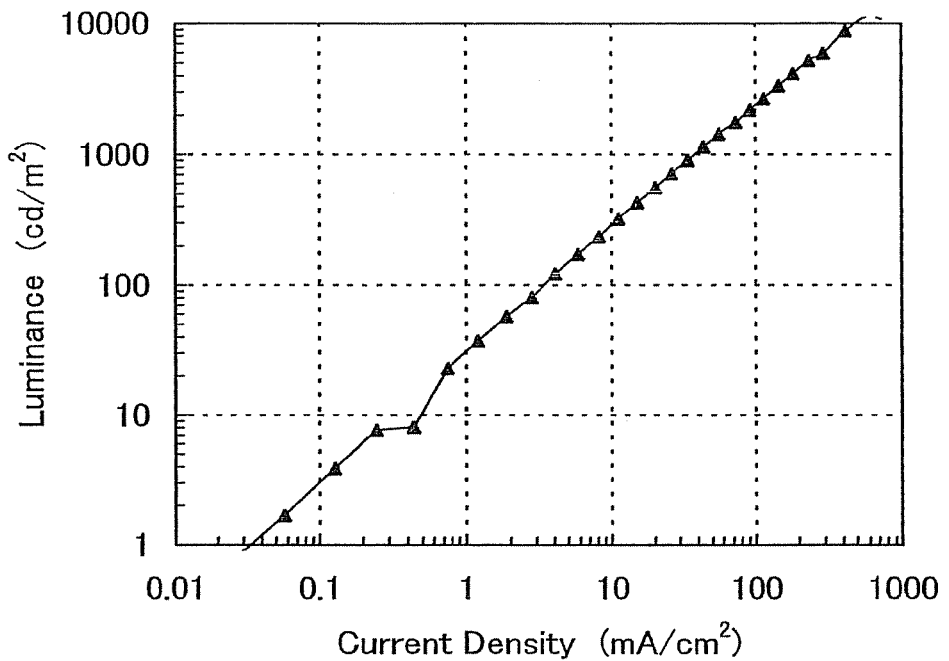
FIG. 22 shows element characteristics of a light-emitting element manufactured using YGADPhAS.
Figure 23:
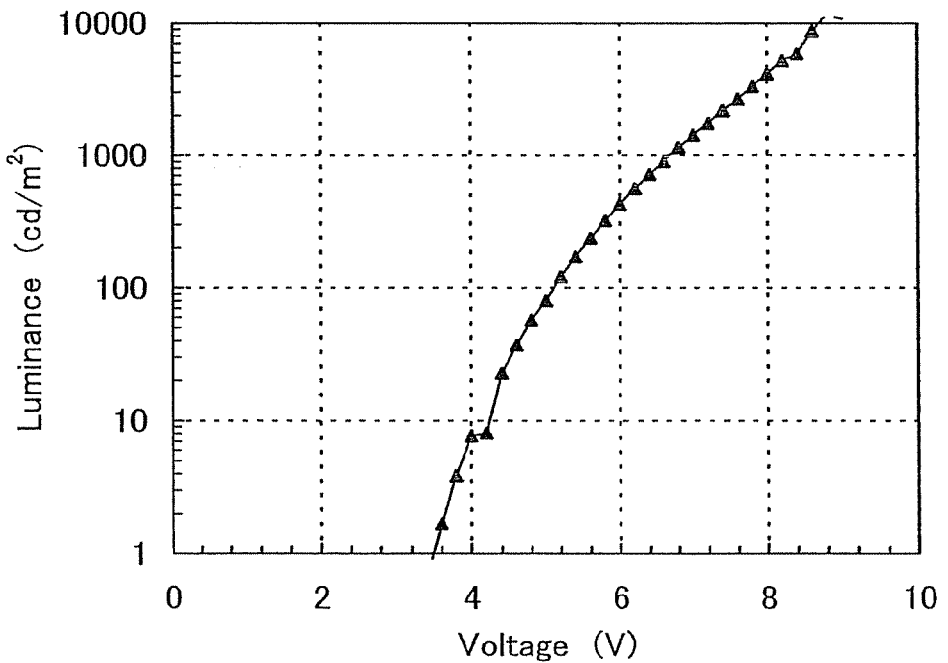
FIG. 23 shows element characteristics of a light-emitting element manufactured using YGADPhAS.
Figure 24:
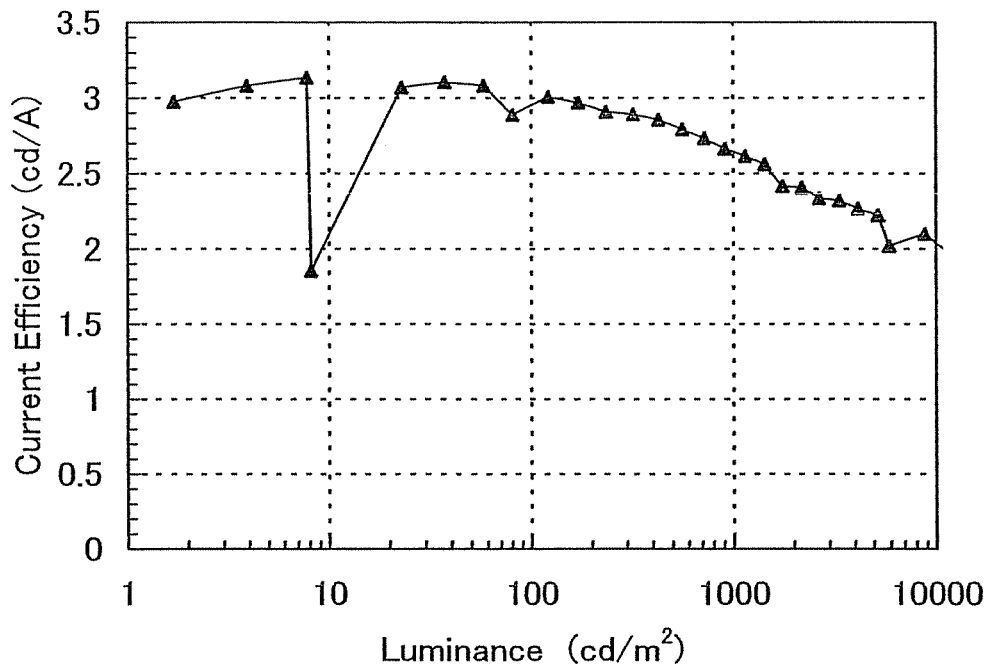
FIG. 24 shows element characteristics of a light-emitting element manufactured using YGADPhAS.
Figure 25:
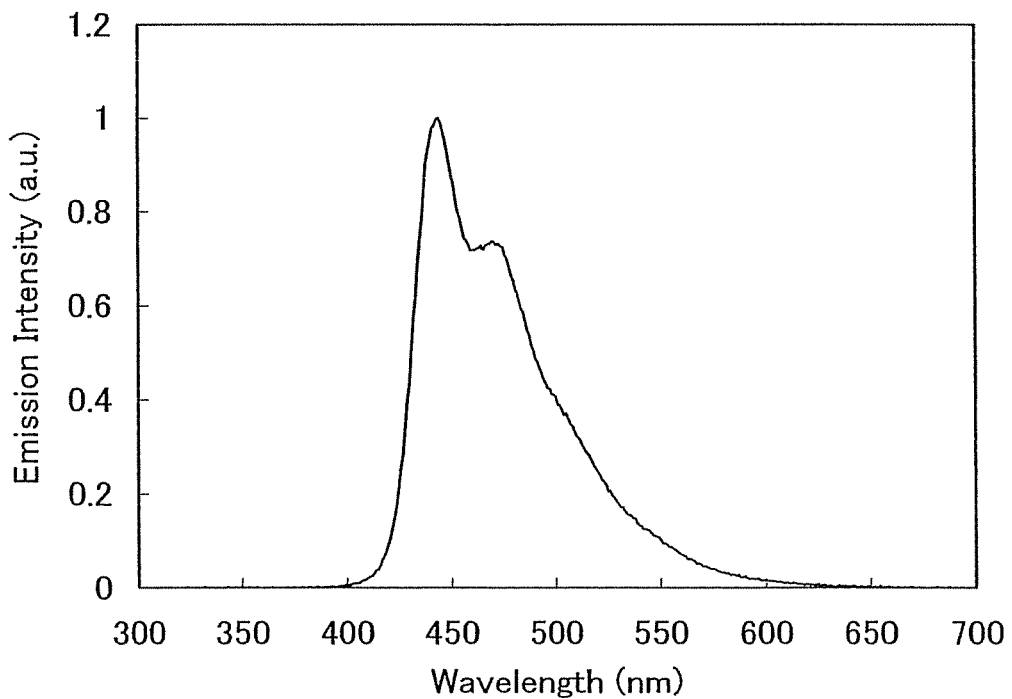
FIG. 25 shows an emission spectrum of a light-emitting element manufactured using YGADPhAS.

FIG. 22 shows current density-luminance characteristics of the element 3, FIG. 23 shows voltage-luminance characteristics thereof, FIG. 24 shows luminance-current efficiency characteristics thereof, and FIG. 25 shows an emission spectrum thereof. When a voltage of 6.2 V was applied, the element 3 showed a current density of 20.1 mA/cm$^2$, a luminance of 560 cd/cm$^2$, and a current efficiency of 2.8 cd/A. The element 3 had a peak at 445 nm, and chromaticity coordinates in a CIE colorimetric system were (x, y)=(0.15, 0.13). From these results, it can be seen that the element 3 also shows blue emission which is excellent in color purity.

This application is based on Japanese Patent Application serial No. 2006-270118 filed in Japan Patent Office on Sep. 29, 2006, the entire contents of which are hereby incorporated by reference.

What is claimed is:

1. An organic compound represented by a general formula (1):

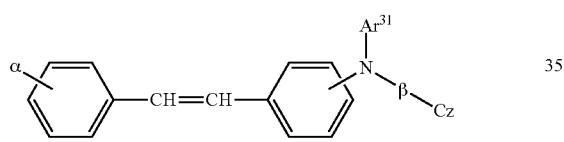

(1)

wherein α represents a carbazolyl group or a diarylamino group,
wherein Ar$^{31}$ represents an aryl group having 6 to 25 carbon atoms,
wherein β represents an arylene group having 6 to 25 carbon atoms,
wherein Cz represents a carbazolyl group, and
wherein the diarylamino group has two aryl groups each independently having 6 to 25 carbon atoms.

2. The organic compound according to claim 1, wherein α comprises a structure represented by the following general formula:

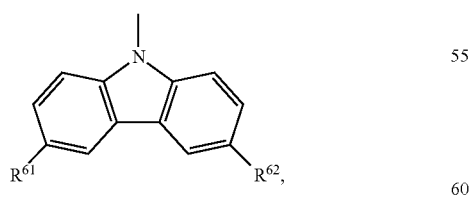

wherein R$^{61}$ and R$^{62}$ each independently represent any one of a hydrogen atom, an alkyl group having 1 to 4 carbon atoms, and an aryl group having 6 to 25 carbon atoms.

3. The organic compound according to claim 1, wherein Cz comprises a structure represented by the following general formula:

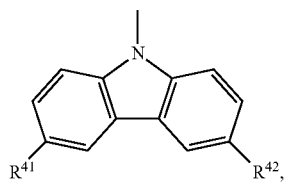

wherein R$^{41}$ and R$^{42}$ each independently represent any one of a hydrogen atom, an alkyl group having 1 to 4 carbon atoms, and an aryl group having 6 to 25 carbon atoms.

4. The organic compound according to claim 1, wherein Ar$^{31}$ comprises a structure represented by any one of the following structural formulae (26-1) to (26-9):

(26-1)

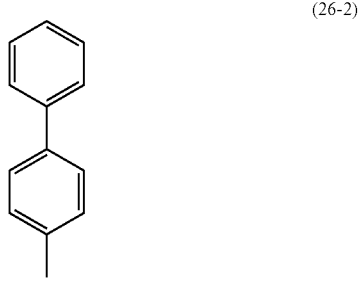

(26-2)

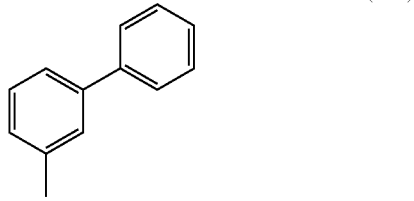

(26-3)

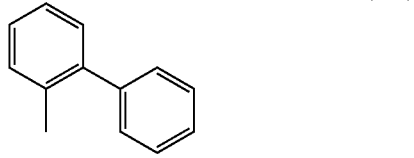

(26-4)

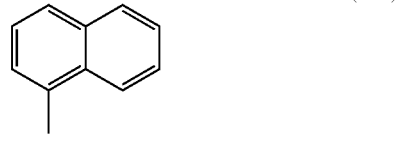

(26-5)

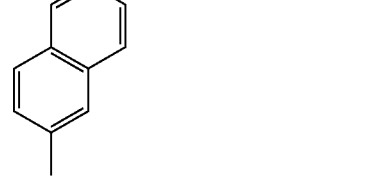

(26-6)

-continued
(26-7)
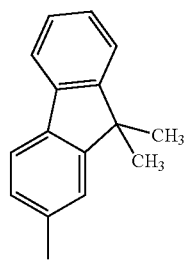
(26-8)
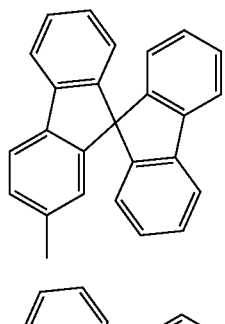
(26-9)
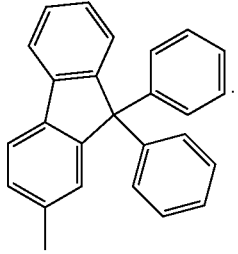
5. The organic compound according to claim 1, wherein β comprises a structure represented by the following structural formulae (27-1) to (27-9):
(27-1)
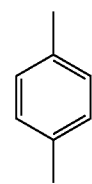
(27-2)
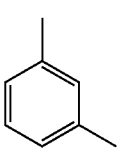
(27-3)
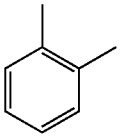
(27-4)
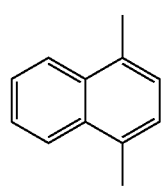
(27-5)
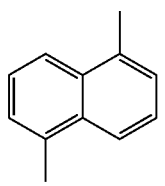
(27-6)
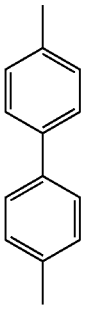
(27-7)
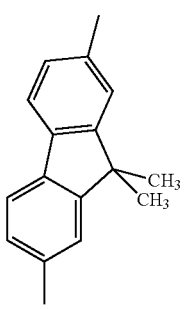
(27-8)
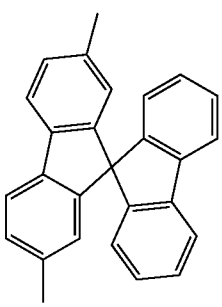
(27-9)
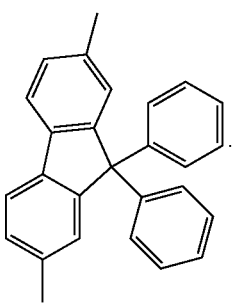
6. The organic compound according to claim 1, wherein the diarylamino group comprises a structure represented by the following general formula:

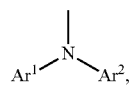

wherein Ar¹ and Ar² each independently have an aryl group having 6 to 25 carbon atoms.

7. A light-emitting element comprising:
a first electrode;
a layer comprising the organic compound according to claim 1, wherein the layer is provided over the first electrode; and
a second electrode over the layer.

8. A display device comprising a display portion comprising the light-emitting element according to claim 7.

* * * * *

UNITED STATES PATENT AND TRADEMARK OFFICE
CERTIFICATE OF CORRECTION

PATENT NO. : 8,704,215 B2  
APPLICATION NO. : 13/417219  
DATED : April 22, 2014  
INVENTOR(S) : Masakazu Egawa et al.

Page 1 of 1

It is certified that error appears in the above-identified patent and that said Letters Patent is hereby corrected as shown below:

In the Specification:

Column 4, Lines 16 to 17; Change "a represents" to --α represents--.

Column 16, Lines 16 to 17; Change "a represents" to --α represents--.

Column 70, Line 6; Change "TZO" to --IZO--.

Signed and Sealed this
Sixteenth Day of September, 2014

Michelle K. Lee
*Deputy Director of the United States Patent and Trademark Office*